US012594341B2

(12) United States Patent
Slavin

(10) Patent No.: US 12,594,341 B2
(45) Date of Patent: Apr. 7, 2026

(54) MULTIFUNCTIONAL IMMUNOTHERAPEUTIC MONOCLONAL ANTIBODY COMPLEXES AND CONJUGATES

(71) Applicant: Shimon Slavin, Tel Aviv (IL)

(72) Inventor: Shimon Slavin, Tel Aviv (IL)

(*) Notice: Subject to any disclaimer, the term of this patent is extended or adjusted under 35 U.S.C. 154(b) by 651 days.

(21) Appl. No.: 18/001,542

(22) PCT Filed: Jun. 14, 2021

(86) PCT No.: PCT/IL2021/050713

§ 371 (c)(1),
(2) Date: Dec. 12, 2022

(87) PCT Pub. No.: WO2021/255723

PCT Pub. Date: Dec. 23, 2021

(65) Prior Publication Data

US 2023/0241240 A1 Aug. 3, 2023

Related U.S. Application Data

(60) Provisional application No. 63/038,828, filed on Jun. 14, 2020.

(51) Int. Cl.

| | |
|---|---|
| ***A61K 47/68*** | (2017.01) |
| ***A61K 35/17*** | (2025.01) |
| ***A61K 38/20*** | (2006.01) |
| ***A61K 39/00*** | (2006.01) |
| ***A61K 39/395*** | (2006.01) |
| ***A61K 40/11*** | (2025.01) |
| ***A61K 40/15*** | (2025.01) |
| ***A61K 40/42*** | (2025.01) |
| ***A61P 35/00*** | (2006.01) |
| ***C07K 16/28*** | (2006.01) |

(52) U.S. Cl.

CPC .......... *A61K 47/6849* (2017.08); *A61K 35/17* (2013.01); *A61K 38/2013* (2013.01); *A61K 39/3955* (2013.01); *A61K 40/11* (2025.01); *A61K 40/15* (2025.01); *A61K 40/4205* (2025.01); *A61K 40/4221* (2025.01); *A61K 40/4222* (2025.01); *A61K 40/428* (2025.01); *A61P 35/00* (2018.01); *C07K 16/2809* (2013.01); *C07K 16/2818* (2013.01); *C07K 16/2887* (2013.01); *A61K 2039/505* (2013.01); *C07K 2317/52* (2013.01); *C07K 2317/54* (2013.01); *C07K 2317/73* (2013.01); *C07K 2317/75* (2013.01)

(58) Field of Classification Search

None

See application file for complete search history.

(56) References Cited

U.S. PATENT DOCUMENTS

| | | | |
|---|---|---|---|
| 5,843,435 | A | 12/1998 | Slavin |
| 5,928,639 | A | 7/1999 | Slavin |
| 6,143,292 | A | 11/2000 | Slavin |
| 6,551,592 | B2 | 4/2003 | Lindhofer |
| 8,066,989 | B2 | 11/2011 | Lindhofer |
| 2014/0271687 | A1 | 9/2014 | Kovesdi |

FOREIGN PATENT DOCUMENTS

| | | | |
|---|---|---|---|
| EP | 0496074 | A1 | 7/1992 |
| EP | 1666500 | B1 | 9/2011 |
| WO | 9524910 | A1 | 9/1995 |
| WO | 9604313 | A1 | 2/1996 |
| WO | 9637208 | A1 | 11/1996 |
| WO | 9820932 | A2 | 5/1998 |
| WO | 2006083562 | A2 | 8/2006 |
| WO | 2017165464 | A1 | 9/2017 |
| WO | 2020010104 | A1 | 1/2020 |

OTHER PUBLICATIONS

Chen, et al. (2016) "Bispecific antibodies in cancer immunotherapy", Human Vaccines & Immunotherapeutics, 12(10): 2491-2500. (Year: 2016).*

Haugland, et al. (2008) "Preparation of avidin conjugates", Methods in Molecular Biology, 418(1): 1-12. (Year: 2008).*

Koristka, et al. (2015) "Tregs activated by bispecific antibodies: Killers or suppressors?", OncoImmunology, 4(3): e994441, 3 pages long. (Year: 2015).*

Maruta, et al. (2019) "Direct comparison of target-reactivity and cross-reactivity induced by CAR- and BiTE-redirected T cells for the development of antibody-base T-cell therapy", Scientific Reports, 9: article 13293. (Year: 2019).*

Correnti, et al. (2018) "Simultaneous Multiple Interaction T-cell Engaging (SMITE) Bispecific Antibodies Overcome Bispecific T-cell Engager (BiTE) Resistance Via CD28 Co-Stimulation", Leukemia, 32: 1239-43. (Year: 2018).*

Zhang, et al. (2023) "Challenges and new technologies in adoptive cell therapy", Journal of Hematology & Oncology, 16, article 97 (55 pages). (Year: 2023).*

(Continued)

*Primary Examiner* — Robert M Kelly

(74) *Attorney, Agent, or Firm* — Ballard Spahr LLP

(57) ABSTRACT

Immunotherapeutic Monoclonal Antibody Complexes or Conjugates (IMAC) comprising readily accessible antibodies designed and approved for clinical use are provided using a one-step method that combines killing of existing cancer cells in parallel with induction of long-lasting anti-cancer vaccination. Methods for their use, alone or in combination with cancer killer cells including intentionally mismatched donor T cells, NK cells concomitantly with additional anti-cancer or immune activating agents, or activation of patient's own immune system for personalized treatment of cancer and elimination of undesirable non-malignant cells are also provided. In addition, treatment method based on IMAC can be applied for in vivo vaccination against cancer using an existing malignant lesion as internal anti-cancer vaccine by engagement of patients antigen presenting cells for induction of long-lasting anti-cancer vaccination in situ against residual or recurrent disease.

18 Claims, 28 Drawing Sheets

(56) References Cited

OTHER PUBLICATIONS

Bayer and Wilchek (1980) The use of the avidin-biotin complex as a tool in molecular biology. Methods Biochem Anal 26: 1-45.
Kipriyanov et al., (1995) Single-chain antibody streptavidin fusions: tetrameric bifunctional scFv-complexes with biotin binding activity and enhanced affinity to antigen. Hum Antibodies Hybridomas 6(3): 93-101.
Paganelli et al., (1991) Monoclonal antibody pretargetting techniques for tumour localization: the avidin-biotin system. Nucl Med Commun 12(3): 211-234.
Ackerstein et al., (2003) Outpatient non-myeloablative immunotherapy with mismatched allogeneic lymphocytes activated with rIL-2 for patients with metastatic solid tumors. Published in final edited version as: Blood 102: 409b (Abstract 5366) American Society of Hematology 45th Annual Meeting, San Diego, California, USA. Dec. 6-9, 2003.
Brudno and Kochenderfer (2016) Toxicities of chimeric antigen receptor T cells: recognition and management. Blood 127(26): 3321-3330.
Buhmann et al., (2009) Immunotherapy of recurrent B-cell malignancies after allo-SCT with Bi20 (FBTA05), a trifunctional anti-CD3 × anti-CD20 antibody and donor lymphocyte infusion. Bone Marrow Transplant 43(5): 383-397.
Burges et al., (2007) Effective relief of malignant ascites in patients with advanced ovarian cancer by a trifunctional anti-EpCAM × anti-CD3 antibody: a phase I/II study. Clin Cancer Res 13(13): 3899-3905.
Chelius et al., (2010) Structural and functional characterization of the trifunctional antibody catumaxomab. MAbs 2(3): 309-319.
Cohen et al., (1993) Spontaneous and IL-2-induced anti-leukemic and anti-host effects against tumor- and host-specific alloantigens. J Immunol 151(9): 4803-4810.
D'Argouges et al., (2009) Combination of rituximab with blinatumomab (MT103/MEDI-538), a T cell-engaging CD19-/CD3-bispecific antibody, for highly efficient lysis of human B lymphoma cells. Leuk Res 33(3): 465-473.
Daniele et al., (2012) Overview of T-cell depletion in haploidentical stem cell transplantation. Blood Transfus 10(3): 264-272.
De Nardis et al., (2017) A new approach for generating bispecific antibodies based on a common light chain format and the stable architecture of human immunoglobulin G1. J Biol Chem, published online Jun. 27, 2017. 26 pages.
Deppisch et al., (2015) Efficacy and Tolerability of a GD2-Directed Trifunctional Bispecific Antibody in a Preclinical Model: Subcutaneous Administration Is Superior to Intravenous Delivery. Mol Cancer Ther 14(8): 1877-1883.
Eissler et al., (2012) Trifunctional bispecific antibodies induce tumor-specific T cells and elicit a vaccination effect. Cancer Res 72(16): 3958-3966.
Eissler et al., (2013) Potential of the trifunctional bispecific antibody surek depends on dendritic cells: rationale for a new approach of tumor immunotherapy. Mol Med 19(1): 54-61.
Haense et al., (2016) A phase I trial of the trifunctional anti Her2 × anti CD3 antibody ertumaxomab in patients with advanced solid tumors. BMC Cancer 16: 420.
Heiss et al., (2005) Immunotherapy of malignant ascites with trifunctional antibodies. Int J Cancer 117(3): 435-443.
Heiss et al., (2010) The trifunctional antibody catumaxomab for the treatment of malignant ascites due to epithelial cancer: Results of a prospective randomized phase II/III trial. Int J Cancer 127(9): 2209-2221.
Hess et al., (2012) Cancer therapy with trifunctional antibodies: linking innate and adaptive immunity. Future Oncol 8(1): 73-85.
Jäger et al., (2009) The trifunctional antibody ertumaxomab destroys tumor cells that express low levels of human epidermal growth factor receptor 2. Cancer Res 69(10): 4270-4276.
Jäger et al., (2012) Immunomonitoring results of a phase II/III study of malignant ascites patients treated with the trifunctional antibody catumaxomab (anti-EpCAM × anti-CD3). Cancer Res 72(1): 24-32.
Kieslich et al., (2017) Immunotherapy with the trifunctional anti-CD20 × anti-CD3 antibody FBTA05 in a patient with relapsed t(8;14)-positive post-transplant lymphoproliferative disease. Leuk Lymphoma 58(8): 1989-1992.
Kiewe et al., (2006) Phase I trial of the trifunctional anti-HER2 × anti-CD3 antibody ertumaxomab in metastatic breast cancer. Clin Cancer Res 12(10): 3085-3091.
Lindhofer et al., (1996) Bispecific antibodies target operationally tumor-specific antigens in two leukemia relapse models. Blood 88(12): 4651-4658.
Luznik et al., (2008) HLA-haploidentical bone marrow transplantation for hematologic malignancies using nonmyeloablative conditioning and high-dose, posttransplantation cyclophosphamide. Biol Blood Marrow Transplant 14(6): 641-650.
Morecki et al., (2004) Allogeneic versus syngeneic killer splenocytes as effector cells for the induction of graft-versus-tumor effect. Biol Blood Marrow Transplant 10(1): 40-48.
Morecki et al., (2006) Use of trifunctional bispecific antibodies to prevent graft versus host disease induced by allogeneic lymphocytes. Blood 107(4): 1564-1569.
Morecki et al., (2008) Induction of long-lasting antitumor immunity by concomitant cell therapy with allogeneic lymphocytes and trifunctional bispecific antibody. Exp Hematol 36(8): 997-1003.
Muros et al., (2009) Outcome of treating advanced neuroendocrine tumours with radiolabelled somatostatin analogues. Clin Transl Oncol 11(1): 48-53.
Nagler et al., (2000) Adoptive immunotherapy with haploidentical allogeneic peripheral blood lymphocytes following autologous bone marrow transplantation. Exp Hematol 28(11): 1225-1231.
Neelapu et al., (2018) Chimeric antigen receptor T-cell therapy—assessment and management of toxicities. Nat Rev Clin Oncol 15(1): 47-62.
Or et al., (1998) Allogeneic cell-mediated and cytokine-activated immunotherapy for malignant lymphoma at the stage of minimal residual disease after autologous stem cell transplantation. J Immunother 21(6): 447-453. Abstract.
Ott et al., (2012) Humoral response to catumaxomab correlates with clinical outcome: results of the pivotal phase II/III study in patients with malignant ascites. Int J Cancer 130(9): 2195-2203.
Paganelli et al., (2010) Intraoperative avidination for radionuclide treatment as a radiotherapy boost in breast cancer: results of a phase II study with (90)Y-labeled biotin. Eur J Nucl Med Mol Imaging 37(2): 203-211.
Panigrahi et al., (2002) Intraportal and systemic allogeneic cell therapy in a murine model of hepatic metastatic breast cancer. Cytokines Cell Mol Ther 7(3): 99-106.
Park et al., (2018) Long-Term Follow-up of CD19 CAR Therapy in Acute Lymphoblastic Leukemia. N Engl J Med 378(5): 449-459.
Petronzelli et al., (2010) Therapeutic use of avidin is not hampered by antiavidin antibodies in humans. Cancer Biother Radiopharm 25(5): 563-570.
Pietzner et al., (2012) First patient treated with a re-challenge of catumaxomab in recurrent malignant ascites: a case report. Med Oncol 29(2): 1391-1396.
Pietzner et al., (2013) Expression of epithelial cell adhesion molecule in paired tumor samples of patients with primary and recurrent serous ovarian cancer. Int J Gynecol Cancer 23(5): 797-802. Abstract.
Riesenberg et al., (2001) Lysis of prostate carcinoma cells by trifunctional bispecific antibodies (alpha EpCAM × alpha CD3). J Histochem Cytochem 49(7): 911-917.
Ruf and Lindhofer (2001) Induction of a long-lasting antitumor immunity by a trifunctional bispecific antibody. Blood 98(8): 2526-2534.
Ruf et al., (2004) Two new trifunctional antibodies for the therapy of human malignant melanoma. Int J Cancer 108(5): 725-732.
Ruf et al., (2010) Pharmacokinetics, immunogenicity and bioactivity of the therapeutic antibody catumaxomab intraperitoneally administered to cancer patients. Br J Clin Pharmacol 69(6): 617-625.
Ruf et al., (2012) Ganglioside GD2-specific trifunctional surrogate antibody Surek demonstrates therapeutic activity in a mouse melanoma model. J Transl Med 10: 219.
Schmitt et al., (2004) Opsonization with a trifunctional bispecific (alphaCD3 × alphaEpCAM) antibody results in efficient lysis in

(56) References Cited

OTHER PUBLICATIONS vitro and in vivo of EpCAM positive tumor cells by cytotoxic T lymphocytes. Int J Oncol 25(4): 841-848.
Schuster et al., (2015) Immunotherapy with the trifunctional anti-CD20 × anti-CD3 antibody FBTA05 (Lymphomun) in paediatric high-risk patients with recurrent CD20-positive B cell malignancies. Br J Haematol 169(1): 90-102.
Sebastian et al., (2007) Treatment of non-small cell lung cancer patients with the trifunctional monoclonal antibody catumaxomab (anti-EpCAM × anti-CD3): a phase I study. Cancer Immunol Immunother 56(10): 1637-1644.
Sebastian et al., (2009) Treatment of malignant pleural effusion with the trifunctional antibody catumaxomab (Removab) (anti-EpCAM × Anti-CD3): results of a phase 1/2 study. J Immunother 32(2): 195-202.
Slavin et al., (1995) Allogeneic cell therapy for relapsed leukemia after bone marrow transplantation with donor peripheral blood lymphocytes. Exp Hematol 23(14): 1553-1562. Abstract.
Slavin et al., (1996) Allogeneic cell therapy with donor peripheral blood cells and recombinant human interleukin-2 to treat leukemia relapse after allogeneic bone marrow transplantation. Blood 87(6): 2195-2204.
Slavin et al., (1998) Nonmyeloablative stem cell transplantation and cell therapy as an alternative to conventional bone marrow transplantation with lethal cytoreduction for the treatment of malignant and nonmalignant hematologic diseases. Blood 91(3): 756-763.
Slavin et al., (2003) Immunotherapy for resistant hematologic malignancies using matched or mismatched rIL-2 activated donor lymphocytes positively selected for CD56+ after allogeneic stem cell transplantation for allogeneic cell therapy without GVHD. Published in final edited version as: Blood 102: 400b (Abstract 5329) American Society of Hematology 45th Annual Meeting, San Diego, California, USA. Dec. 6-9, 2003.
Slavin et al., (2010) Immunotherapy in high-risk chemotherapy-resistant patients with metastatic solid tumors and hematological malignancies using intentionally mismatched donor lymphocytes activated with rIL-2: a phase I study. Cancer Immunol Immunother 59(10): 1511-1519.
Stanglmaier et al., (2008) BI20 (fBTA05), a novel trifunctional bispecific antibody (anti-CD20 × anti-CD3), mediates efficient killing of B-cell lymphoma cells even with very low CD20 expression levels. Int J Cancer 123(5): 1181-1189.
Stemmler et al., (2005) Combined treatment of metastatic breast cancer (MBC) by high-dose chemotherapy (HDCT) and bispecific antibodies: a pilot study. Anticancer Res 25(4): 3047-3054.
Stemmler et al., (2005) Lasting remission following multimodal treatment in a patient with metastatic breast cancer. Anticancer Drugs 16(10): 1135-1137.
Ströhlein et al., (2009) Induction of anti-tumor immunity by trifunctional antibodies in patients with peritoneal carcinomatosis. J Exp Clin Cancer Res 28(1): 18.
Ströhlein et al., (2011) Immunotherapy of peritoneal carcinomatosis with the antibody catumaxomab in colon, gastric, or pancreatic cancer: an open-label, multicenter, phase I/II trial. Onkologie 34(3): 101-108.
Tsirigotis et al., (2014) Irradiated mononuclear cells express significant in vitro cytotoxic activity: promise for in vivo clinical efficacy of irradiated mismatched donor lymphocytes infusion. Immunotherapy 6(4): 409-417.
Weiss et al., (1982) Natural cell-mediated cytotoxicity in mice treated with total lymphoid irradiation (TL1). Cell Immunol 70(1): 188-195.
Wimberger et al., (2009) Influence of catumaxomab on tumor cells in bone marrow and blood in ovarian cancer. Anticancer Res 29(5): 1787-1791.
Zarcone et al., (1989) Radiation sensitivity of resting and activated nonspecific cytotoxic cells of T lineage and NK lineage. Blood 73(6): 1615-1621.
Zeidler et al., (1999) Simultaneous activation of T cells and accessory cells by a new class of intact bispecific antibody results in efficient tumor cell killing. J Immunol 163(3): 1246-1252.
Zeidler et al., (2000) The Fc-region of a new class of intact bispecific antibody mediates activation of accessory cells and NK cells and induces direct phagocytosis of tumour cells. Br J Cancer 83(2): 261-266.
Seimetz et al., (2010) Development and approval of the trifunctional antibody catumaxomab (anti-EpCAM × anti-CD3) as a targeted cancer immunotherapy. Cancer Treat Rev 36(6): 458-467. Abstract.
Slavin (2000) Cancer immunotherapy with alloreactive lymphocytes. N Engl J Med 343(11): 802-803.
Slavin (2001) Immunotherapy of cancer with alloreactive lymphocytes. Lancet Oncol 2(8): 491-498.
Slavin (2005) Allogeneic cell-mediated immunotherapy at the stage of minimal residual disease following high-dose chemotherapy supported by autologous stem cell transplantation. Acta Haematol 114(4): 214-220.
Slavin et al., (1992) Immunotherapy of minimal residual disease in conjunction with autologous and allogeneic bone marrow transplantation (BMT), Leukemia 6 Suppl 4: 164-166. Abstract.

* cited by examiner

Biotin

Avidin

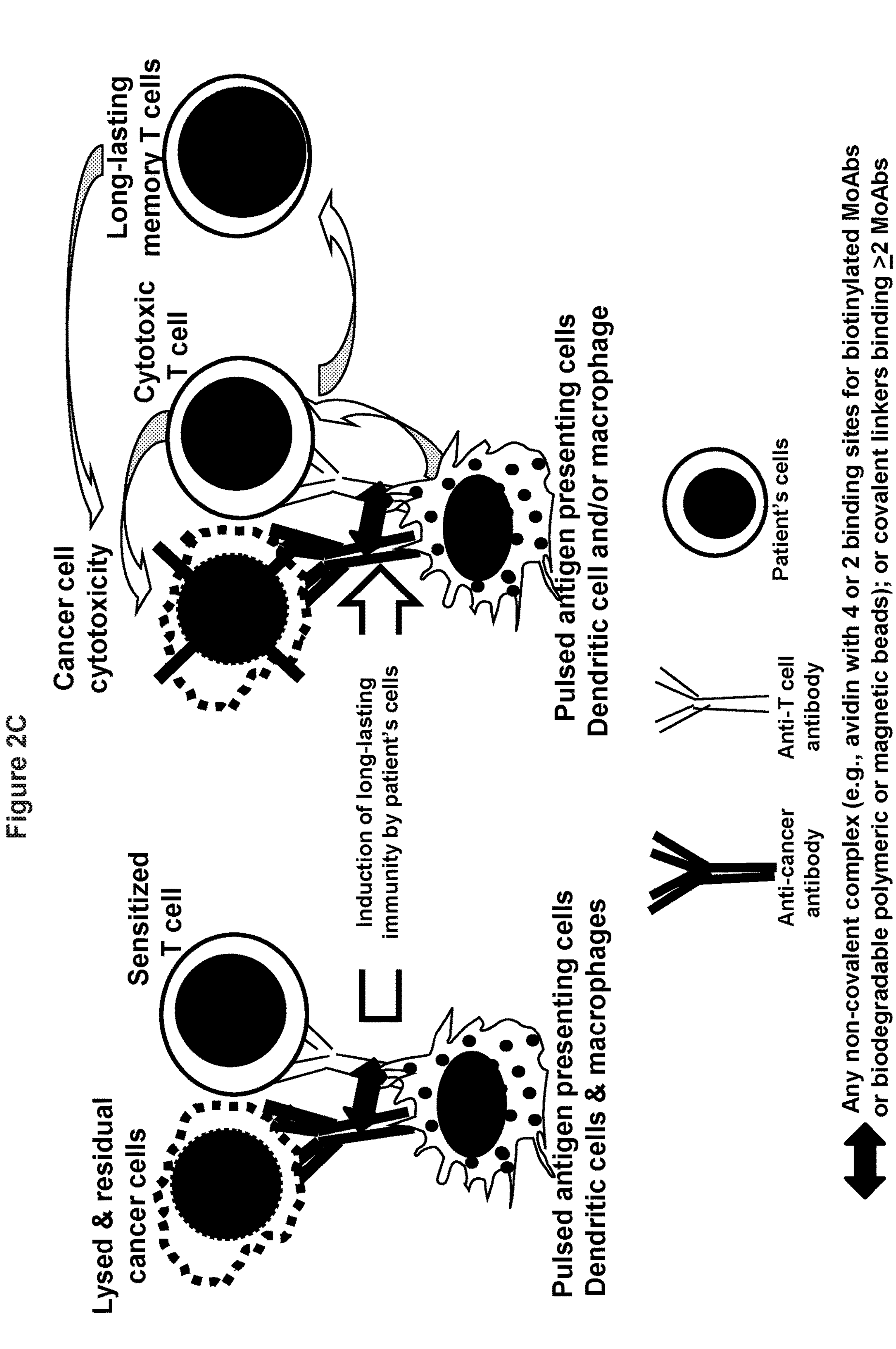
Figure 2C
Lysed & residual cancer cells
Sensitized T cell
Pulsed antigen presenting cells Dendritic cells & macrophages
Induction of long-lasting immunity by patient's cells
Cancer cell cytotoxicity
Cytotoxic T cell
Long-lasting memory T cells
Pulsed antigen presenting cells Dendritic cell and/or macrophage
Anti-cancer antibody
Anti-T cell antibody
Patient's cells
Any non-covalent complex (e.g., avidin with 4 or 2 binding sites for biotinylated MoAbs or biodegradable polymeric or magnetic beads); or covalent linkers binding ≥2 MoAbs

Figure 16

| Treatment | | CD45 | Viable CD45 | | CD3 | | %CD3 from CD45 | NK | | %NK from CD45 | Tregs | | %Tregs from CD45 |
|---|---|---|---|---|---|---|---|---|---|---|---|---|---|
| IL-2 (6000 IU/mL) | 1.1 | 126,332 | 123,193 | 128,796 | 98,481 | 102,645 | 79.7% | 22,237 | 22,520 | 17.5% | 2,200 | 2,170 | 1.7% |
| | 1.2 | 138,516 | 134,399 | | 106,809 | | | 22,803 | | | 2,140 | | |
| IL-2 (6000 IU/mL) + PHA 5 µg/mL | 2.1 | 169,247 | 163,240 | 165,941 | 145,937 | 147,468 | 88.9% | 8,396 | 8,228 | 5.0% | 4,685 | 4,184 | 2.5% |
| | 2.2 | 174,882 | 168,642 | | 148,998 | | | 8,059 | | | 3,682 | | |
| IL-2 (6000 IU/mL) + KRN7000 100 ng/mL | 3.1 | 191,296 | 186,308 | 172,560 | 150,679 | 138,977 | 80.5% | 34,735 | 30,763 | 17.8% | 3,829 | 3,299 | 1.9% |
| | 3.2 | 162,526 | 158,812 | | 127,274 | | | 26,790 | | | 2,768 | | |
| IL-2 (6000 IU/mL) + KRN7000 1,000 ng/mL | 4.1 | 149,166 | 144,638 | 167,806 | 116,488 | 134,505 | 80.2% | 26,937 | 32,005 | 19.1% | 2,134 | 2,424 | 1.4% |
| | 4.2 | 196,183 | 190,974 | | 152,522 | | | 37,073 | | | 2,714 | | |
| IL-2 (6000 IU/mL) + KRN7000 100 ng/mL + PHA 5 µg/mL | 5.1 | 203,547 | 195,365 | 183,103 | 177,991 | 166,253 | 90.8% | 12,256 | 10,708 | 5.8% | 7,148 | 5,469 | 3.0% |
| | 5.2 | 178,797 | 170,841 | | 154,515 | | | 9,160 | | | 3,789 | | |
| KRN7000 100 ng/mL | 6.1 | 58,121 | 56,006 | 52,565 | 51,096 | 47,720 | 90.8% | 634 | 621 | 1.2% | 1,381 | 1,352 | 2.6% |
| | 6.2 | 51,319 | 49,123 | | 44,344 | | | 608 | | | 1,323 | | |
| KRN7000 1000 ng/mL | 7.1 | 50,236 | 49,388 | 51,817 | 44,920 | 46,936 | 90.6% | 658 | 670 | 1.3% | 1,091 | 1,117 | 2.2% |
| | 7.2 | 56,208 | 54,246 | | 48,951 | | | 681 | | | 1,143 | | |
| KRN7000 100 ng/mL + PHA 5 µg/mL | 8.1 | 75,276 | 69,987 | 68,929 | 63,154 | 61,307 | 88.9% | 1,518 | 1,734 | 2.5% | 1,876 | 1,730 | 2.5% |
| | 8.2 | 74,812 | 67,871 | | 59,460 | | | 1,949 | | | 1,583 | | |
| PHA 5 µg/mL | 9.1 | 73,868 | 69,226 | 68,477 | 61,377 | 60,564 | 88.4% | 1,524 | 1,477 | 2.2% | 1,683 | 1,583 | 2.3% |
| | 9.2 | 73,859 | 67,727 | | 59,751 | | | 1,429 | | | 1,482 | | |
| untreated cells | 10.1 | 17,508 | 17,113 | 22,656 | 15,367 | 20,225 | 89.3% | 128 | 137 | 0.6% | 337 | 367 | 1.6% |
| | 10.2 | 29,016 | 28,199 | | 25,082 | | | 145 | | | 396 | | |

MULTIFUNCTIONAL IMMUNOTHERAPEUTIC MONOCLONAL ANTIBODY COMPLEXES AND CONJUGATES

FIELD OF THE INVENTION

The present invention is in the field of cancer immunotherapy and cancer vaccination. The present invention specifically relates to multifunctional complexes of targeting and activating antibodies and their uses in eliminating malignant and other cells and infective agents.

BACKGROUND OF THE INVENTION

Cell-mediated immunotherapy is currently considered as one the most promising approaches for the treatment of multi-drug resistant cancer, especially when all other available modalities fail to cure the patient. Allogeneic stem cell transplantation (SCT), which is one of the earliest cell-mediated procedures for treatment of hematologic malignancies, is commonly used for treating resistant or relapsing acute (ALL and AML) and progressive chronic leukemia (CLL and CML), non-Hodgkin's lymphoma (NHL) and Hodgkin's lymphoma (HL), multiple myeloma and other hematopoietic malignancies that fail to respond to maximally tolerated doses of chemotherapy and radiation. Post-transplant administration of alloreactive donor lymphocytes or earlier withdrawal of post-grafting immunosuppressive treatment following stem cell transplantation improves the patient's response and allows better control of the malignant disease following reduced intensity conditioning (RIC) or non-myeloablative stem cell transplantation (NST). Following engraftment of donor's hematopoietic stem cells, the resulting host-vs-graft tolerance allows durable engraftment of donor's immunocompetent anti-cancer effector cells, which include both T cells and natural killer (NK) cells present in donor's mononuclear cells used for treatment (1-8).

Unfortunately, despite the use of fully HLA matched sibling, matched unrelated donor or even haploidentical donor, the use of allogeneic SCT is accompanied by life-threatening procedure-related toxicity, especially infections and bleeding during pancytopenia induced by the conditioning and especially hazardous acute and chronic graft versus host disease (GVHD). Interestingly, lower relapse rate can be accomplished by using haploidentically mismatched donors with GVHD prevention by either pre-transplant (9) or post-transplant T cell depletion (10), but still, short-term or longer-term post grafting immunosuppressive anti-GVHD prophylaxis is usually unavoidable. Acute and chronic GVHD cannot be fully prevented and worst of all, despite optimal cytoreductive treatment and effective graft-vs-tumor effects, relapse of the original malignancy still presents the major cause of failure. Taken together, recurrent disease continues to be the major cause of treatment failure despite successful allogeneic stem cell transplantation. To overcome this disadvantage and attempting to avoid the need for hazardous and expensive allogeneic SCT, a strategy based on administration of fully or preferably haploidentically mismatched donor lymphocytes was developed avoiding the need for prior SCT, consequently avoiding the need for using high-dose chemotherapy and immunosuppressive treatment, intentionally avoiding induction of host-vs-graft unresponsiveness. The method includes transient circulation of intentionally mismatched T cells and NK cells activated with cytokines (e.g., IL-2) in vitro prior to administration, with possible continuous in vivo activation of donor lymphocytes following cell infusion until their expected rejection. As a result, substantial anti-cancer effects can be induced by short-term circulation of most potent anti-cancer killer cells, while consistent rejection of intentionally mismatched donor lymphocytes within 7 to 10 days prevents the development of any GVHD which depends on durable engraftment of alloreactive donor T lymphocytes (1-10). Targeting of killer cells against cancer cells can be enhanced by concomitant administration of antibodies against cancer-associated antigens (e.g., CD20 or CD19 against malignant B cells), thus resulting in antibody-dependent cell-mediated cytotoxicity.

Bispecific antibodies composed of one anti-CD3 single chain Fab that binds T cells and a second Fab against tumor antigens (e.g., anti-CD3×anti-CD20, or anti-CD3×anti-EpCAM bispecific antibodies) were developed for selective targeting of autologous cells to tumor tissue (11, 12). Subsequently, it was reported that the bispecific antibody can be applied with intentionally mismatched T cells and NK cells resulting in most effective selective cytotoxic activity against cancer cells while avoiding any risk of anti-host effects known as GVHD due to preferential targeting of donor T cells against cancer cells on the one hand, and due to anticipated rejection of intentionally mismatched donor lymphocytes (13). Cytotoxic activity by mismatched donor's T cells and NK cells that resulted in eradication of all cancer cells was followed by activation of recipient's own immune system when recipient's dendritic cells pulsed with cancer antigens sensitized recipient's T cells, resulting in induction of long-lasting memory T cells that could eliminate a fresh challenge of lethal inoculum of cancer cells months following elimination of donor lymphocytes and the bispecific antibody (13, 14).

U.S. Pat. No. 8,066,989 (15) and EP Patent No. 1666500 (16) disclose methods for treating tumor growth and metastasis in a patient by administering allogenic effector cells together with trifunctional bispecific antibodies capable of binding simultaneously to a T cell, to at least one tumor antigen and to Fc receptor positive cells. These antibodies can re-direct the allogenic cells away from normal host tissues before being fully rejected in order to substantially reduce or avoid development of GVHD.

Trifunctional bispecific antibodies are artificially engineered immunoglobulins that can direct T cells to tumor cells, and also induce recruitment and activation of accessory cells through their Fc region. The simultaneous activation of different mechanisms at the tumor site such as phagocytosis, perforin mediated lysis and cytokine release results in a particularly efficient destruction of tumor cells. The binding of the Fc portion of the targeting bispecific antibody to the Fc receptor of antigen presenting cells, dendritic cells and macrophages, results in processing of cancer antigens, presentation of cancer associated peptides to helper T cells and induction of memory T cells that can maintain anti-cancer immunotherapy by resident memory cells of host origin (10-14). Bispecific tri-functional antibodies aim to provide a single treatment method for dual anti-cancer effects: elimination of malignant cells by alloreactive donor lymphocytes and/or cytokine-activated patient's lymphocytes; and induction of long-lasting anti-cancer immunity. Unfortunately, there is no evidence that commercially available bispecific antibodies can fulfil this potential. In addition, developing trifunctional bispecific antibodies is technically cumbersome, very expensive and time consuming and requires long path of regulatory approval. Few standard bispecific antibodies (e.g. Blinatumomab, an anti CD19− and anti CD3 bispecific antibody for treatment of B cell malignancies) are available for exclusive in vivo activation of patient's own immune system for treatment of patients with B cell malignancies but they are not intended for combination therapy with activated T cells, NK cells and NKT cells or with allogeneic, or intentionally mismatched T cells, certainly not with additional immune enhancers or other anti-cancer modalities in the same complex or conjugate. Furthermore, such procedures can be effective only against cancer cells "decorated" with cancer-associated antigen against which bispecific antibody exists. In contrast, using intentionally mismatched donor lymphocytes can also eliminate cancer cells by a process of "inverse rejection" as documented in pre-clinical animal experiments (17) and in clinical practice (5, 6, 18-20). Interestingly, the allogeneic IL-2 activated NK cell-mediated anti-cancer cytotoxic capacity against cancer cells is radiation resistant, suggesting that complete prevention of GVHD-like toxicity by mismatched donor lymphocytes can be accomplished by sublethally irradiated IL-2 activated NK cells while T cells remain non-reactive by ionizing radiation (21).

Morecki et al. disclose the use of trifunctional bispecific antibodies to prevent graft versus host disease induced by allogeneic lymphocytes (22).

Morecki et al. disclose the induction of long-lasting antitumor immunity by concomitant cell therapy with allogeneic lymphocytes and trifunctional bispecific antibody (23).

Anti-host response, GVHD, remains a life-threatening complication involved with the most effective anti-cancer effects induced by durable circulation of alloreactive donor lymphocytes following SCT, especially for treatment of hematologic malignancies. Accordingly, it remains an unmet need to improve cell-mediated elimination of cancer by more effective yet safer cell-mediated immunotherapy as compared with conventional SCT. Specifically, more versatile, readily accessible, user-friendly and cost-effective personalized treatment of a broader spectrum of patients with different types of incurable cancer remains an unmet need.

SUMMARY OF THE INVENTION

The present invention provides therapeutic molecules and treatment methods for cancer and some non-malignant disorders based on combination of readily available monoclonal antibodies prepared as complexes and/or conjugates, used either alone and/or with activating cytokines and possibly also other supporting anti-cancer modalities (e.g., immune activators such as IL-2 or 4-1BB, chemotherapy or radiolabeled compounds). These complexes or conjugates are designed to target killer lymphocytes, activated T cells & NK cells, intentionally mismatched and/or patient's own, for optimal killing of existing cancer cells in parallel with induction of long-lasting anti-cancer vaccination against escaping or re-emerging cancer cells. The present invention also provides compositions comprising these molecules, optionally with killer cells (T cells, NK cells, NKT cells and/or macrophages) that may be activated ex vivo prior to cell infusion and also in vivo following cell infusion for optimal killing of existing cancer cells. In parallel, patient's own antigen presenting cells (dendritic cells and macrophages), attached via their Fc receptors to the Fc portion of the targeting antibodies, can be sensitized and induce long-lasting memory T cells that protect the patient against recurrent disease. Interestingly, the same complexes or conjugates injected into the primary cancer lesion, or easily accessible metastasis can be used for induction of anti-cancer vaccination, using an existing cancer lesion as internal, in situ, fully personalized anti-cancer vaccine. The present invention enables the use of different combinations of diverse, readily/commercially available and regulatory approved monoclonal antibodies potentially with additional activating cytokines (e.g., IL-2) or stimulatory molecules (e.g., 4-1BB, CD137), as effective tools for anti-cancer immunotherapy against a broad spectrum of malignant cells and other cellular moieties. Complexes or conjugates of monoclonal antibodies according to the present invention can bind to cancer cells or any other cells that need to be eliminated and to antigen presenting cells via F(ab')2 (variable region) or Fc (constant region) portion of each monoclonal antibody. The present invention provides for the first time, the possibility of rapid assembly and use of case-specific and disease-specific multifunctional monoclonal antibodies herein termed Immunotherapeutic Monoclonal Antibody Complexes or Conjugates (IMAC).

The invention provides, according to one aspect a multi-specific immunoglobulin complex or conjugate comprising at least two different monoclonal antibodies connected directly or through a linker, spacer or scaffold, wherein each antibody comprises two hypervariable regions (F(ab')2 domains) and a constant region (Fc domain).

An immunoglobulin complexes or conjugates are also termed throughout the application Immunotherapeutic Monoclonal Antibody Complexes or Conjugates (IMAC).

According to some embodiments, the at least two different antibodies are connected by at least one non-covalent bond.

According to some embodiments, the at least two different antibodies are connected through an Avidin-Biotin connection. According to certain embodiments, the at least two different antibodies are connected through an Avidin-Biotin connection between biotin moieties covalently coupled to the antibodies and avidin moieties.

According to some embodiments, the monoclonal antibodies are intact antibodies.

The present invention thus provides an IMAC comprising: a first intact antibody capable of binding to one or two T and/or NK cells; and a second intact antibody capable of binding to at least one antigen on a tumor cell or tumor-specific blood vessel (or any other cell or target that needs to be eliminated); and wherein said intact antibodies are coupled.

According to some embodiments, the IMAC comprises a first intact antibody capable of binding to a T cell and/or NK cells, and a second intact antibody capable of binding to at least one antigen on a tumor cell.

According to some embodiments the IMAC comprises an additional moiety capable of activating the immune system or inducing cancer cell death. According to certain exemplary embodiments, the activating moiety is IL-2 or 4-1BB (CD137).

According to some embodiments, the IMAC comprises binding regions to 2 different cell-surface antigens, namely two different antibodies each directed to a different antigen.

According to some specific embodiments, the combination of two specific target antigens is selected from the group consisting of: CD19 and CD20 in B cell malignancies; CD38 and CD138 in multiple myeloma; Her2/neu and MUC-1 in breast or ovarian cancer; and Her2/neu and GD2. Each possibility represents a separate embodiment of the invention.

According to the present invention, at least two antibodies, each directed toward a different target, are connected via at least one covalent or non-covalent bond to form an IMAC.

According to some embodiments, the additional moiety is an anti-cancer moiety selected from the group consisting of naked or liposomal cytotoxic chemotherapy; radiolabeled element or antibody; and oncolytic virus. Each possibility represents a separate embodiment of the invention.

According to some embodiments, the at least two monoclonal antibodies are connected through particles, beads or scaffolds. According to some specific embodiments the particles are nanoparticles. According to some embodiments, the nanoparticles are positively charged.

According to some embodiments, the nanoparticles are polymeric nanoparticles, metallic nanoparticles or liposomes. According to some embodiments, the nanoparticles are immunomagnetic beads.

According to some embodiments, the particles comprise biodegradable polymers.

According to some embodiments, an antibody, activating agent or an anti-cancer agent is connected to at least one of the antibodies of the IMAC or to the scaffold or particle carrying the IMAC, through a non-cleavable bond. According to other embodiments, coupling or conjugation of antibodies and/or additional moiety is via a cleavable bond.

According to some embodiments, the antibodies are connected through an Avidin-Biotin connection. According to certain embodiments, at least one biotin moiety is connected to at least one Lysine (Lys) residue of the monoclonal antibodies.

According to some embodiments, the biotin is coupled to the antibodies by a connection selected from the group consisting of amide bond, thioether bond, disulfide bond, hydrazone bond, and azido bond. According to certain embodiments, the different antibodies in the immunoglobulin complex are biotinylated using different type of connection.

Any avidin molecule or avidin derivative capable of binding non-covalently at least two biotin molecules can be used according to the present invention. According to certain embodiments, the avidin is a natural, modified or genetically produced multivalent avidin molecule. According to some embodiments, the avidin used to conjugate the biotinylated monoclonal antibodies is selected from the group consisting of egg-white avidin, streptavidin, NeutrAvidin and two affinity binding avidin molecules. Each possibility represents a separate embodiment of the invention.

According to yet other embodiments, the complex or conjugate comprising the at least two different antibodies is connected through an Avidin-Biotin connection to an additional anti-cancer molecule.

According to some embodiments, the at least one antibody, the avidin moiety or both are conjugated with a detectable probe or with a toxic moiety. According to some embodiments, the toxic moiety is selected from a chemotherapeutic agent and a radioisotope.

Any conjugate or scaffold capable of connecting at least two monoclonal antibodies can be used according to the present invention.

According to some embodiments, the complex or conjugate comprises at least one monoclonal antibody specific to a regulatory T cells or any other cell that can suppress induction of anti-cancer immunity.

According to some specific embodiments, the antibody is specific to at least one checkpoint inhibitor. According to yet other embodiments, the antibody is specific to at least one checkpoint molecule selected from the group consisting of PD-1 and CTLA-4.

According to some embodiments, at least one of the monoclonal antibodies in the IMAC is capable of binding to T cells, NK cells, dendritic cells or macrophages through a domain selected from the group consisting of an F(ab')2 (hypervariable region) domain and an Fc domain (constant region).

According to some embodiments, at least one monoclonal antibody is capable of binding, through its F(ab')2 or Fc domain, to an Fc receptor on activated immune cells selected from the group consisting of NK cells, T cells, NKT cells, macrophages and any combination thereof.

According to some embodiments, the IMAC is capable of binding to the Fc receptor of antigen presenting cells such as dendritic cells or macrophages, and to initiate induction of memory T cells responsible for long-lasting immunity against tumor and/or other antigens.

According to some embodiments, the IMAC is capable of binding to the Fc receptor of dendritic cells or macrophages through an Fc region of at least one of the intact antibodies.

According to other embodiments, the IMAC is capable of binding to the Fc receptor of dendritic cells or macrophages through an F(ab')2 domain of a monoclonal antibody.

According to some embodiments, the IMAC comprises at least one antibody selected from the group consisting of anti-CD2, anti-CD3, anti-CD4, anti-CD8, anti-CD28, anti-CD25, anti-CD80, anti-CD86, anti-CD45RA, anti-CD45RO, anti-CD134, anti-CD196, anti-CD197, anti-CD62L, anti-CD69, anti-CTLA-4, anti-PD-1 and anti-PD-L1. Each possibility represents a separate embodiment of the invention.

According to some embodiments, the IMAC comprises at least one antibody specific to dendritic cells and/or macrophages, the antibody is selected from the group consisting of anti HLA-DR, anti-CD16, anti-CD56, anti-NKG2D, anti-NKG2A, anti-CD94, anti-CD11b, anti-CD14 and anti-CD136. Each possibility represents a separate embodiment of the invention.

According to some embodiments, the IMAC comprises at least one antibody against mesenchymal stromal cell markers (MSCs), the antibody is selected from the group consisting of anti-CD73, anti-CD105, anti-CD90 and anti-CD200. Each possibility represents a separate embodiment of the invention.

According to some embodiments, at least one of the monoclonal antibodies is selective for a tumor antigen or a tumor-associated antigen or an antigen on tumor-supporting blood vessels. According to some specific embodiments, the tumor antigen or tumor-associated antigen is selected from the group consisting of anti-CD19, anti-CD20, anti-EGFR, anti-HER2, anti-GD2, anti-CD30, anti-CD37, anti-CD38 and anti-CD138. Each possibility represents a separate embodiment of the invention.

According to some embodiments, an agonistic antibody is included in the IMAC to activate the anticipated immune response or for treatment of autoimmune diseases. According to certain exemplary embodiments, the antibody is anti-CD28 or anti-4-1BB (CD137).

According to some embodiments, the IMAC comprises at least one antibody against hematopoietic stem cells for induction of myeloablation as conditioning in preparation for autologous or allogeneic stem cell transplantation (SCT). According to certain exemplary embodiments, the antibody is anti-CD34 or anti-AC133.

According to some embodiments, the IMAC comprises at least one antibody against tumor angiogenesis related antigens. According to certain exemplary embodiments, the antibody is selected from the group consisting of anti-VEGF, anti-EPCs and anti-CD31.

According to some embodiments, the IMAC comprises at least one monoclonal antibody specific for a receptor of, or protein-specific to, cancer-supporting blood vessels.

According to some embodiments, an IMAC comprises at least one monoclonal antibody specific for T cells, B cells or both is provided for induction of immunosuppression.

According to some embodiments, the immunosuppressive IMAC is for the treatment of severe autoimmune diseases.

Any type of antibody can be used in the IMAC of the invention as long as it contains an Fc domain (constant region) and at least two F(ab')2 binding domain (hypervariable regions).

According to some embodiments, the antibodies of the IMAC are monoclonal antibodies.

According to some embodiments, the IMAC comprises at least one antibody selected from the group consisting of non-human, chimeric, humanized, human antibody, and any combination thereof.

According to another aspect, an IMAC is provided for treating cancer.

According to some embodiments, the IMAC is for use in elimination or inhibition of cancer progression, metastatic spread, and/or for vaccination against cancer.

According to other embodiments, the IMAC is for elimination or blocking a disease-causing cell or an infectious agent.

The present invention provides, according to yet another aspect, a pharmaceutical composition comprising at least one IMAC described above, and a pharmaceutically acceptable carrier, diluent or excipient.

According to some embodiments the pharmaceutical composition comprises at least one IMAC composed of at least two different monoclonal antibodies connected by an avidin-biotin binding.

According to some embodiments, the pharmaceutical composition comprises an IMAC composed of at least two different monoclonal antibodies conjugated to nanoparticles. According to certain embodiments, the nanoparticles are biodegradable and/or magnetic beads.

According to some embodiments, the pharmaceutical composition further comprises lymphocytes.

According to some embodiments, the lymphocytes are allogenic, namely from a mismatched donor, with respect to the lymphocytes of the subject in need of the treatment. According to some embodiments, the lymphocytes are haploidentical with respect to the lymphocytes of the subject in need of the treatment. According to certain embodiments, the lymphocytes are autologous with respect to the lymphocytes of the subject in need of the treatment.

According to some embodiments, the pharmaceutical composition comprises an additional therapeutic agent. Any agent that is used against cancer, cancer progression or cancer spread may be contained in the pharmaceutical compositions of the present invention.

According to some embodiments, the pharmaceutical composition is administered in combination with a treatment with another anti-cancer or anti-angiogenic agent.

According to some embodiments, the pharmaceutical composition is used as adjunct therapy to allogenic or autologous cell therapy, in preparation for autologous or allogeneic stem cell transplantation in a cancer patient or any patient in need of stem cell transplantation for acquired or congenital disorder to prevent rejection or to induce therapeutic myeloablative treatment.

According to some embodiments, the pharmaceutical composition is administered to a patient prior to, concomitantly with or after allogeneic SCT to eliminate minimal residual disease or for treatment of GVHD by elimination of alloreactive donor T lymphocytes.

According to some embodiments, the pharmaceutical composition is for use in combination with donor T cell therapy, said donor T cells are obtained from partially mismatched or fully mismatched donors.

According to other embodiments, the donor T cells are activated in vitro prior to infusion into the patient.

According to some embodiments, the T cells are activated by pretreatment with an agent selected from the group consisting of IL-2, phytohemagglutinin (PHA), α-GalactosylCeramide (KRN7000), and any combination thereof.

According to certain embodiments, the T cells are activated by pretreatment with IL-2. According to certain embodiments, the T cells are activated by pretreatment with phytohemagglutinin (PHA). According to certain embodiments, the cells are activated by pretreatment with α-GalactosylCeramide (KRN7000). According to certain exemplary embodiments, the cells are activated by pretreatment with IL-2, phytohemagglutinin (PHA) and α-GalactosylCeramide (KRN7000).

According to some embodiments, the IMAC further comprises an agonistic monoclonal antibody, an activating agent or an oncolytic virus. According to certain embodiments, the activating agent is IL-2 or 4-1BB. According to certain exemplary embodiments, the oncolytic virus is Newcastle disease virus (NDV). According to some embodiments, agonistic monoclonal antibody and/or activating agent is biotinylated.

According to certain embodiments, the pharmaceutical composition comprises at least two IMAC molecules and an activating moiety wherein said IMAC is capable of binding to the Fc receptor of antigen presenting cells, dendritic cells or macrophages. According to some embodiments, the activating moiety is part of an IMAC.

The present invention provides, according to yet a further aspect, a vaccine composition comprising an immunoglobulin complex or conjugate of at least two different intact monoclonal antibodies connected to form an IMAC.

According to some embodiments, the vaccine composition is an anti-cancer vaccine.

According to some embodiments, the anti-cancer vaccine is for direct injection into primary tumor or tumor metastatic lesion, using the malignant tissue itself as an in vivo anti-cancer vaccine, for induction of systemic anti-cancer effects known as abscopal effect. According to certain embodiments, the anti-cancer vaccine is used alone or in conjunction with external involved field radiation or in situ radioactive compound.

According to some embodiments, the vaccine composition comprises at least one IMAC that comprises least two biotinylated monoclonal antibodies conjugated via binding to tetrameric avidin.

According to some embodiments, the vaccine composition comprises at least one IMAC that comprises two monoclonal antibodies conjugated to nanoparticles, such as immunomagnetic beads and/or biodegradable beads.

Any agent that is used to prevent cancer recurrence, cancer progression or cancer spread may be contained in the vaccine compositions of the present invention.

The present invention provides according to another aspect a method for treating a subject having cancer, the method comprising selecting a combination of at least two antibodies suitable for treatment of the subject, creating an immunoglobulin complex or conjugate by connecting the at least two antibodies, and administering to the subject a pharmaceutical composition comprising the immunoglobulin complex or conjugate.

According to some embodiments, the method comprises administering to a subject having cancer two different IMAC molecules, each targeting more than one cancer antigen and each targeting cancer cells with different killer cells.

According to certain embodiments, the method comprising administering a therapeutic combination that targets at least one of Her2/neu, GD2 and EGFR, at least one of CD3, CD28, CD4, CD8 and NK's CD16 or CD56 antibodies or IMAC against antigen presenting cells.

The methods of the present invention include stand-alone treatments as well as combination with any anti-cancer or anti-angiogenic treatment.

According to a specific embodiment, the method comprises administration of a pharmaceutical composition comprising at least one IMAC to a subject in need thereof, and administration of at least one anti-cancer or anti-angiogenic agent.

The administration of the IMAC and the anti-cancer or anti-angiogenesis agent is performed together with the additional agent according to some embodiments or separately according to other embodiments. According to some embodiments, the additional agent is administered at a separate time from the immunoglobulin complex or conjugate of the invention.

According to some embodiments, the method further comprises a myeloablative treatment by IMAC against malignant or genetically abnormal hematopoietic stem cells replacing the need for myeloablative treatment with chemotherapy and/or whole-body radiation prior to allogenic stem cell transplantation for malignant or non-malignant indication, respectively.

According to some embodiments, the method comprises administration of the immunoglobulin complex or conjugate against residual malignant cells following conventional anti-cancer modalities or after autologous or allogeneic stem cell transplantation.

According to some embodiments, the method further comprises donor derived T cell therapy wherein donor T cells are obtained from partially mismatched or fully mismatched donors and wherein donor T cells are optionally activated ex vivo prior to infusion into the patient or activated in vivo after transplantation.

According to some embodiments, said activation is performed by incubation ex vivo with an activating cytokine or by later administration of the cytokine to the treated patient. According to exemplary embodiments, the cytokine is selected from the group consisting of IL-2, IL-12, IL-15, IL-7, and any combination thereof. According to certain embodiments, the cytokine is IL-2.

According to some embodiments, the activation is performed by incubation ex vivo with IL-2, phytohemagglutinin (PHA), α-GalactosylCeramide (KRN7000), or any combinations thereof.

According to some embodiments, the method further comprises administering to the subject lymphocytes comprising T cells, NK cells and/or NKT cells.

According to some embodiments, the lymphocytes are activated autologous, or activated allogenic, namely from an HLA matched or intentionally mismatched donor.

According to a specific embodiment, the lymphocytes are haploidentical to the subject or unrelated and fully mismatched readily available "off-the-shelf".

Any tumor characterized by expressing a specific tumor antigen or tumor-associated antigen may be treatable with the immunoglobulin complexes or conjugates of the present invention.

According to some embodiments, the cancer is selected from hematologic malignancy and solid tumor.

According to some embodiments, the solid tumor is a metastatic solid tumor.

According to some specific embodiments, the hematologic malignancy is selected from the group consisting of acute leukemia, chronic leukemia, non-Hodgkin lymphoma (NHL), Hodgkin lymphoma (HL), myelodysplastic syndrome and multiple myeloma.

According to some embodiments, the solid tumor is a primary resistant solid tumor or tumor metastases. According to certain exemplary embodiments, the tumor is brain glioma.

According to some embodiments, the tumor or its supporting blood vessels express the protein VEGF and the IMAC comprises at least one antibody that specifically recognizes this protein. According to some embodiments, the VEGF is VEGF-A.

According to some specific embodiments, the VEGF-expressing tumor is selected from the group consisting of melanoma, colon cancer, gastric cancer, esophageal cancer, lung cancer, breast cancer, ovarian cancer, pancreatic cancer, cholangiocarcinoma, hepatoma, sarcoma, renal cell carcinoma, prostate cancer and brain glioma. According to certain exemplary embodiments, the brain glioma is glioblastoma, astrocytoma or diffuse intrinsic pontine glioma.

According to some embodiments, the method of treating a subject having cancer further comprises administering to the subject a biotinylated antibody, radiolabeled antibody or anti-cancer compound in addition to the IMAC and immune activating agent, aiming to kill malignant cells by combination of cell-mediated cytotoxicity and radiation-induced irreversible double-stranded DNA break, combined with induction of long-lasting anti-cancer immunity.

According to some embodiments, the anti-cancer compound is a radiolabeled anti-cancer antibody.

According to some embodiments, the anti-cancer compound is somatostatin.

According to a yet further aspect, the present invention provides a method of immunotherapy of cancer comprising administering an immunoglobulin complex or conjugate that blocks negative regulators such as checkpoint inhibitors or regulatory T cell inhibitors.

According to some embodiments, the checkpoint inhibitor is selected from the group consisting of CTLA-4, PD-1/PD-L1 and CEACAM1.

According to some specific embodiments, the cancer treatable with IMAC targeting a negative regulator is selected from the group consisting of melanoma, colon cancer, gastric cancer, esophageal cancer, lung cancer, breast cancer, ovarian cancer, pancreatic cancer, cholangiocarcinoma, hepatoma, sarcoma, brain glioma, renal cell carcinoma, prostate cancer and brain glioma. According to certain embodiments, the brain glioma is glioblastoma, astrocytoma or diffuse intrinsic pontine glioma.

According to some embodiments, cancer cells of the treated subject or lysates of cancer cells, obtained by cryopreservation following surgery or obtained by biopsy, are mixed in vitro with the IMAC, thereby enhancing its immunogenic activity for induction of anti-cancer vaccination in vivo.

According to some embodiments, the method comprises injection of the IMAC proximally to the draining lymph nodes. According to some embodiments, sensitization of patient's T cells is performed by concomitant injection of GM-CSF systemically or proximally to the draining lymph nodes.

According to some embodiments, the IMAC is administered intravenously or inside a tumor or tumor metastases. According to some specific embodiments, the IMAC is administered directly to the tumor draining lymph nodes. As such, the present invention also provides the use of the IMAC for vaccination against cancer, even if no cancer cells are available for preparation of tumor cell lysates for preparation of anti-cancer vaccine.

According to some embodiments, the method comprises concomitant activation of antigen presenting cells, dendritic cells and/or macrophages, by administration of GM-CSF that activates and enhance proliferation of patient's own dendritic cells and macrophages.

According to some embodiments, the pharmaceutical composition described herein is administered as part of a regiment of cancer treatment selected from the group consisting of chemotherapy, immunotherapy, biotherapy, hormonal therapy, radiation therapy, bone-marrow transplantation, surgery, and any combination thereof.

According to some embodiments, the method of treating cancer comprises administering to a subject in need thereof a composition comprising at least one IMAC and activating the immune system of the subject in vivo. According to certain embodiments, the administering of IMAC is in parallel with continuously activating the immune system of the subject in vivo.

According to some embodiments, the method further comprises administering to said subject donor lymphocytes that may be activated prior to infusion, after cell infusion or both.

According to some embodiments, the anti-cancer cytotoxicity is mediated by T cells, NK cells and NKT cells together, or by NK cells alone to minimize cytokine release syndrome (CRS), that may be caused by T cells.

According to some embodiments, induction of cytolysis by biotinylated monoclonal antibodies targeting intentionally mismatched cytokine activated donor killer lymphocytes (T, NK & NKT cells) injected intravenously inside the cancer tissue result in induction of immunity against untreated remote metastases (abscopal effect).

The present invention provides, according to yet another aspect, a method of vaccination and induction of long-lasting anti-cancer immunity, the method comprising an intra-tumor injection of avidin, optionally using ultrasound or computerized tomography (CT) guided needle, followed by intravenous administering biotinylated monoclonal antibodies together with intentionally mismatched cytokine activated donor killer lymphocytes.

According to some embodiments, the killer lymphocytes are T cells, NK cells, NKT cells or combination thereof.

According to some embodiments, the method comprises direct (intratumor) injection of avidin into the primary tumor or visible metastatic lesion, followed by injection of biotinylated monoclonal antibodies alone or with at least one additional biotinylated immune activating agent or an anti-cancer modality. According to certain exemplary embodiments, the immune activating agent is IL-2 or 4-1BB. According to certain exemplary embodiments, the anti-cancer modality is chemotherapy, radiolabeled molecule or biotinylated oncolytic virus. According to some embodiments, the intratumor injection is performed using ultrasound or CF guided needle. According to some embodiments, the method further comprises administration of an activating molecule.

According to an additional aspect the present invention provides a method of preparing an anti-cancer vaccine from a fresh or cryopreserved tumor tissue by mixing cells or lysate with a composition comprising at least one IMAC, wherein said at least one IMAC comprises at least one monoclonal antibody that recognizes a tumor antigen and/or at least one monoclonal antibody that binds to patient's own T cells or NK cells with Fc portion of such antibodies targeting patient's dendritic cells and/or macrophages in vivo.

According to some embodiments, the cells or lysate are obtained at diagnosis or by a biopsy, According to certain embodiments, the cryopreserved tumor tissue is irradiated, or fresh cells or lysates.

According to some embodiments, the method is for vaccination of a subject having cancer with no known cancer-associated antigen. According to certain exemplary embodiments, the method comprises injection of cancer cells, together with IMAC containing anti-T cells and anti-NK cells antibodies. The method is for attracting patient's own T cells, NK cells and antigen presenting cells to the lymphatic system, where optimal anti-cancer vaccination can occur.

According to some embodiments, the vaccination method comprises injecting the complex or conjugate inside or proximally to the draining lymph nodes. According to some embodiments, sensitization of patients T cells is performed by concomitant injection of GM-CSF.

According to some embodiments, the avidin-biotin based IMAC is directly injected into a visible cancer tissue, primary cancer or cancer metastasis, supported by concomitant injection of GM-CSF.

According to some embodiments, the method of vaccinating a subject in need thereof, against cancer, comprises administering at least one IMAC described herein and at least one agonistic antibody. According to certain exemplary embodiments, the agonist antibody is anti-OX40. According to some embodiments, the method further comprises administering of additional monoclonal antibody that can bind to dendritic cells and/or macrophages following administration of IMAC. According to some embodiments the method results in induction of anti-cancer immunity against cancer metastatic lesion depleted of suppressive cells of the tumor microenvironment. In some embodiments, the suppressive cells are regulatory T cells, checkpoint inhibitors, tumor associated macrophages and/or mesenchymal stromal cells.

According to some embodiments of the treatment methods, the IMAC is administered intravenously, subcutaneously, intradermally or directly into primary or secondary cancer lesions. According to some specific embodiments, the IMAC used for anti-cancer vaccination is administered inside or proximally to the draining lymph nodes of the tumor, or to the axillary or inguinal lymph nodes.

According to another aspect, the present invention provides a method of treating an infection and/or infectious disease, comprising administering to a subject in need thereof an immunoglobulin complex or conjugate comprising at least one antibody capable of binding an antigen on the infected cell or infectious agent and one antibody against T cells or NK cells. According to certain embodiments, the method is for elimination of the infectious agent and/or for induction of long-lasting immunity against that infectious agent.

According to some embodiments, the complexes and conjugates, and specifically the IMAC molecules described herein are for use in eradiation of undesirable malignant and/or normal bone marrow hematopoietic stem cells for immune-mediated myeloablative conditioning in preparation for allogeneic or autologous stem cell transplantation for treatment of malignant hematologic disorders, genetic diseases and for elimination of self-reactive lymphocytes in autoimmune diseases, respectively.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

It is to be understood that any combination of each of the aspects and the embodiments disclosed herein is explicitly encompassed within the disclosure of the present invention.

Other objects, features and advantages of the present invention will become clear from the following description and drawings.

BRIEF DESCRIPTION OF THE DRAWINGS

FIGS. 2A-2C. A schematic step-by-step representation of the anti-cancer activity of immunotherapeutic monoclonal antibody anticancer complexes or conjugates (IMAC) mediated by mismatched donor lymphocytes (marked as dark cytoplasm), followed by induction of specific anti-cancer immunity by patient's own lymphocytes following rejection of mismatched donor lymphocytes. FIG. 2A—IMAC structure and binding to mismatched donor lymphocytes (including pre-activated T, NK and NKT cells). FIG. 2B—IMAC bound to pre-activated mismatched donor lymphocytes induces fast and most effective anti-cancer effects against any MHC mismatched target cells including multi-drug resistant cancer cells and even cancer stem cells. Donor's anti-cancer effector cells can be also continuously activated in vivo following cell infusion with IL-2 or other immune system activators to maximize their cytotoxic anti-cancer effects while they last, until rejection. After rejection of mismatched donor lymphocytes, IMAC still persist and can bind patient's immune system cells. FIG. 2C—Following rejection of mismatched donor lymphocytes patient's own immune system cells (T cells binding to anti-CD3, anti-CD28 or any other T cell antibody) and patient's antigen presenting cells (dendritic cells and macrophages) bind to IMAC. Antigen presenting cells process cancer antigens in situ, sensitize patient's helper T cells and generate memory T cells against cancer antigens, thus resulting in long-lasting anti-cancer immunity.

FIG. 3A—Biotinylated monoclonal antibodies linked to avidin bind to activated mismatched T, NK & NKT cells. FIG. 3B—Targeted cancer cytotoxicity mediated by simultaneous attack of mismatched activated T, NK & NKT cells complexed by avidin. FIG. 3C—Following rejection of mismatched donor lymphocytes monoclonal antibody complexes bind to residual cancer lysates or residual cells and to patient's T & NK cells and antigen presenting cells. FIG. 3D— Pulsed dendritic cells and macrophages sensitize helper T cells, induce cytotoxic T cells and memory T cells, eliminate residual cancer cells and memory cells establish long lasting immunity against recurrent disease. FIG. 3E—The process of induction of anti-cancer immune responses and generation of long-lasting memory T cells can last as long as tumor antigens and monoclonal antibody complex exist.

FIG. 4A—Intratumor injection of avidin alone into a visible cancer metastatic lesion by CT or ultrasound guided needle. FIG. 4B—Binding pre-activated donor T cells, NK cells & NKT cells to biotinylated monoclonal antibodies against T cells and cancer cells. Other biotinylated anti-cancer agents may also be used to be attached to cancer cells via avidin. FIG. 4C—Intravenous infusion of pre-activated donor T cells, NK cells & NKT cells to biotinylated monoclonal antibodies against T cells and cancer cells. Due to strong binding affinity of biotin to avidin, killer cells will be selectively targeted to avidin located inside tumor tissue and result in immediate direct in situ anti-cancer cytotoxicity. FIG. 4D—Following rejection of mismatched donor lymphocytes, IMAC's monoclonal antibodies bind to patient's own T cells and antigen presenting cells resulting in pulsing of dendritic cells & macrophages, sensitization of patient's T cells, and induction of cytotoxic and memory T cells. The end result is induction of long-lasting systemic anti-cancer immunity against residual cancer cells or recurrent disease.

FIG. 5A—Cytotoxicity of multiple myeloma (RPMI8226) cells after incubation for 24 hours with IL-2-activated peripheral blood mononuclear cells, containing activated NK & T cells alone, or following targeting activated lymphocytes with biotinylated monoclonal antibodies against CD38, CD3, CD4 and CD8 complexed to avidin at an effector:target cell ratio of 1:1 against CD38+CD20-myeloma cells. In the grey column anti-myeloma cytotoxicity was done using non-specific anti-CD20 antibodies instead of anti-CD38 antibodies confirming preferential killing following specific myeloma targeting of IMAC. Results represent means±SEM of wells in each group ($p<0.01$ according to T-test). FIG. 5B—Cytotoxicity of lymphoma (Ramos) cells after incubation for 24 hours with IL-2-activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratio of 1:1 against CD20+ cancer cells. Results represent means±SEM of wells in each group (*$p<0.001$ according to t-Test).

FIG. 16. Optimizing pre-treatment in vitro proliferation of different subsets of donor lymphocytes in order to maximize the capacity of all possible killer cells to induce anti-cancer cytotoxicity. Donor lymphocytes were precultured for 6 days with interleukin 2 (IL-2) alone, phytohemagglutinin (PHA) alone, α-GalactosylCeramide (KRN7000) alone, KRN7000+PHA, IL-2+KRN7000, IL-2+PHA and IL-2+KRN7000+PHA in comparison with untreated PBMC.

DETAILED DESCRIPTION OF THE INVENTION

Figure 1A:
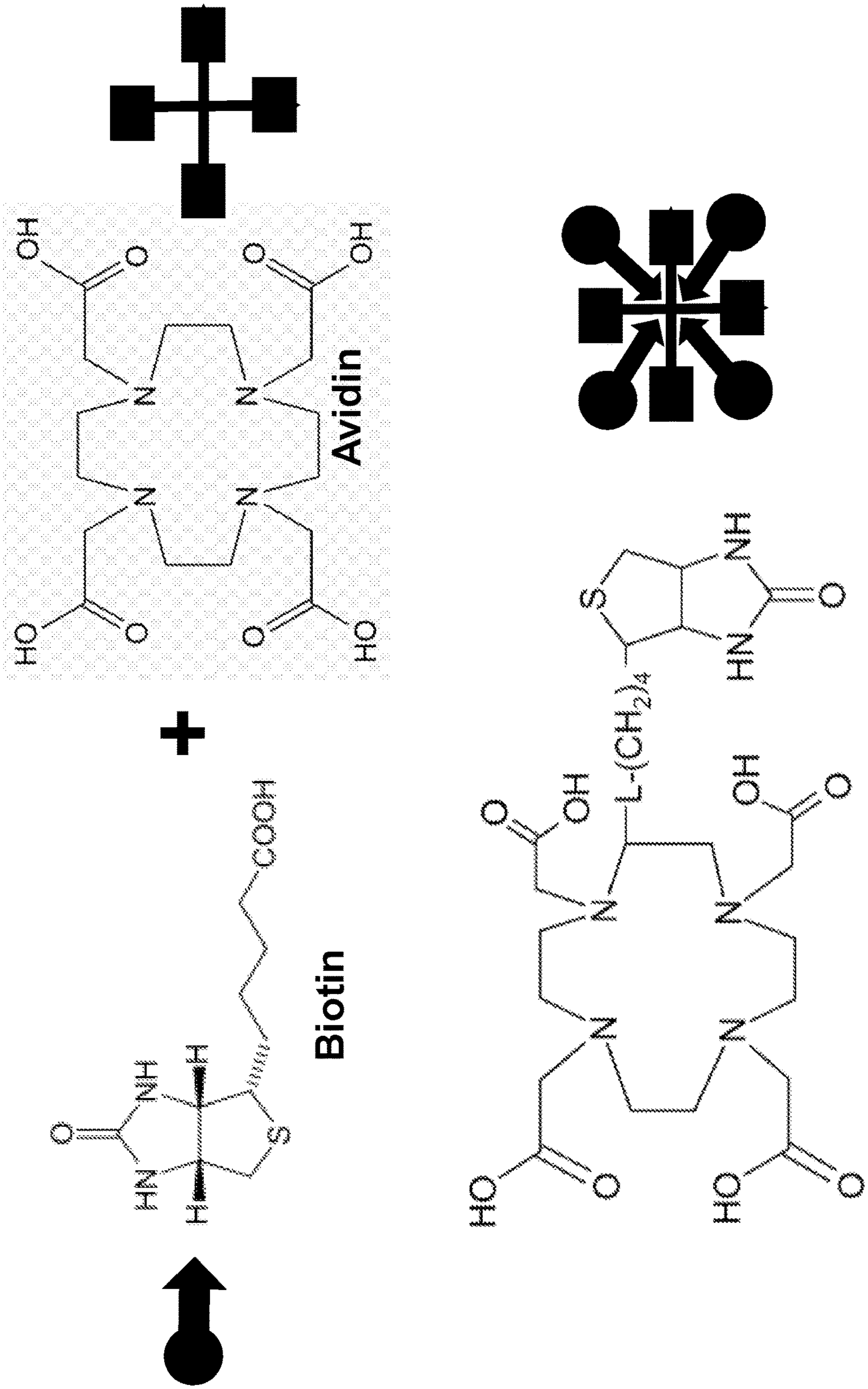
FIGS. 1A-1C describe schematically the basic structures of tetrameric Avidin and Biotin-bound antibodies according to some embodiments of the invention. For the sake of simplicity, the figures show binding of two biotinylated monoclonal antibodies (e.g., in FIG. 1C), but the use of avidin as shown in FIG. 1B, enables a simultaneously binding of four different monoclonal antibodies or other anti-cancer agents. One tetrameric avidin molecule can connect by strong non-covalent bonds, four biotin-containing molecules (or only 2 binding sites for dual-affinity biotin) such biotinylated antibodies to form a therapeutic avidin-biotin complex for targeting different cells and in situ activating molecules to cancer cells or to antigen presenting cells. The schema presents several optional antibodies that may be used. Cytokines such as IL-2, 4-1BB or other biotinylated anti-cancer modalities or agonistic antibodies may also be connected through the avidin-biotin connection.

The present invention provides molecules, compositions and methods for immunotherapy, in particular against all MHC incompatible cancer cells, including multi-drug resistant and cancer stem cells. The present invention provides methods and compositions for direct elimination of cancer cells combined with induction of anti-cancer vaccination, by a 2-stage procedure, first selective targeting of mismatched killer cells against cancer cells followed by induction of anti-cancer immunity by patient's own antigen presenting cells and T cells using multi-specific combinations of complexes or conjugates of antibodies termed IMAC. The IMAC may consist of avidin's high affinity binding of four biotinylated antibodies and/or other potential biotinylated anti-cancer agents, or only dual binding of monoclonal anti-T cell antibody and anti-cancer antibody complex or conjugate, or even two monoclonal antibodies connected with beads or biotin-binding beads.

In accordance with the invention the targeted cells include activated allogeneic donor lymphocytes, haploidentical or unrelated fully mismatched "off-the-shelf" activated killer cells including T cells, NK cells (not excluding NKT cells) as killers of targeted cancer cells. Activation of anti-cancer effector cells can be accomplished by cytokine activation ex vivo prior to cell infusion, followed by continuous in vivo activation of killer cells while they last until being rejected using low dose IL-2 or other cytokines to maximize anti-cancer activity for a few more days until being rejected.

The antibodies included in the complexes and conjugates of the invention are directed against all killer cells (T cells, NK cells and NKT cells) while recruiting antigen presenting cells (dendritic cells and macrophages) via F(ab')2 or Fc domains. IMAC is applied to target cancer-specific or cancer-associated cell-surface antigens, or for elimination of any other undesirable cells or infectious pathogen, depending on the type of clinical condition that needs to be treated.

Any anti-cancer antibody, anti-angiogenic antibody, antibody that can activate the immune system of the patient, or down-regulate suppressor cells, antibody that subject cancer cells to the immune system by elimination of protective cancer's microenvironment (e.g. MSCs and antibodies against adhesion receptors and chemokine receptors), or antibody against any cancer associated target known in the art, can be used in the IMAC of the invention, including commercially available antibodies or new monoclonal antibodies that are currently under development.

The connection of the antibodies may be performed by any means known in the art, for example, by using avidin-biotin non-covalent binding, or by linkers forming covalent or non-covalent binding. The antibodies may be also conjugated using nanoparticles which may be biodegradable, magnetic and/or positively charged and/or comprise additional targeting, binding or activating moieties to improve anti-cancer potential as long as both monoclonal antibodies will jointly and simultaneously target cancer cells.

The biotin may be coupled to the antibodies by any connection known in the art, including but not limited to amide bond, thioether bond, disulfide bond, hydrazone bond, and azido bond. Different antibodies in the immunoglobulin complex may be biotinylated using different connection methods.

Any avidin molecule or avidin derivative capable of binding non-covalently at least two biotins, preferably four biotin binding sites, can be used according to the present invention. This includes natural, modified or genetically produced multivalent avidin molecule. According to some embodiments, the avidin used to conjugate the biotinylated monoclonal antibodies is selected from the group consisting of egg-white avidin, streptavidin and NeutrAvidin (a deglycosylated version of avidin or even dual affinity avidin).

The dissociation constant of avidin-biotin is in the range of $10^{-15}$M. As such it forms exceedingly strong non-covalent bonds. The avidin molecule has four binding sites thereby it is capable of binding together up to four biotinylated antibodies. Any side chain or free group on the antibody may be used to bind a biotin moiety using any method known in the art. According to some embodiments, antibodies are readily biotinylated via their lysine molecules. The number of biotin molecules on each of the labeled antibodies is carefully monitored in order to avoid excess biotinylation that may harm the antibody's binding activity.

Complexation of different biotinylated monoclonal antibodies may be accomplished by non-covalent binding to avidin (NeutrAvidin and streptavidin), a molecule that can bind 4 similar or different biotinylated monoclonal antibodies. The clinical use of avidin-biotin complexes is not toxic and already approved for different indications, especially for cancer diagnostic and therapy with radiolabeled antibodies (24). Complexes of monoclonal antibodies are also available with biodegradable, nanoparticles such as immunomagnetic beads.

Immunotherapeutic Monoclonal Antibody Complexes according to the present invention may be created together with nanoparticles as carriers. Such nanoparticles may be biodegradable polymeric scaffolds and/or immunomagnetic beads. Commercially available nanoparticle immunomagnetic beads connected to monoclonal antibodies, that are approved for intravenous use, may be also used according to the present invention. As such, the binding of the monoclonal antibodies to the tumor could be induced by non-covalent binding of two or more monoclonal antibodies to the beads.

According to some embodiments, antibody complexes comprising magnetic beads are used to select only activated NK cells and therefore eliminate or avoid any potential risk of cytokine release syndrome mediated primarily by T cells.

According to some embodiments, the nanoparticles or beads used to complex the antibodies are positively charged in order to better attract to negatively charged cancer cells.

The IMAC comprises for example 2 to 4 biotinylated monoclonal antibodies, or 3 biotinylated monoclonal antibodies and one additional biotinylated anti-cancer agent, some directed against antigens expressed on the malignant cells (or any other cell or infectious agent that needs to be eliminated) and some against effector cells of the immune system or antigen presenting cells (T cells, NK cells, NKT cells, dendritic cells & macrophages), complexed via an avidin moiety. The different antibodies are complexed non-covalently by Biotin-Avidin (NeutrAvidin or StreptAvidin) linkage or otherwise conjugated covalently. The antibodies may be also conjugated with microparticles such as beads that may be according to some embodiments, biodegradable and/or magnetic. In addition to monoclonal antibodies, avidin can be used to bind other biotinylated compounds that can amplify the efficacy of anti-cancer immunotherapy (e.g., biotinylated IL-2 or 4-1BB, etc.) or even biotinylated chemotherapy molecules or radioactive isotopes or oncolytic virus, etc.

According to some embodiments, IMAC can be constructed using chemical linkers that can bind at least two monoclonal antibodies and optionally an anti-cancer agent and/or an immuno-activator (e.g., cytotoxic, radioactive, immune activators such as IL-2 or 4-1BB, etc.).

IMAC can be used primarily for immunotherapy against cancer by combining eradication of cancer cells including cancer stem cells resistant to available anti-cancer modalities by activated mismatched donor lymphocytes, however, due to in vivo activation of donor lymphocytes with IL-2, also patient's own immune system cells may be activated and add to induction of anti-cancer immunity followed by induction of anti-cancer vaccination by patient's long-lasting memory T cells. Cancer Immunotherapy with IMAC is mediated by the capacity of IMAC to bind killer cells and/or antigen presenting cells via F(ab')2 or Fc portion of each of the monoclonal antibodies complexed in the IMAC to activate autologous, haploidentical or unrelated "off-the-shelf" intentionally mismatched unrelated lymphocytes (T cells, NK cells & NKT cells). Killing of otherwise resistant malignant cells, including cancer stem cells that are a priori resistant to all available anti-cancer modalities, can be accomplished by mismatched activated donor lymphocytes that induce effective anti-cancer effects based on the most effective mechanism of rejection of any MHC mismatched target cells that starts immediately following infusion and lasts until mandatory rejection of intentionally mismatched donor lymphocytes. In contrast, immunotherapy with IMAC based activation of patient's own immune system cells as long as IMAC persists results in induction of anti-cancer immunity and memory T cells that are not expected to be rejected.

Killing of cancer cells can also be accomplished using IMAC that consists of radiolabeled biotinylated monoclonal antibodies or biotinylated antibodies anti-cancer chemotherapeutic agents complexed with avidin too. The therapeutic use of avidin is not hampered by anti-avidin antibodies thus encouraging its further use for different clinical indications (25). For example, using radiolabeled somatostatin analogues or radiolabeled biotin complexed with other biotinylated monoclonal antibodies with avidin can be used for treatment of neuroendocrine pancreatic cancer (26). For example, $^{90}$Y-labelled biotin can be targeted to breast cancer cells by conjugation with biotinylated monoclonal antibodies against Her2/neu and also additional antibodies to target breast cancer and antigen presenting cells that can be triggered by cancer antigens released in the process of cytotoxicity (27). As such, in parallel with elimination of breast cancer metastases, as one example, anti-cancer immunity can also be established against residual or recurrent disease. Alternatively, antibodies complexed with biodegradable and/or immunomagnetic nanoparticles can be used, wherein such nanoparticles are optionally positively charged and/or include other anti-cancer properties.

Since induction of long-lasting anti-cancer immunity that can control residual malignant cells or recurrent disease is established by treatment with IMAC, the method can be used for intentional induction of anti-cancer immunity instead of the conventional preparation of dendritic cells pulsed with cancer antigens that may not be available, as diagrammatically described in FIG. 3.

Binding of IMAC complex using avidin, can also result in selective and more effective anti-cancer immunotherapy by elimination of inhibitory cells (regulatory T cells, checkpoint inhibitors, myeloid-derived suppressor cells and mesenchymal stromal cells) that can impair development of effective anti-cancer immunotherapy on the one hand, and protect the microenvironment of cancer metastases from an attack by the immune system, in parallel with induction of anti-cancer effects.

As such, antibody-complexes or antibody-conjugates according to the present invention may be designed to target not only cancer cells but also other undesired cells such as cancer-supporting blood vessels in addition to cells involved in suppressive microenvironment (e.g., regulatory T cells, checkpoint inhibitors, myeloid-derived suppressor cells, tumor associated macrophages and mesenchymal stromal cells that convey resistance at the tumor microenvironment).

In addition to treatment of cancer, IMAC according to the present invention may also be utilized for treatment of non-malignant indications, e.g. for elimination of normal hematopoietic cells as part of the conditioning in preparation for autologous or allogeneic stem cell transplantation for treatment malignant and non-malignant diseases (e.g. autoimmune diseases, etc.) and also for elimination of undesirable genetically abnormal bone marrow stem cells in preparation for allogeneic stem cell transplantation for genetic diseases using monoclonal antibodies against hematopoietic stem cells (e.g., anti-CD34 or CD133). Accordingly, IMAC could be used for elimination of normal hematopoietic stem cells (using for example biotinylated monoclonal anti-CD34 or anti-AC133), to induce bone marrow myeloablation, thus replacing the need for hazardous myeloablative chemotherapy and/or total body irradiation, or using anti-lymphocyte antibodies to eliminate transiently patient's immune system indicated in preparation for stem cell transplantation for treatment of hematologic malignancies, or for induction of mixed chimerism aiming for induction of transplantation tolerance for safer durable organ transplantation while avoiding the use of life-long immunosuppressive treatment to prevent allograft rejection.

In principle, IMAC could also potentially be used for elimination of infectious pathogens or cells infected with infectious agents using relevant antibodies (e.g., anti-HIV antibodies).

In addition to systemic administration, IMAC can also be injected into the primary tumor that cannot be surgically removed or into any visible easily accessible tumor metastasis alone or in combination with additional agents that can amplify anti-cancer immunity to induce local anti-cancer cytotoxicity followed by systemic anti-cancer vaccination against remote metastases, inducing the so called abscopal effect as featured in FIGS. 3 and 4. As such, using IMAC for anti-cancer vaccination provides a practical approach for using an existing inoperable primary cancer or visible cancer metastatic lesion as in situ internal anti-cancer vaccine. Theoretically, this may represent the best possible personalized anti-cancer vaccine that can be effective even if the exact phenotype of the cancer cells is unknown. Once in situ sensitization occurs against cancer antigens, systemic immune response may react against remote metastases (abscopal effect).

The present invention also provides the possibility of rapid design and manufacture of personalized anti-cancer agents against a broad spectrum of clinical indications at the patient's bedside using off-the-shelf activated donor lymphocytes and off-the-shelf panel of biotinylated monoclonal antibodies. The use of avidin based IMAC, readily available activated donor lymphocytes and relevant biotinylated antibodies, allow to prepare suitable anti-cancer treatment a soon as indicated with no technical delay.

According to some embodiments, commercial immunomagnetic beads (approved for injection in vivo) used for positive or negative selection of cells, conjugated with relevant monoclonal antibodies against any desirable cell of the immune system, can be also connected covalently or non-covalently with more than one antibody to form IMAC and used for cancer immunotherapy.

According to certain embodiments, the immunomagnetic beads are selected from the group consisting of anti-biotin microbeads, immunomagnetic beads, CliniMACS CD1c (BDCA-1), CliniMACS CD4, CliniMACS CD8, CliniMACS CD14, CliniMACS CD25, CliniMACS CD34, CliniMACS CD56, CliniMACS CD133 and CliniMACS CD304 (BDCA-4).

Subcutaneous injection of low dose IL-2 may be sufficient for continuous activation of mismatched donor lymphocytes in vivo following infusion. Higher doses of IL-2 can also be used when attempting activation of patient's own lymphocytes that may be activated together with IMAC application.

In a preferred embodiment, IL-2 (or another activating cytokine or agent), can also be administered prior to administration of the IMAC when using freshly obtained unmanipulated donor lymphocytes, MHC identical, haploidentical or unrelated and fully mismatched for treatment of patients in centers where the use of in vitro processed lymphocytes is unapproved, being considered advanced therapeutic medicinal product (ATMP), in order to induce in vivo activation of allogeneic anti-cancer effector cells in case it is mandatory to avoid the use of a procedure considered ATMP.

Although the use of IMAC is primarily designed to eliminate resistant cancer cells and induce long-lasting anti-cancer immunity, the principles behind the IMAC invention can also be used as anti-cancer vaccine as shown diagrammatically in FIGS. 3 and 4. Maximizing the anticipated anti-cancer vaccination may be accomplished by additional activation of antigen presenting cells that can be accomplished by GM-CSF (Leukine) injection subcutaneously or proximally to draining lymph nodes.

The therapeutic effects of IMAC may be further enhanced by using IMAC after systemic down-regulation of all known inhibitors of the immune responses such as regulatory T cells, CTLA-4, PD-1/PDL-1, myeloid-derived suppressor cells (MDSC), mesenchymal stem cells (MSC) inflammatory cytokines. Alternatively, IMAC may be used for suppression of checkpoint inhibitors (e.g. using biotinylated ipilimumab and nivolumab or pembrolizumab), or against MSCs (e.g. biotinylated monoclonal antibodies against CD90, CD73, or CD 105) or against MDSC (e.g. against CD14).

According to yet additional embodiments, IMAC can be used for safer and more effective myeloablative/immunosuppressive conditioning in preparation for autologous or allogeneic stem cell transplantation for treatment of cancer and genetic disorders. Alemtuzumab-based IMAC can also be used to eliminate self-reactive immune system cells in patients with life-threatening autoimmune diseases. Using IMAC, optimal immunosuppression and myeloablation can be accomplished combining the use of biotinylated alemtuzumab (anti-CD52 monoclonal antibodies that can target both T cells and B cells) and biotinylated antibodies against CD34 or 133 for elimination of hematopoietic stem cells. Following transplantation of T cell depleted autologous or allogeneic hematopoietic stem cells, newly derived T cells can be easily tolerized similarly to induction of self-tolerance in utero, or to induction of neonatal tolerance, thus resulting in re-induction of self-tolerance in patients with autoimmune diseases or in recipients with cancer or genetic disorders, respectively. Effective elimination of donor's immune system by targeting all T cells and B cells may be indicated for rescue of life-threatening GVHD following unsuccessful allogeneic stem cell transplantation.

The use of lymphoablative/immunosuppressive IMAC may be also indicated for induction of transplantation tolerance to cadaveric or living related donor's bone marrow and organ allografts. Co-transplantation of donor's bone marrow cells at the time of harvesting any donor's organ results in life long transplantation tolerance and the use of IMAC for intensive immunosuppression can facilitate engraftment while preventing the risk of graft-vs-host disease (GVHD). Induction of transplantation tolerance to organ allografts is yet unmet need and considered the holy grail of organ transplantation in order to avoid the risks of mandatory life-long immunosuppressive treatment that is currently unavoidable.

In contrast to the use of conventional bispecific antibodies against a limited number of cancers, the use of IMAC provides a large number of patients with a broad spectrum of malignant disorders including all hematologic malignancies and metastatic solid tumors, an opportunity to benefit from readily available and constantly growing number of immunoglobulin complexes and conjugates. These immunoglobulin complexes and conjugates are composed, in some embodiments, of approved monoclonal antibodies available in the market, in an easy, fast, inexpensive and tailor-made methods. In contrast to bispecific antibodies capable of binding to cancer or killer cells with a single domain via a single chain Fab, treatment with IMAC is designed to induce more robust and higher affinity and stronger avidity by binding via two binding domains of each F(ab')2 of at least two monoclonal antibodies directed against both cancer cells and anti-cancer effector cells simultaneously, thus doubling the number of binding domains of each antibody and with the potential to attack different cancer antigens on the same malignant cells simultaneously. According to some embodiments of the invention, the multi-potent antibodies complexed with a larger number of anti-cancer effector cells via avidin molecule can bind up to 4 different biotinylated monoclonal antibodies. According to some embodiments of the invention, the multi-potent antibodies complexed with a larger number of anti-cancer effector cells via avidin molecule can bind three monoclonal antibodies with one additional biotinylated anti-cancer agent.

The IMAC of the invention provides the possibility of personalized treatment by designing disease-specific complexes or conjugates of antibodies using relevant antibodies from readily available sources and against many types of antigens. The antibodies are selected from available sources based on target expression on the same cancer cells, cancer-supporting blood vessels, and/or cancer protective microenvironment. In addition, the treatment methods of the invention make it possible to induce effective anti-cancer vaccination by production of memory cells against residual or recurrent disease.

The antibody complexes or conjugates of the invention can be used for treatment of different types of cancer inexpensively at an optimal timing with no need to depend on long-term cultures using a GMP facility as used for preparation of CAR-T cells or tumor infiltrating lymphocytes (TIL) that is not available in most oncology centers and rarely if ever result in cure, certainly not long-lasting immunity. The IMAC of the invention could be applied in parallel with in vivo activation of donor and patient's lymphocytes using administration of IL-2 with no prior cell processing ex vivo prior to cell infusion in centers where the use of ex vivo cell culturing is considered ATMP and not approved by local regulatory authorities. In vivo activation of donor lymphocytes makes it possible using freshly obtained MHC compatible, haploidentical or fully mismatched unrelated mononuclear cells mixed with IMAC for in vivo induction of anti-cancer immunotherapy which can be further enhanced by concomitant administration of activating cytokines.

Targeting killer cells exclusively against cancer cells by IMAC prevents undesirable reactivity against patient's normal (non-malignant) cells, even when using intentionally mismatched donor lymphocytes, yet minimizing toxicity and the risk of GVHD-like effects because of consistent rejection of mismatched lymphocytes in every non-immunosuppressed recipient.

According to some embodiments, the binding mechanism used for connection of the antibodies in the complex is avidin-biotin and therefore, conjugates or complexes of invention may be composed of 2, 3 or 4 different antibodies. According to other embodiments, the different antibodies are conjugated to polymeric scaffolds or nanoparticles or beads which may be magnetic, positively charged and/or biodegradable.

The antibodies of the IMAC can target one or more cell surface antigens, and also one or more killer cells simultaneously, thus maximizing the binding and consequently the anti-cancer effects of killer cells on the one hand, followed by induction of anti-cancer vaccination, on the other hand. It may be possible to attack cancer cells by combination of monoclonal antibodies, each targeted against a different antigen expressed on the malignant cells (e.g. anti-CD20 and anti-CD19 antibodies against B cell malignancies, anti-Her2/neu antibody and anti-EGFR antibodies against breast cancer cells, anti-GD2 antibodies and anti-EGFR against many types of solid tumors, etc.), or treating the patient with two different IMACs each directed against different cancer surface antigens and each targeting different types of T cells (e.g., using anti-CD3 and anti-CD28 monoclonal antibodies, or other combinations of antibodies against T cells). Simultaneous targeting of cancer cells with more anti-cancer killer cells and with more subsets of T cells will improve the efficacy of elimination of multi-drug resistant cancer cells.

According to some embodiments, the antibodies are anti-T cell antibodies such as anti-CD3, anti-CD28, anti-CD2, anti-CD52 (which could also target malignant B cells), anti-CD4, anti-CD8, anti-IL-2, and/or antibodies against NK cells such as anti-HNK-1, anti-CD16 (Leu11), anti-VEGF, etc.

According to some embodiments, the antibody is selected from the group consisting of Abagovomab, Abituzumab, Abrilumab, Actoxumab, Adalimumab, Adecatumumab, Aducanumab, Afasevikumab, Afutuzumab, ALD518, Alemtuzumab, Alirocumab, Altumomab pentetate, Amatuximab, Anetumab ravtansine, Anifrolumab, Anrukinzumab (IMA-638), Apolizumab, Ascrinvacumab, Aselizumab, Atezolizumab, Atinumab, Atlizumab (tocilizumab), Atorolimumab, Avelumab, Bapineuzumab, Basiliximab, Bavituximab, Begelomab, Belimumab, Benralizumab, Bertilimumab, Besilesomab, Bevacizumab, Bezlotoxumab, Bimagrumab, Bimekizumab, Bivatuzumab mertansine, Bleselumab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, cBR96-doxorubicin immunoconjugate, Cedelizumab, Cergutuzumab amunaleukin, Cetuximab, Ch.14.18, Cixutumumab, Clazakizumab, Clenoliximab, Clivatuzumab tetraxetan, Codrituzumab, Coltuximab ravtansine, Conatumumab, Concizumab, Crenezumab, Crotedumab, CR6261, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Drozitumab, Duligotumab, Dupilumab, Durvalumab, Dusigitumab, Ecromeximab, Eculizumab, Edobacomab, Edrecolomab, Efalizumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Etaracizumab, Etrolizumab, Evinacumab, Evolocumab, Exbivirumab, Fanolesomab, Faralimomab, Farletuzumab, Fasinumab, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, IMAB362, Imalumab, Imciromab, Imgatuzumab, Inclacumab, Indatuximab ravtansine, Indusatumab vedotin, Inebilizumab, Infliximab, Intetumumab, Inolimomab, Inotuzumab ozogamicin, Ipilimumab, Iratumumab, Isatuximab, Itolizumab, Ixekizumab, Keliximab, Labetuzumab, Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MABpl, Mapatumumab, Margetuximab, Mavrilimumab, Matuzumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Namilumab, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oregovomab, Orticumab, Otelixizumab, Otlertuzumab, Oxelumab, Ozanezumab, Ozoralizumab, Pagibaximab, Palivizumab, Pamrevlumab, Vectibix, Pankomab, Panobacumab, Parsatuzumab, Pascolizumab, Pasotuxizumab, Pateclizumab, Patritumab, Pembrolizumab, Pemtumomab, Perakizumab, Pertuzumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Sonepcizumab, Sontuzumab, Stamulumab, Suvizumab, Tabalumab, Tacatuzumab tetraxetan, Talizumab, Tamtuvetmab, Tanezumab, Taplitumomab paptox, Tarextumab, Tefibazumab, Tenatumomab, Teneliximab, Teplizumab, Teprotumumab, Tesidolumab, Tetulomab, Tezepelumab, TGN1412, Ticilimumab (tremelimumab), Tildrakizumab, Tigatuzumab, Timolumab, Tisotumab vedotin, TNX-650, Tocilizumab (atlizumab), Toralizumab, Tosatoxumab, Tositumomab, Tovetumab, Tralokinumab, Trastuzumab, Trastuzumab emtansine, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, Zolimomab aritox, and any combination thereof. Each possibility represents a separate embodiment of the invention.

According to some embodiments, the antibody is against a target selected from the group consisting of: 1-40-β-amyloid, 4-1BB (CD137), 5AC, activated F9, F10, activin receptor-like kinase 1, ACVR2B, adenocarcinoma antigen, AGS-22M6, alpha-fetoprotein, angiopoietin 2, angiopoietin 3, anthrax toxin, AOC3 (VAP-1), B7-H3, *Bacillus anthracis* anthrax, BAFF, beta amyloid, B-lymphoma cell, C5, CA-125, CA-125 (imitation), calcitonin, *Canis lupus familiaris* IL31, carbonic anhydrase 9 (CA-IX), cardiac myosin, CCL11 (eotaxin-1), CCR2, CCR4, CCR5, CD11, CD18, CD125, CD140a, CD147 (basigin), CD15, CD152, CD154 (CD40L), CD19, CD2, CD20, CD200, CD22, CD23 (IgE receptor), CD25 (a chain of IL-2 receptor), CD27, CD4, CD6, CD28, CD3, CD3 epsilon, CD30 (TNFRSF8), CD33, CD37, CD38, CD4, CD40, CD44 v6, CD5, CD51, CD52, CD56, CD6, CD70, CD74, CD79B, CD80, CEA, CEA-related antigen, CFD, CGRP, ch4D5, CLDN18.2, *Clostridium difficile*, clumping factor A, coagulation factor III, CSF1R, CSF2, CTGF, CTLA-4, CXCR4 (CD184), cytomegalovirus, cytomegalovirus glycoprotein B, dabigatran, DLL3, DLL4, DPP4, DR5, *E. coli* shiga toxin type-1, *E. coli* shiga toxin type-2, EGFL7, EGFR, endoglin, endotoxin, EpCAM, ephrin receptor A3, episialin, ERBB3 (HER3), F protein of respiratory syncytial virus, FAP, FGF 23, fibronectin extra domain-B, folate hydrolase, folate receptor alpha, Frizzled receptor, GCGR, GD2 ganglioside, GDF-8, glypican 3, GMCSF receptor α-chain, GPNMB, growth differentiation factor 8, GUCY2C, hemagglutinin, hepatitis B surface antigen, HER1, HER2/neu, HGF, HHGFR, histone complex, HIV-1, HLA-DR, HNGF, human beta-amyloid, human TNF, ICAM-1 (CD54), ICOSL, IFN-α, IFN-γ, IgE, IgE Fc region, IGF-1 receptor (CD221), IGF1, IGF2, IGHE, IL 17A, IL 17A and IL 17F, IL 20, IL-1, IL-12, IL-23, IL-13, IL-17, IL17A and IL17F, ILIA, IL-1β, IL2, IL-22, IL23, IL23A, IL31RA, IL-4, IL-5, IL-6, IL-6 receptor, IL9, ILGF2, influenza A virus hemagglutinin HA, integrin α4, integrin α4β7, integrin α5β1, integrin α7β7, integrin αvβ3, interferon gamma-induced protein, interferon receptor, interferon α/β receptor, ITGA2 (CD49b), kallikrein, KIR2D, KLRC1, Lewis-Y antigen, LFA-1 (CD11a), LINGO-1, lipoteichoic acid, LOXL2, L-selectin (CD62L), LTA, MCP-1, mesothelin, MIF, MS4A1, MSLN, MUC1, mucin CanAg, myelin-associated glycoprotein, myostatin, NCA-90 (granulocyte antigen), neural apoptosis-regulated proteinase 1, NGF, N-glycolylneuraminic acid, NOGO-A, Notch 1, Notch receptor, NRP1, Oryctolagus *cuniculus*, OX-40, oxLDL, PCSK9, PD-1, PDCD1, PDGF-R a, phosphate-sodium co-transporter, phosphatidylserine, platelet-derived growth factor receptor beta, prostatic carcinoma cells, *Pseudomonas aeruginosa, Pseudomonas aeruginosa* type III secretion system, rabies virus glycoprotein, RANKL, respiratory syncytial virus, RHD, Rhesus factor, RON, RTN4, scatter factor receptor kinase, sclerostin, SDC1, selectin P, SLAMF7, SOST, sphingosine-1-phosphate, *Staphylococcus aureus*, STEAP1, TAG-72, TEM1, tenascin C, TFPI, TGF beta 1, TGF beta 2, TGF-β, TNFR superfamily member 4, TNF-α, TRAIL-R1, TRAIL-R2, TSLP, tumor antigen CTAA16.88, tumor specific glycosylation of MUC1, tumor-associated calcium signal transducer 2, TWEAK receptor, TYRP1 (glycoprotein 75), VEGF, VEGF-A, VEGFR-1, VEGFR2, vimentin, VWF, and any combination thereof. Each possibility represents a separate embodiment of the invention.

In contrast to simple, readily available and inexpensive treatment of cancer using IMAC, other available cell-mediated modalities against cancer such as tumor infiltrating lymphocytes (TIL) and particularly the chimeric antigen receptors (CAR-T) that are complicated, time consuming, laborious and expensive, and are based on enrichment of lymphocytes that sometimes cannot be accomplished because of prior chemotherapy or radiation. In addition, such cellular procedures are effective against a limited number of cancer types and even then, cure is rare if ever, and therefore, following induction of complete remission of certain hematologic malignancies by CAR-T cells, often an allogeneic stem cell transplantation is indicated, a hazardous and expensive procedure, in an attempt to eliminate residual malignant cells.

In sharp contrast to the CAR-T procedures currently considered the most effective cell-mediated anti-cancer immunotherapy, IMAC is likely to be much more effective for cure of many different types of cancer as soon as indicated in many more oncology centers and at a lower cost. Whereas CAR-T treatment depends on availability of GMP facility, team experienced in gene therapy and cell cultures, several weeks needed for expansion of the number of T cells that may be suppressed by prior anti-cancer treatment and certainly too expensive to serve every patient with cancer in need, the IMAC technology is provides more practical solution for a larger number of patients in need. IMAC is a much simpler treatment method that can be applied as soon as indicated for treatment a broader spectrum of cancers, using off-the-shelf components, or applicable following 4-6 days of culturing if used with freshly obtained haploidentical donor lymphocytes. Treatment using IMAC that induces more effective anti-cancer cytotoxicity based on the use of activated mismatched donor lymphocytes will also provide induction of anti-cancer vaccination not yet available by TIL or CAR-T cells at a reasonable cost affordable for every patient in need.

Without wishing to be bound by theory, the anti-cancer immunotherapy of the invention that comprises disease-specific IMAC has the following advantages as compared with currently available bispecific antibodies, CAR-T cells or TIL technology.

Cancer killing capacity of intentionally mismatched pre-activated killer cells, readily available off-the-shelf, or freshly prepared mononuclear donor lymphocytes obtained by apheresis with no need for prior ex vivo activation, or using donor lymphocytes, containing both T cells, NK cells and NKT cells, pre-activated ex vivo and also following infusion in vivo, are likely to be much more effective than using patient's own lymphocytes that are a priori tolerant to cancer. In contrast, alternative cell-based therapeutic procedures based on the use of bispecific antibodies, TIL or CAR-T cells focus on targeting patient's own lymphocytes against cancer cells. We have already documented that cure (>35 years disease-free survival) of otherwise malignancies resistant to supra-lethal myeloablative conditioning can be accomplished with alloreactive donor lymphocytes, suggesting the feasibility to eradicate "the last cancer cell" by alloreactive donor lymphocytes (2-5). In contrast, immunotherapy by CAR-T frequently fails to eradicate all malignant cells (28) and therefore it is usually followed by allogeneic stem cell transplantation. Similarly, immunotherapy with TIL alone rarely if ever results in complete cure.

In addition to the most potent anti-cancer effects that can be mediated spontaneously by mismatched donor lymphocytes against MHC incompatible cancer cells, anti-cancer effects of donor (as well as patient's) lymphocytes can be further activated ex vivo and/or in vivo with cytokines (e.g. IL-2; IL-12; IL-15; IL-17 etc.) or any other factors or antibodies-activating T cell (e.g. anti-OX40, co-stimulatory anti-CD28 or ICOS; or targeting CD69, CD25, CD71, etc.), or using intentionally mismatched NK cells by engagement of CD16, CD56, NKG2D, GM-CSF, IFN gamma, or TNF alpha, etc., likely to induce much more powerful eradication of multi-drug resistant cancer cells and cancer stem cells.

Anti-cancer cytotoxic activity by combined activity of different killer cells, and against different targets on the cell surface of cancer cells can be much more effective than anti-cancer effects mediated by bispecific antibodies, TIL or CAR-T cells. intentionally mismatched donor T cells and NK cells, attacking different targets on cancer cells simultaneously, is likely to be much more effective than cytotoxicity induced against one cell-surface antigen induced by antigen-specific autologous T cells induced by bispecific antibodies, TIL or CAR-T cells acting alone. As was already documented in pre-clinical animal models and cumulative clinical experience, allogeneic lymphocytes, especially if intentionally mismatched can eliminate the "last cancer cell" and result in cure (2-5, 7, 8). Unfortunately, the majority of patients treated with CAR-T are not cured (28) and this is why allogeneic stem cell transplantation is recommended following successful remission induction with CAR-T in most oncology centers.

Killing of cancer cells using IMAC can be targeted by intentionally mismatched NK cells alone while avoiding the use of T cells that are the cause of CRS. NK cell-mediated anti-cancer cytotoxicity may result in less or no CRS at all, as compared with frequent and potentially hazardous CRS that results following treatment with CAR-T, and which can result in severe or occasionally fatal outcome. A better safety profile anticipated by treatment with IMAC as compared with CAR-T is a major potential advantage of using IMAC.

The use of the compounds and methods of the invention makes it possible to extend the spectrum of patients with different types of cancer in need with eligible clinical indication for cell therapy, and that can benefit from a large number of existing monoclonal antibodies against cancer-associated cell surface antigens (e.g. CD10; CD19; CD20; CD38; Her2/neu; GD2; MUC1; CA-125; CEA; VEGF; EGFR) or against T cells, NK cells and antigen presenting cells (dendritic cells and macrophages). In contrast, immunotherapy with bispecific antibodies or CAR-T cells is restricted by a limited presence of suitable vectors against target antigens.

Recent studies have indicated that at the time of cancer progression additional events may develop in a large proportion of patients: (1) tumor-associated cell surface antigen may internalize or no longer exist (e.g., CD19 or CD20 in B cell malignancies); and (2) PD-1 and PD-L1 may be upregulated, as examples, thus turning off the anti-cancer capacity of CAR-T treatment mediated by T cells. In contrast, anti-cancer activity of avidin-based IMAC may be less affected by disappearance of one cell surface antigen because killing can be directed against more than one target antigen and besides, the killing is mediated against the mismatched target cells.

Whereas bispecific antibodies, TIL or CAR-T are directed against cancer antigens, the anti-cancer efficacy may be partially blocked by different mechanisms that can down-regulate anti-cancer effects (e.g., regulatory T cells; checkpoint inhibitors; myeloid-derived suppressor cells; tumor associated macrophages and infiltrating mesenchymal stromal cells) using avidin-based IMAC makes it possible to combine effective cancer cytotoxicity in parallel with down-regulation of some of the suppressive mechanisms.

Clinical application of anti-cancer immunotherapy using IMAC can be prepared instantaneously, as soon as indicated, consequently at an optimal stage of minimal residual disease and at optimal clinical condition of the patient, in sharp contrast with the delay of treatment with CAR-T cells or TIL technology, both depend on time needed for culturing T cells in an approved GMP facility, associated with major logistics limited to few highly equipped centers with GMP facilities with sufficient experience using long-term cell cultures and gene therapy. Besides, expanding sufficient number of patient's lymphocytes is not always successful, especially following prior treatment with chemotherapy and radiation therapy.

Due to technical considerations and prohibitive high cost of treatment with TIL and CAR-T cells (currently estimated at $100,000 to 450,000/patient) such treatments are not available for the large majority of patients in need.

Moreover, the IMAC technology that can be easily assembled with disease-specific components to match nearly every patient with cancer in need, seems to be the only available treatment that combines most successful anti-cancer effects followed by induction of anti-cancer vaccination. Accordingly, when applied at the stage of minimal residual disease, there is a good chance that successful clinical application of IMAC can result in cure of otherwise resistant hematologic malignancies and certain metastatic solid tumors.

Without wishing to be bound by theory, the use of IMAC for induction of anti-cancer vaccination has the following advantages as compared with conventional dendritic cell vaccines:

Conventional anti-cancer vaccines are based on in vitro preparation of dendritic cells in a well-established GMP facility. This is an ATMP procedure that is laborious, expensive and requires apheresis of the patient. Preparation of such vaccines takes 7-10 days and can be accomplished by skilled technicians working in an approved GMP facility. Moreover, until to date there is no evidence that conventional anti-cancer vaccines can result in cure so most oncologists almost never recommend patients in need to consider anti-cancer vaccination.

Conventional dendritic cells vaccines depend on availability of tumor-cells, tumor cell lysates or tumor-specific peptides that may or may not be available, whereas anti-cancer vaccination based on IMAC is likely to occur in vivo, even if no cancer samples are available and cancer-specific antigens unknown.

Conventional vaccines are based on pulsing dendritic cells with antigens derived from the primary tumor or sometimes from tumor metastases obtained ahead of time and cryopreserved. It is well known that tumor cells mutate constantly both spontaneously and especially following exposure to anti-cancer chemotherapy. As such, phenotype, tumor-associated antigens and cancer-specific expression of cell surface antigens mutate and change constantly. Therefore, a vaccine based on sensitization of patient's immune system cells against the available original tumor sample cryopreserved at the time of diagnosis or following surgery may no longer be relevant against cancer metastases developing at a later stage. In contrast, a vaccine based on in vivo sensitization against patient's current cancer antigens, accomplished by the use of IMAC, by patient's in vivo anti-cancer activity is likely to be much more effective than preparation of anti-cancer vaccine using a small number of antigen presenting cells in the laboratory against cancer antigens that may no longer exist.

To summarize the advantages of the invention, avidin-based complexes enables the use of combination of 2 to 4 different biotinylated monoclonal antibodies targeting lymphocytes against one or more cell surface cancer-associated antigens simultaneously, or 3 biotinylated monoclonal antibodies with one additional biotinylated antibodies anti-cancer agent, or 2 biotinylated monoclonal antibodies against 1 or 2 cancer-associated antigens, binding 2 different killer cells (either T cells guided by 2 different anti-T cells cell antibodies (e.g. CD4 & CD8) or 2 NK killers (e.g. using anti-CD56 & anti-CD16)), or any other biotinylated anti-cancer treatment (e.g., radiolabeled agent or chemotherapy, or antibody-drug candidate) and possibly additional cancer activating molecules, targeted against cancer cell surface antigens combined with intentionally mismatched naïve or activated effector cells of the immune system, or bound in vivo with patient's own anti-cancer effector cells and antigen presenting cells. Both intentionally mismatched killer cells or patient's own cells can be activated prior to and following cell infusion. For treatment of very resistant cancer, two different IMAC complexes or conjugates may be used jointly against multiple available cancer-associated antigens, attacking resistant cancer cells simultaneously. The use of intentionally mismatched killer cells represents the most effective approach for killing of multi-drug resistant cancer cells, including otherwise resistant cancer stem cells.

Attacking simultaneously several antigens on cancer cells by killer cells guided by more than one monoclonal antibody, is likely to be much more cytotoxic compared with targeting only one cancer cell surface antigen (e.g., attacking malignant B cells by both anti-CD20 and anti-CD19; or attacking breast cancer cells by both anti-Her2/neu and anti-EGFR simultaneously). Using conjugates, with limited number of binding sites, cancer immunotherapy may be attempted by combining one conjugate against one cell-surface antigen and another against another cell-surface antigen of the same cancer cell. The method of the invention will also result in induction of long-lasting anti-cancer vaccination induced by patient's own memory T cells.

IMAC is based on the use of readily available and clinically approved monoclonal antibodies for treatment of cancer and cytokines for activation of T cells, NK cells, NKT cells and antigen presenting cells, with suitable conjugates or complexes that can be easily prepared as indicated for each patient in need on a fully personalized basis. As such, IMAC provides an option to treat a large number of different malignancies using a broad spectrum of commercially available monoclonal antibodies complexed using an avidin molecule or conjugates prepared using previously approved linkers. Taken together, the same treatment that will result in elimination of cancer cells will also induce automatic vaccination against recurrent disease by induction of long-lasting resistance against residual or recurrent disease. Using avidin injected directly into cancer tissue, followed by intravenous injection of biotinylated monoclonal antibodies, a similar procedure can be used for simply, fast and most effective induction of personalized anti-cancer vaccination.

For treatment of minimal residual disease, IMAC can applied with no prior conditioning or using minimally immunosuppressive conditioning (e.g. using low dose cyclophosphamide or combination of fludarabine and cyclophosphamide), thus suppressing regulatory T cells that are particularly sensitive to low dose cyclophosphamide, and also extending the duration of donor lymphocytes and enhancing the contribution of newly host derived immune system cells by optimizing the so-called homeostatic proliferation.

The IMAC procedure can be applied using freshly obtained or off-the-shelf unrelated killer cells prepared from circulating blood lymphocytes, lymph node lymphocytes or even expanded NK cells derived from unrelated fully mismatched lymphocytes, haploidentical or MHC compatible lymphocytes freshly activated prior to cell infusion or readily available ex vivo activated prior to cryopreservation as readily available for immediate use off-the-shelf. Further activation of intentionally mismatched killer cells, both T, NK and NKT cells, can be easily activated in vivo by administration of well-tolerated low-dose IL-2 (for activation of T cells & NK cells) and using KRN7000 (for activating of NKT cells) for a few days until rejection will eliminate all mismatched donor lymphocytes. Consistent rejection of intentionally mismatched killer cells guarantees no risk from GVHD-like toxicity.

In principle, as indicated above, the IMAC technology could be useful for elimination of undesirable non-malignant cells as well as infective agents based on similar principles used for elimination of cancer cell followed by induction of residual long-lasting immunity.

The efficacy of the IMAC technology of the present invention for complete elimination of cancer cells was confirmed by results of experiments summarized in FIGS. 5-13. Induction of long-lasting immunity by single Fab binding to IL-2 activated T cells and cancer cells, attacking jointly malignant melanoma in vivo in mice following rejection of mismatched lymphocytes is supported by preclinical animal experiments, based on the in vivo use of bispecific antibody (anti-CD3×anti-EpCAM) that binds T cells and cancer cells with one single Fab each for treatment of a lethal challenge of malignant melanoma. This bispecific antibody attached to IL-2 activated blood lymphocytes eliminated lethal challenge of malignant melanoma in mice and resulted in cure in contrast to 100% death of untreated recipients of a similar challenge of malignant melanoma (22, 23). At 6 months later, following rejection of donor lymphocytes with no residual traces of the bispecific antibody, successfully treated tumor-free mice resisted a second lethal challenge of malignant melanoma, thus confirming induction of long-lasting immunity that protected successfully treated mice from recurrent disease. Elimination of all cancer cells after dual attack of fully intact monoclonal antibodies binding to T cells and cancer cells with stronger affinity F(ab)2 each is likely to induce much more effective anti-cancer effects as compared with single Fab binding to T cells and cancer cells. Similarly, induction of long-lasting immunity by activation of recipient's immune system by at least 2 intact monoclonal antibodies is likely to be much more effective as compared with induction of immunity by single chain binding of bispecific antibody. In addition, in vivo studies in mice using IL-2 activated lymphocytes confirmed that due to targeting anti-cancer effector cells to cancer cells with eventual rejection of killer cells did not result in anti-host toxicity since no graft-vs-host disease (GVHD) developed (22, 23).

The results of the in vivo experiments suggested that selective killing of targeted cancer cells could be accomplished by IMAC while avoiding any cytotoxicity against normal patient's tissues before all allogeneic killer cells will be rejected and that long lasting anti-cancer immunity was mediated by activation of recipient's immune system cells connected and activated by IMAC following rejection of all malignant melanoma cells. Indeed, rejection of mismatched lymphocytes leaves behind the IMAC skeleton, with monoclonal antibodies ready to be connected to cancer antigens and recipient/patient's own T cells.

Taken together, due to the capacity of IL-2 activated mismatched killer cells to eliminate all cancer cells when applied against a lethal challenge of cancer cells and induce long-lasting anti-cancer vaccination, treatment with IMAC is likely to result in cure especially if applied against minimal residual disease following conventional treatment. On the other hand, due to intentional use of mismatched donor lymphocytes such killer cells are always rejected within a week or so, thus avoiding the risk of GVHD-like toxicity. In case the recipient may be partially immunosuppressed by prior anti-cancer treatment, IL-2 activated donor lymphocytes can be exposed to sublethal radiation that blocks proliferation of T cells and retains the cytotoxic capacity of NK cells (21).

In addition to direct elimination of otherwise resistant malignant cells the present invention provides, according to an aspect, a method of vaccination and induction of long-lasting anti-cancer immunity, the method comprising an intra-tumor injection of avidin, optionally using ultrasound or CT guided needle and administering in-vivo biotinylated monoclonal antibodies together with intentionally mismatched cytokine activated donor killer lymphocytes (T & NK cells), first resulting in in situ lysis of cancer cells, followed by influx of patient's own lymphocytes and antigen presenting cells following rejection of donor lymphocytes. As such, systemic immunity can be established against untreated remote metastases (abscopal effect).

The present invention thus also provides a method of induction of anti-cancer vaccination, the method comprising direct (intratumor) injection of avidin into the primary tumor or visible easily accessible metastatic lesion, followed by injection of biotinylated monoclonal antibodies alone or with additional biotinylated immune activating agents (e.g., IL-2 or 4-1BB) or any other anti-cancer modality (e.g., chemotherapy or radiolabeled molecule or biotinylated oncolytic virus). According to this method, the avidin complex or an equivalent conjugate, binds to biotinylated monoclonal antibodies and/or any of the aforementioned agents, thus resulting in in-vivo local cytotoxicity to cancer cells and local recruitment of antigen presenting cells, using the treated cancer lesion as in situ vaccine, even if no cancer-associated antigen is evident and even if the full phenotype of the type of cancer to be treated cannot be fully defined, thus creating fully personalized in situ anti-cancer vaccine in vivo.

According to some embodiments, the present invention provides a method for vaccination of a subject having cancer with no known cancer-associated antigen, the method comprises injection of cancer cells together with IMAC containing anti-T cells and/or NK cells to attract patient's own T cells, NK cells and antigen presenting cells to the lymphatic system, where optimal anti-cancer vaccination can occur. According to some embodiments, the vaccination method comprises injecting of the complex or conjugate proximally to the draining lymph nodes. According to some embodiments, sensitization of patients T cells is performed by concomitant injection of GM-CSF.

For induction of anti-cancer vaccination there are several treatment options available, ideally based on the use of mismatched activated donor lymphocytes attached to biotinylated antibodies monoclonal antibodies that can selectively target cancer lesion containing avidin, followed by in situ activation of anti-cancer immunity by patient's immune system after rejection of mismatched donor cells by interaction with IMAC as documented in FIG. 4. Here are the options using IMAC for preparation of in situ vaccination against cancer using a two-step or one-step approach:

1. Injection of avidin alone, or avidin linked to biotinylated monoclonal anti-cancer antibodies, into a visible cancer metastatic lesion by CT or ultrasound guided needle, followed by intravenous injection of activated lymphocytes linked to biotinylated anti-T cells antibodies, respectively. Following in situ cytotoxicity against cancer followed by rejection of mismatched donor lymphocytes, patient's own T cells and antigen presenting cells will be targeted to the disintegrated cancer tissue with IMAC with anticipated pulsing of patient's dendritic cells resulting in sensitized T cells that will develop helper, cytotoxic and memory T cells for systemic induction of anti-cancer immunity against residual malignant cells and or protection against recurrent disease.
2. Alternatively, using direct injection of IMAC—avidin linked to biotinylated anti-cancer and anti-T cells monoclonal antibodies, into a visible cancer metastatic lesion by CT or ultrasound guided needle. Following in situ cytotoxicity against cancer followed by rejection of mismatched donor lymphocytes, patient's own T cells and antigen presenting cells will be targeted to the disintegrated cancer tissue with IMAC with anticipated pulsing of patient's dendritic cells resulting in sensitized T cells that will develop helper, cytotoxic and memory T cells for systemic induction of anti-cancer immunity against residual malignant cells and/or protection against recurrent disease.

Induction of anti-cancer vaccination should be combined with systemic activation of patient's own immune system (e.g., using checkpoint inhibitors; combinations of IL-2 and alpha interferon, or any other immune stimulating agents) to maximize an immune response against the targeted cancer lesion and towards more effective activation of patient's own immune system against cancer. Systemic activation of patient's immune system with intra-lesional, in situ activation of T cells and dendritic cells can result in induction of helper and cytotoxic T cells and also memory T cells for elimination of residual malignant cells and for protection against recurrent disease.

According to some embodiments, the method comprises administration of the immunoglobulin complex or conjugate against residual malignant cells following conventional anti-cancer modalities or after autologous or allogeneic stem cell transplantation, based on the cumulative experience confirming that activated allogeneic lymphocytes, particularly if mismatched, can eliminate all malignant cells and result in cure, as confirmed in pre-clinical animal models of murine leukemia/lymphoma and in clinical trials, as well as confirmation that donor lymphocyte infusion (DLI) can be used to eliminate residual malignant cells after maximally tolerated myeloablative conditioning rescued with allogeneic stem cell transplantation (17-20, 29-31).

Any method of treating cancer, using the pharmaceutical compositions of the present invention, may be part of a regiment of cancer treatment, including but not limited to chemotherapy, immunotherapy, biotherapy, radiation, bone-marrow transplantation and surgery.

Anti-cancer cell-mediated immunotherapy according to the present invention may be also supported by administration of an anti-inflammatory agent that suppresses upregulation of cancer genes by inflammation as well as controls fever and malaise that may result by intensive immune system activation.

The following examples are presented in order to fully illustrate some embodiments of the invention. They should, in no way be construed as limiting the scope of the invention.

EXAMPLES

Compounds and Methods

Biotinylated antibodies are commercially available.

Biotinylation of other monoclonal antibodies is performed by binding biotin to lysine residues using the N-hydroxysuccinimide or p-nitrophenyl esters or other activated esters, as described for example in Methods in Enzymology vol. 184, pages 3-746 (1990), Edited by Meir Wilchek and Edward A. Bayer.

Avidin molecules to be used include but are not limited to egg-white Avidin, StreptAvidin, NeutrAvidin, Neutralight Avidin, NitroAvidin, Caped Avidin, Avidins from bacteria, and/or genetically engineered and modified Avidins.

To increase the number of antibodies on the Avidins, the Avidin is crosslinked or polymerized using methods known in the art.

Figure 1B:
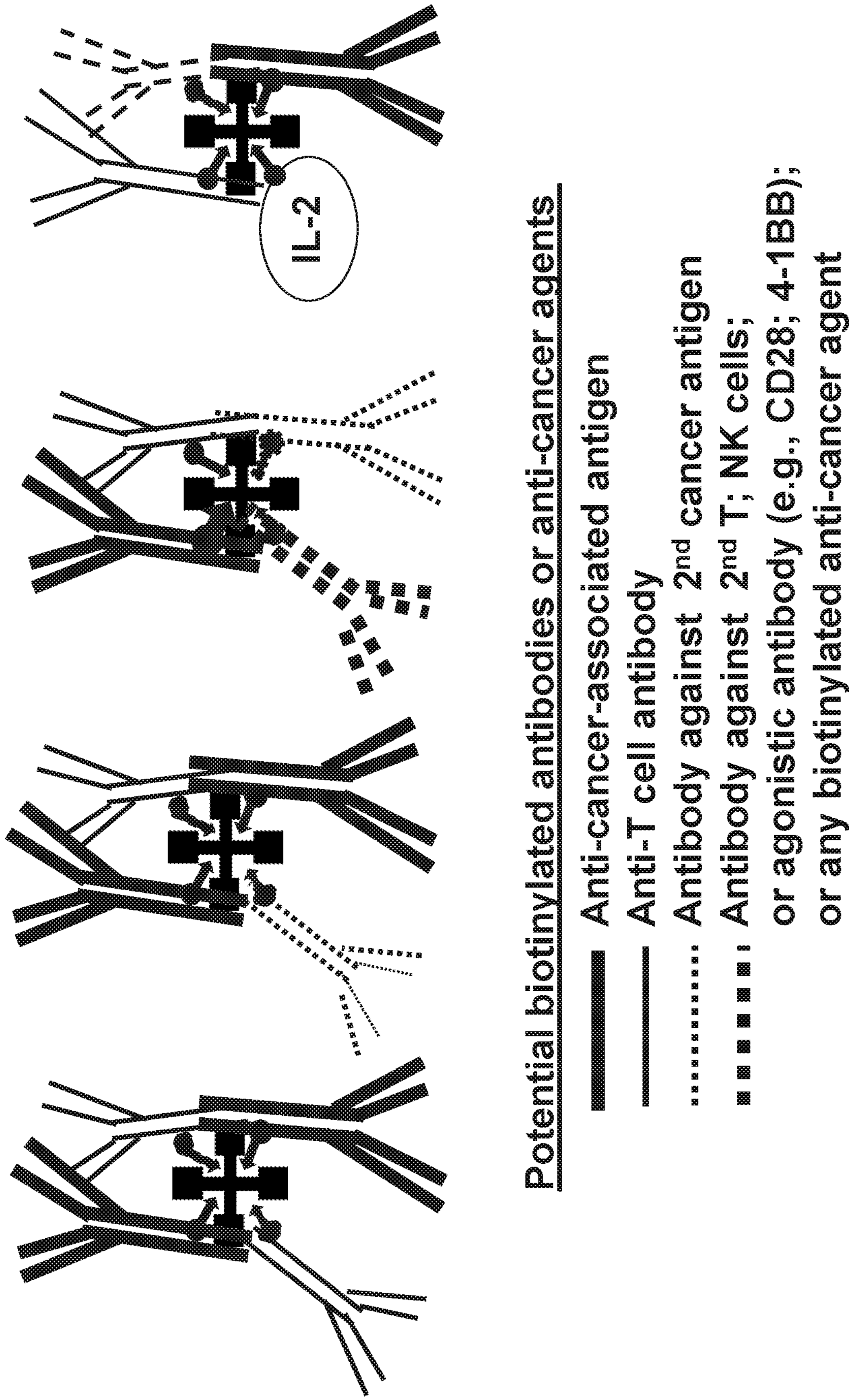
Figure 1C:
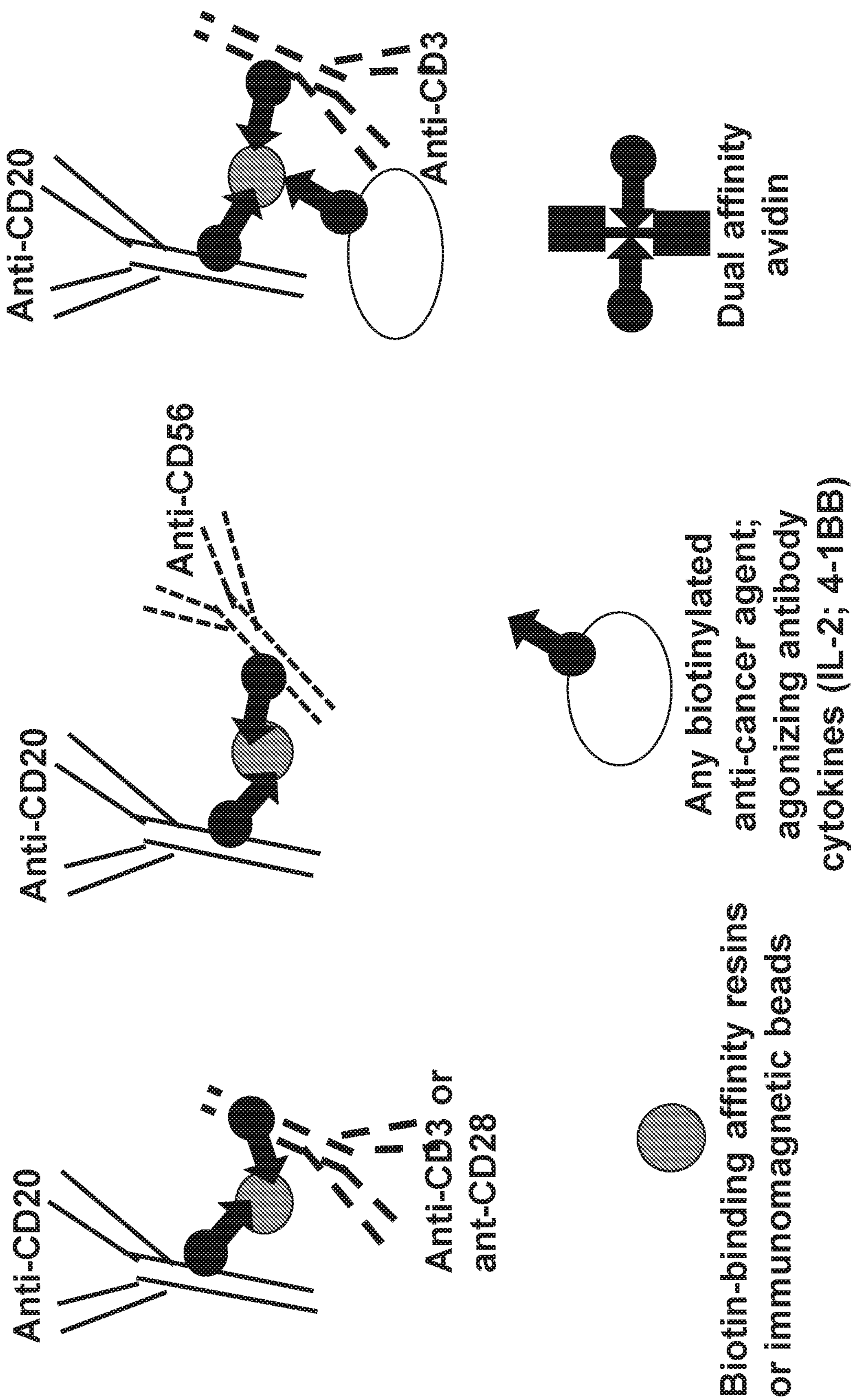
Figure 2A:
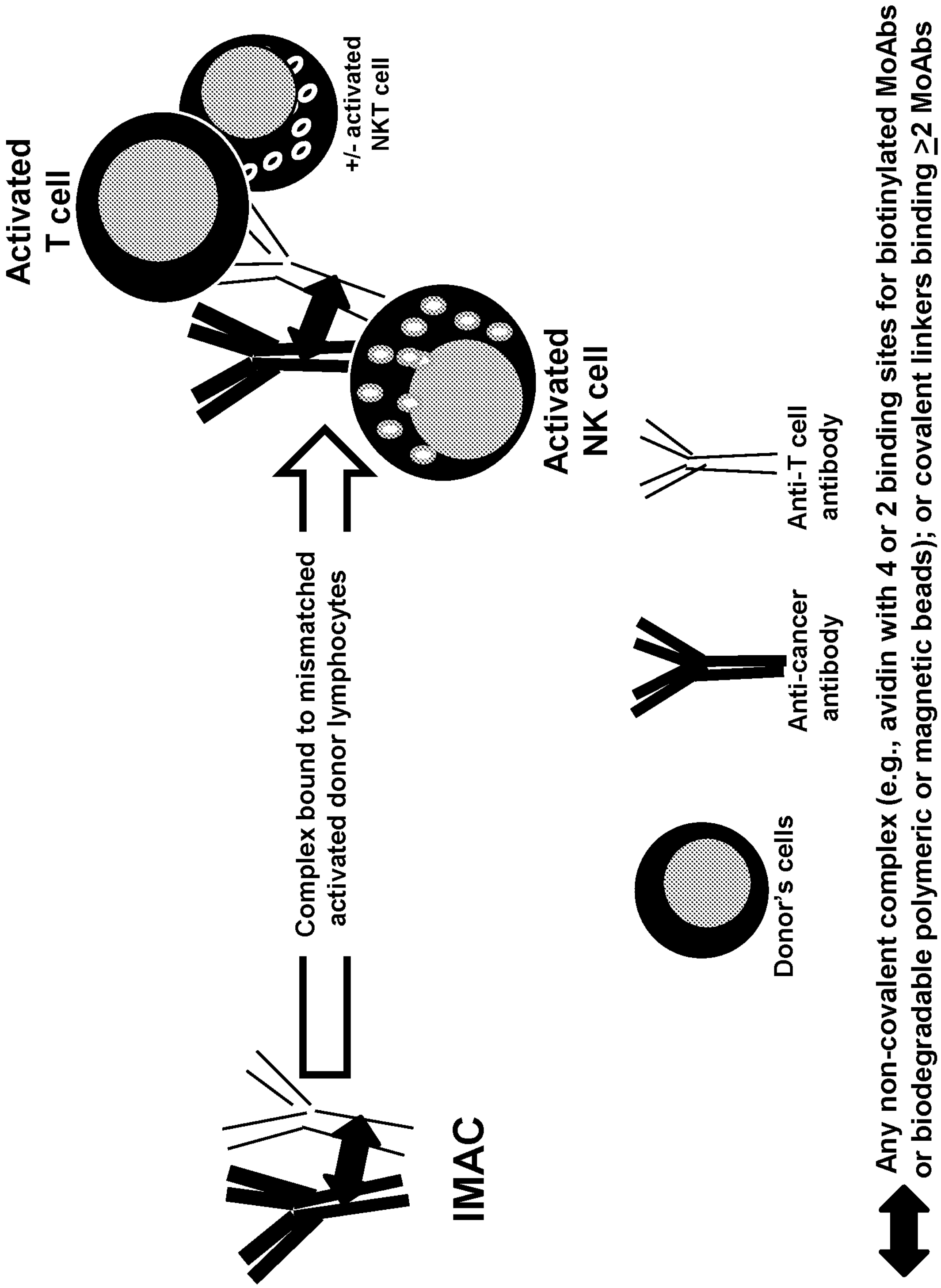
Figure 2B:
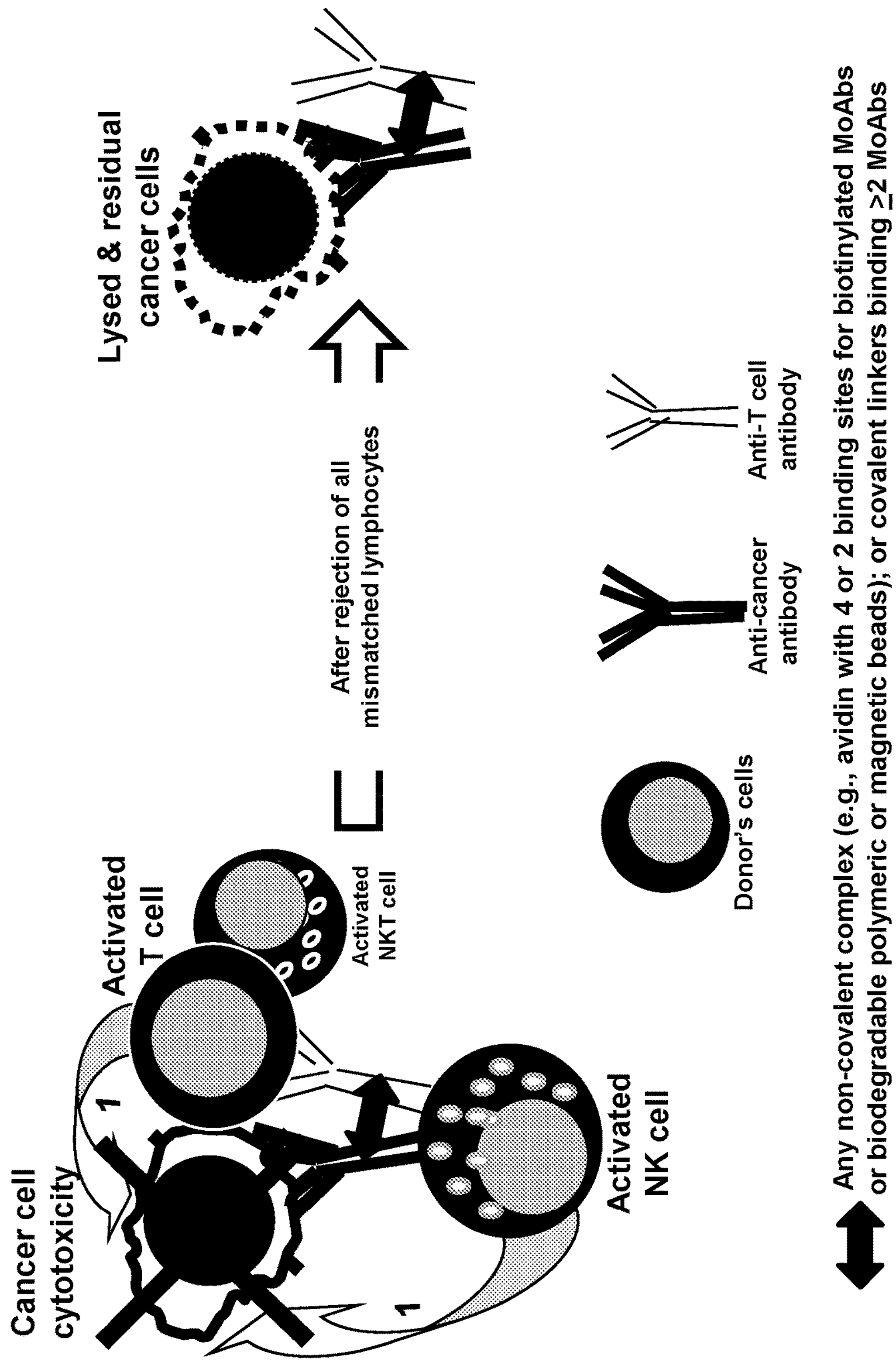
Figure 3A:
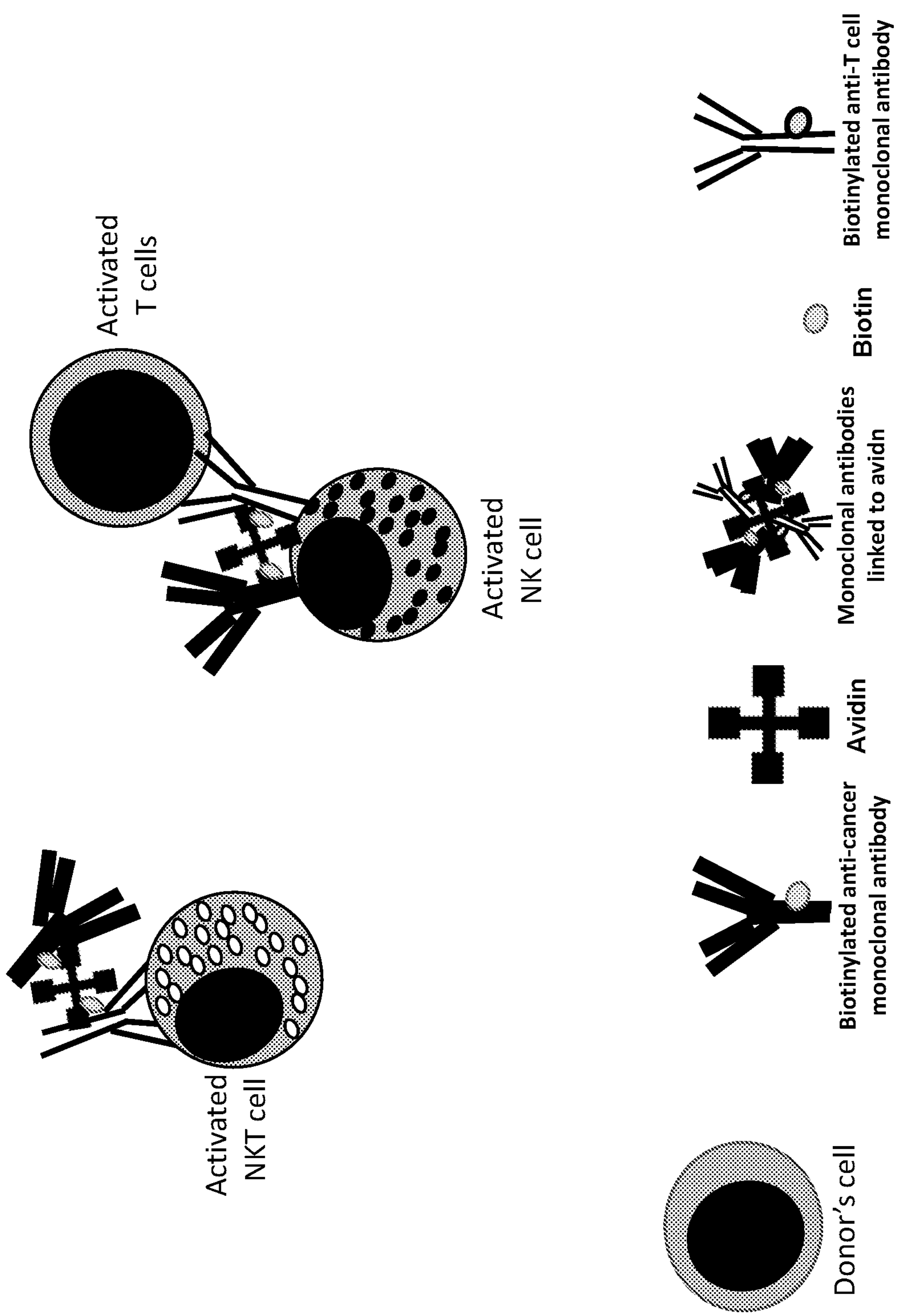
FIGS. 3A-3E. A schematic representation of the cytotoxic activity of the IMAC of the invention and process of induction of anti-cancer cytotoxicity followed by induction of an immune response against cancer antigens with long-lasting memory T cells that can eliminate residual malignant cells and prevent recurrent disease according to some embodiments of the invention. The anti-cancer effects are identical to the anti-cancer mechanism described in FIG. 2, but with more potent anti-cancer effects mediated by simultaneous targeting with four instead of two monoclonal antibodies or using four different biotinylated antibodies and/or anti-cancer agents.
Figure 3B:
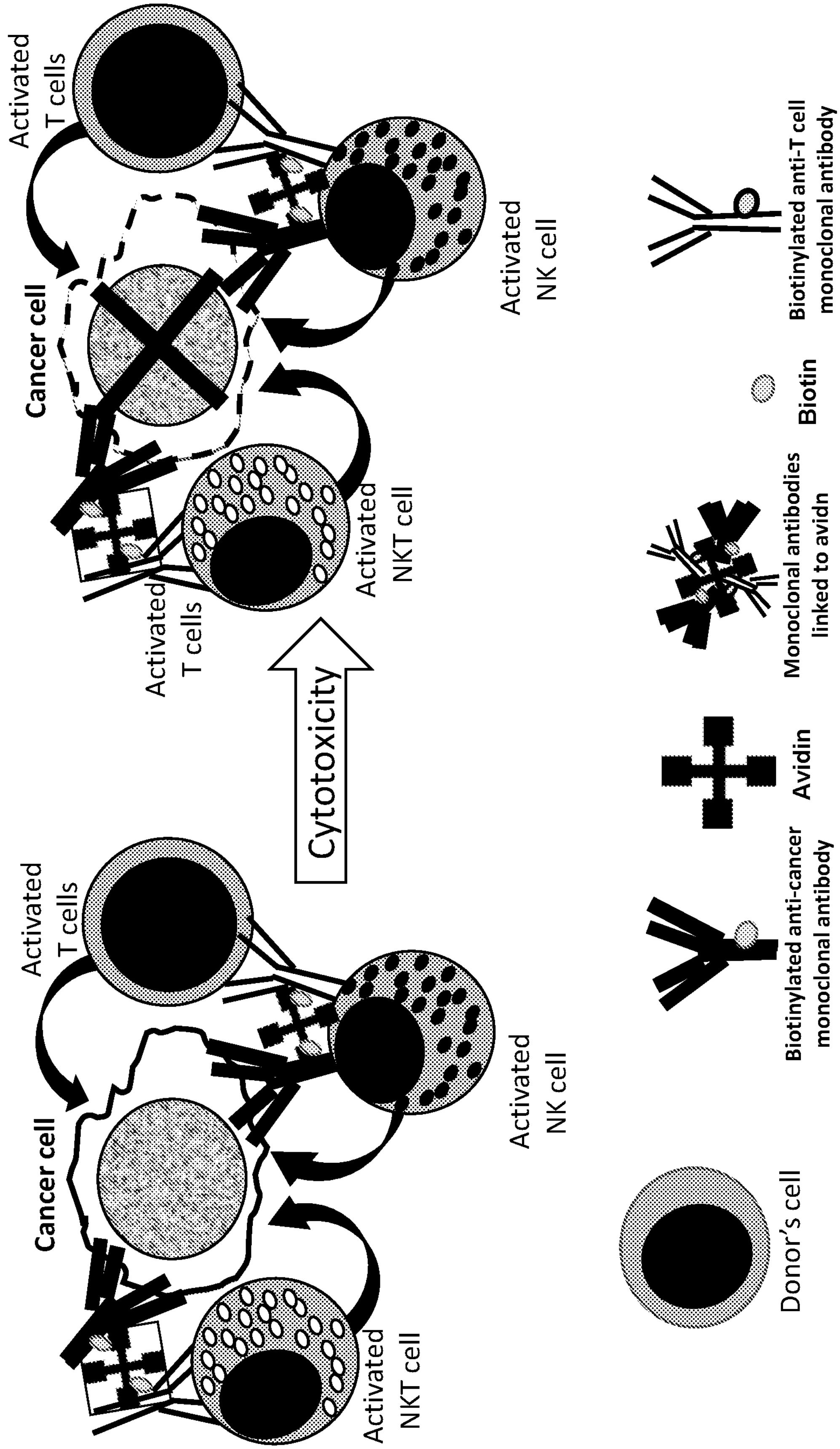
Figure 3C:
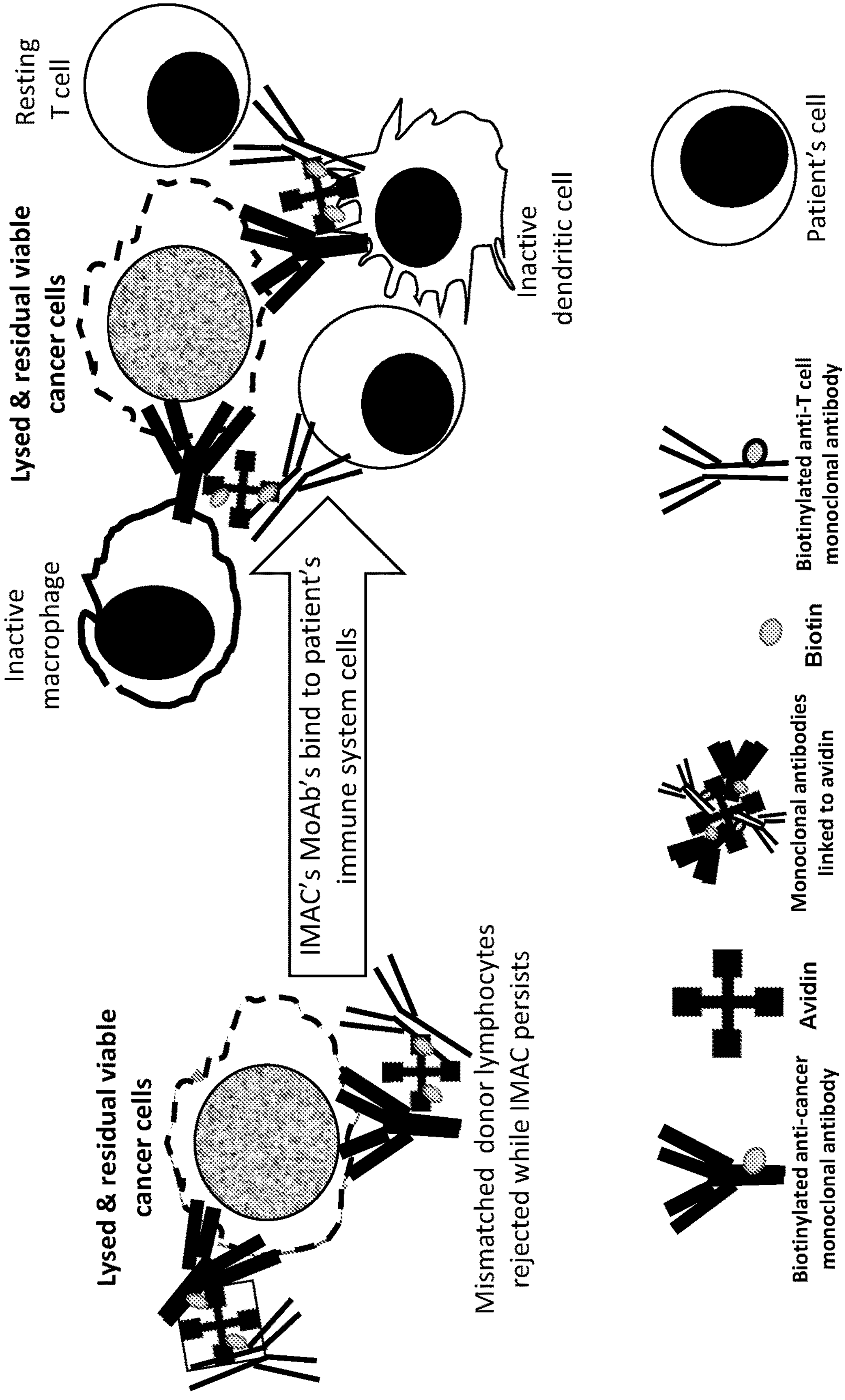
Figure 3D:
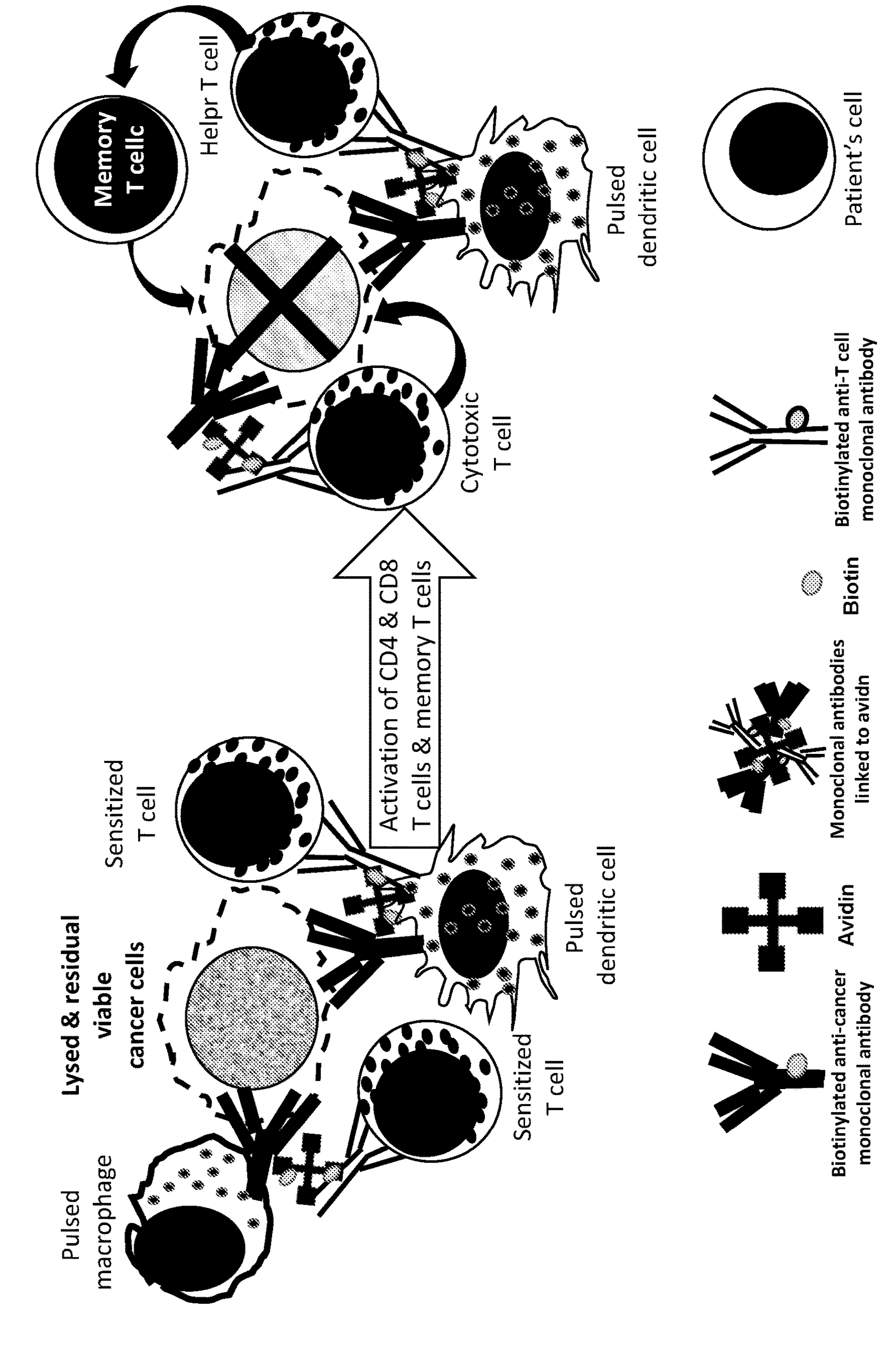
Figure 3E:
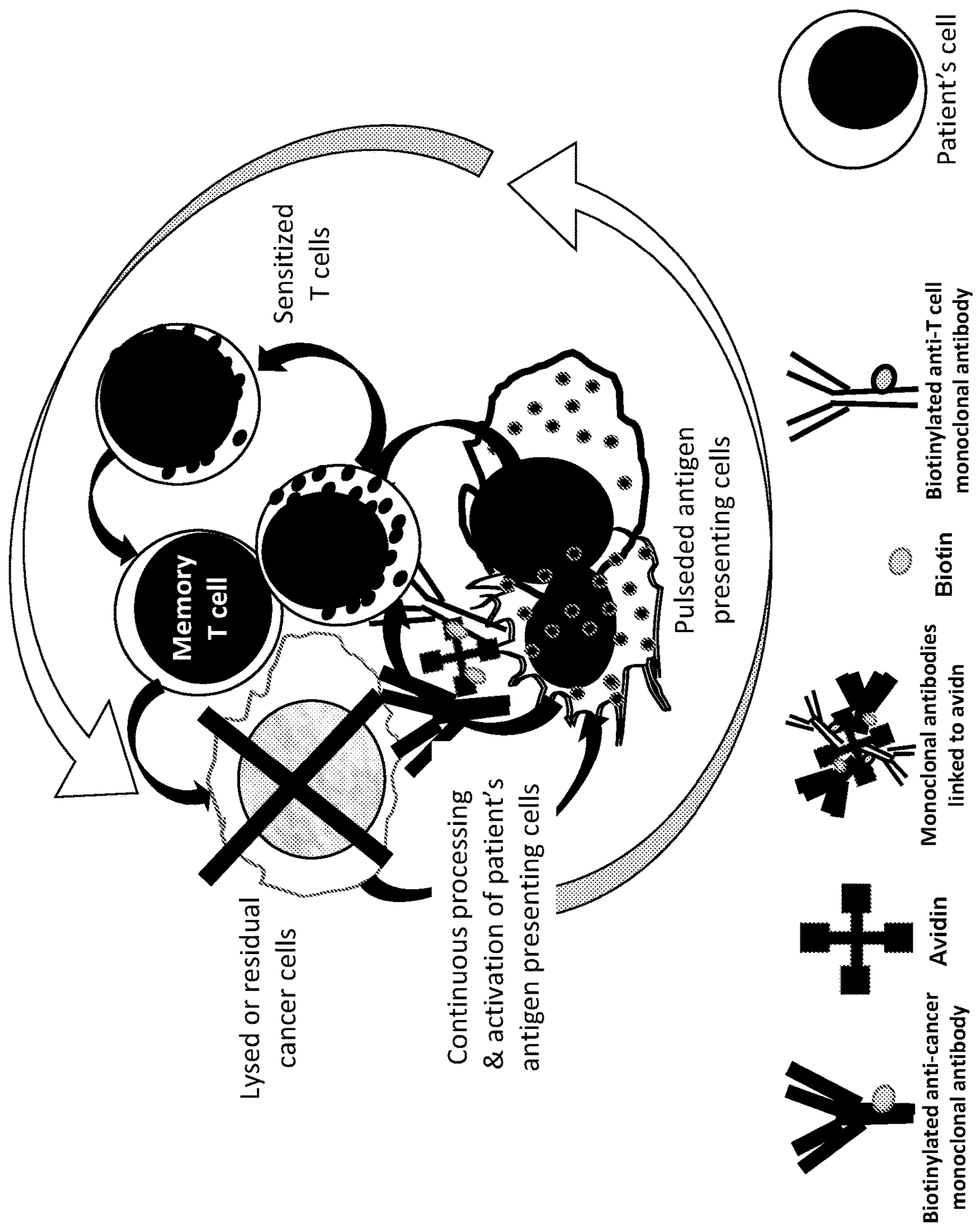
Figure 4A:
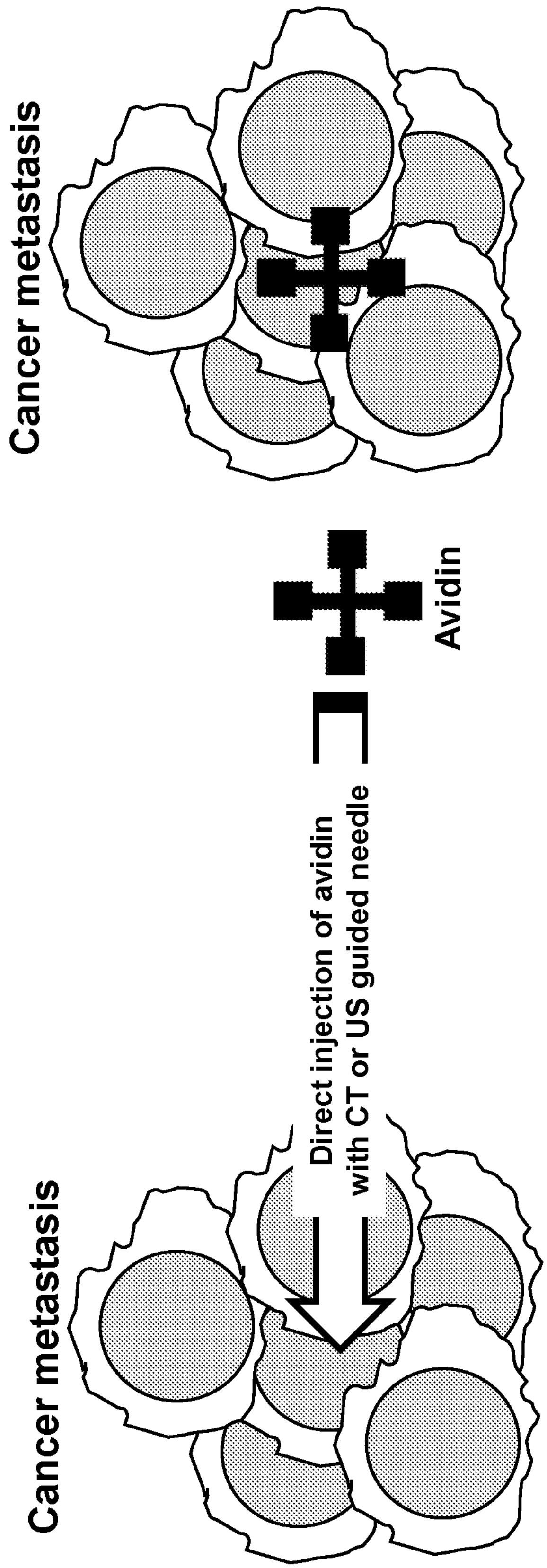
FIGS. 4A-4D. A schematic representation of two different options for using the avidin-biotin-based IMAC for induction of long-lasting anti-cancer vaccination in situ according to some embodiments of the invention.
Figure 4B:
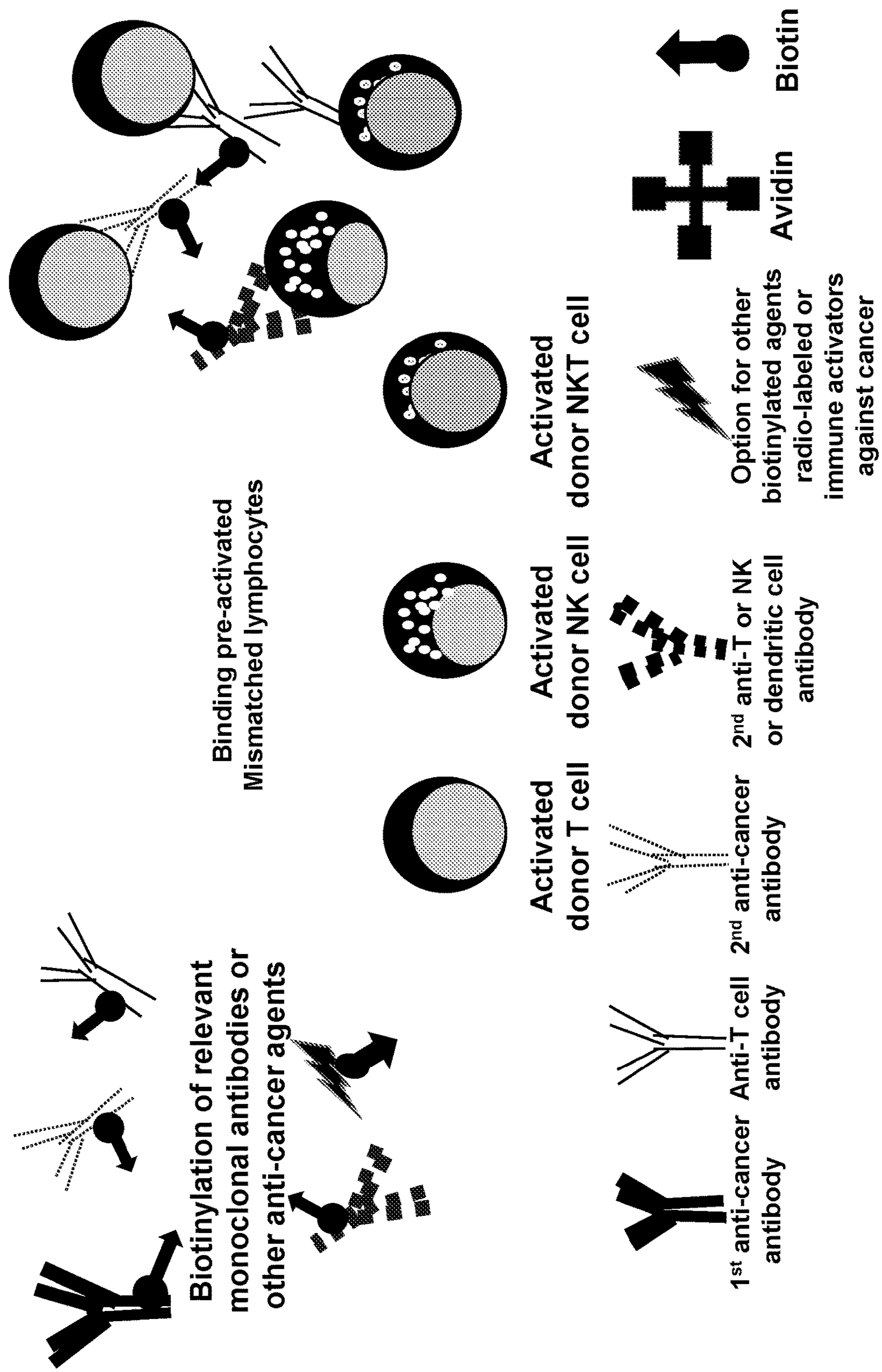
Figure 4C:
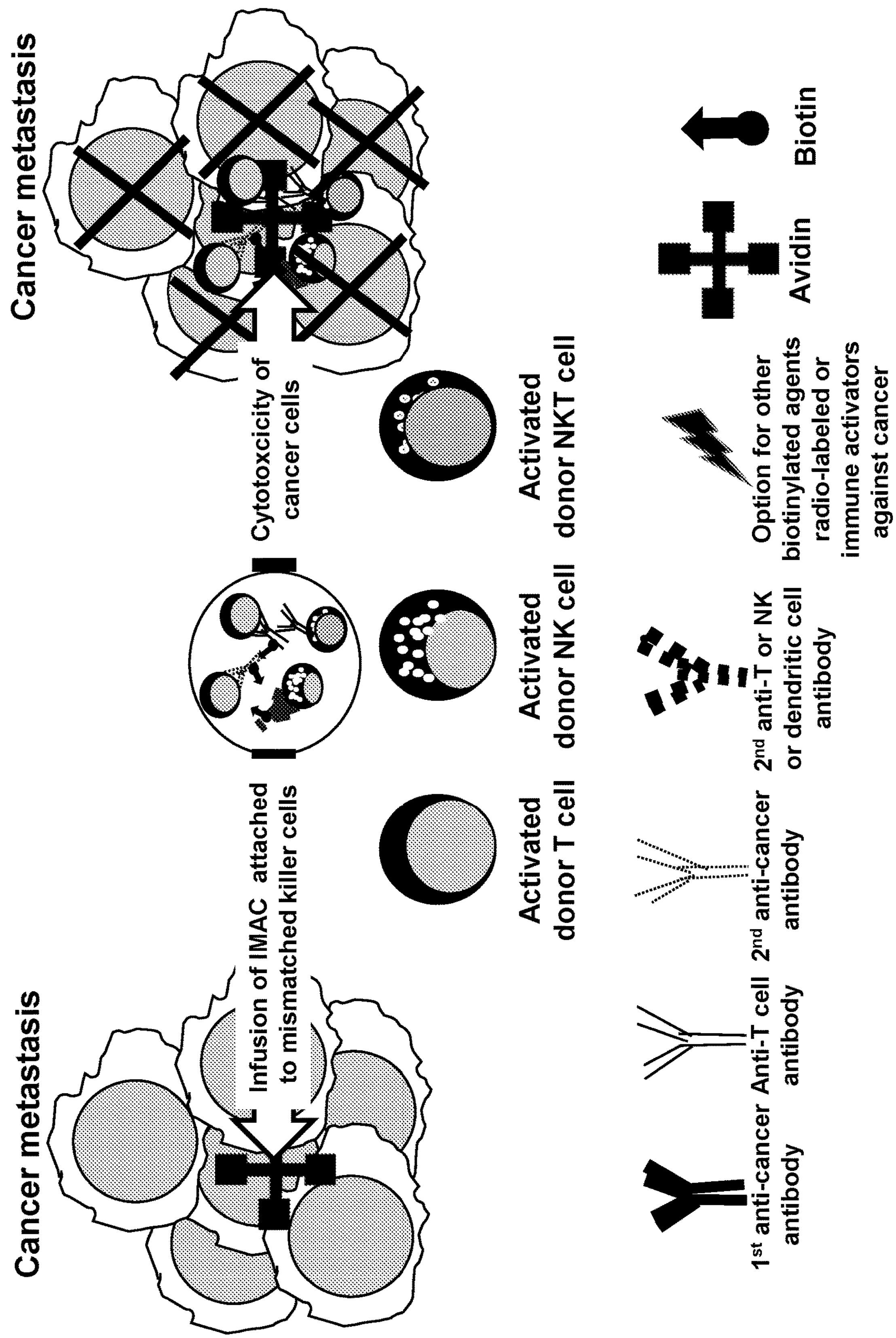
Figure 4D:
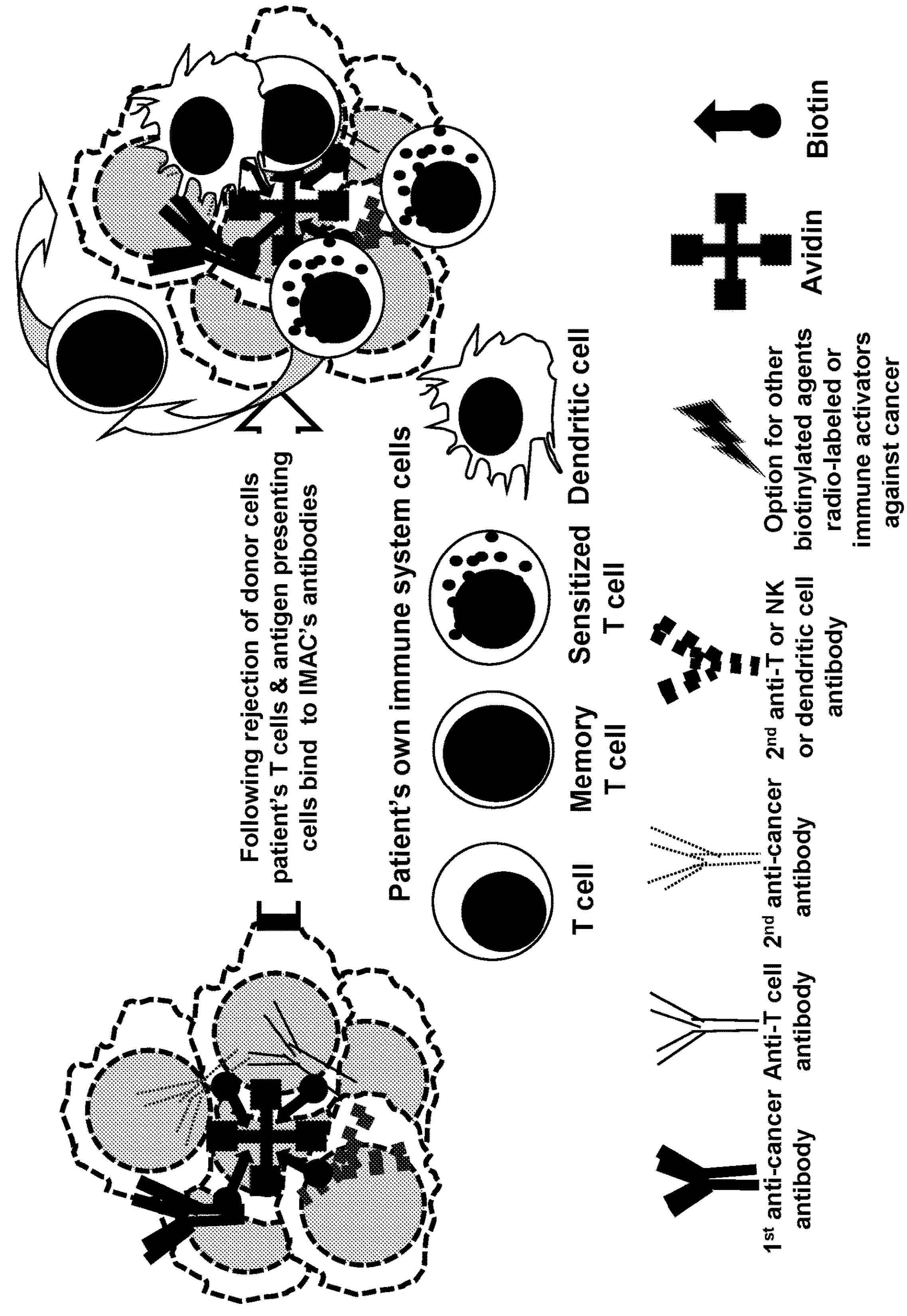

Covalently crosslinking and polymerize of antibodies is performed using cleavable and non-cleavable crosslinking reagents known in the art. Exemplified IMAC structure and binding is shown in FIGS. 1A-1C.

Example 1: Biotinylation of Monoclonal Antibodies

An exemplary method for biotinylation of monoclonal antibodies free amine group of a Lysine residue in the antibody's sequence is utilizes as described above, and also in Mao S Y. (2010), Biotinylation of Antibodies. In: Oliver C. and Jamur M. (eds) Immunocytochemical Methods and Protocols. Methods in Molecular Biology (Methods and Protocols), vol 588. Humana Press. Biotinylation of clinical grade commercially available monoclonal antibody is carried using methods known in the art or using commercially available biotinylated monoclonal antibodies against cancer associated antigens (e.g., CD20, CD19, CD38, GD2, Her2/neu or against any other known cancer associated cell-surface antigen), or against any undesirable normal or abnormal cells. Clinical grade NeutrAvidin or StreptAvidin or any other Avidin described above is used to connect biotin-containing antibodies.

Example 2: Producing Conjugated IMACs by a Variety of Biotinylated Monoclonal Antibodies A biotinylated monoclonal antibody against CD20 (e.g., Rituximab, MabThera) and a second biotinylated monoclonal anti-CD3 antibody are mixed in equal concentrations, aiming for 50:50 binding to NeutrAvidin to create an IMAC that can be suitable for treatment of any CD20 positive B cell malignancy, acute or chronic lymphocytic leukemia or NHL.

Such IMAC can be mixed with donor lymphocytes containing both T cells and NK cells in vivo or with donor lymphocytes pre-activated ex vivo for a minimum of 4-5 days with an activating agent such as IL-2.

Example 3: Confirming Superior Anti-Cancer Cytotoxicity of Mismatched Activated Killer Cells Targeted by IMAC Complexed with Biotinylated Anti-CD3 & Anti-CD20 Monoclonal Antibodies to Avidin Against Multiple Myeloma and Ramos Lymphoma Cells Even at Very Low Effector:Target Cell Ratio The objective of this study was to evaluate the efficacy of avidin-based IMAC targeting against different types of malignant cells.

Test System

Part I: Cell Lines:

Six human hematological malignant cell lines, all obtained from American Type Culture Collection (ATCC), Manassas, VA, USA:

Multiple Myeloma (MM):
- U266B1 [U266] (ATCC® TIB-196™) B lymphocyte, Plasmacytoma; Myeloma
- RPMI 8226 (ATCC® CCL-155™) B lymphocyte, Plasmacytoma; Myeloma
- MM.1R (ATCC® CRL-2975™) B lymphoblast, Multiple myeloma Lymphoma/Leukemia:
- Raji (ATCC® CCL-86™) B lymphocyte, Burkitt's lymphoma
- Ramos (RA 1) (ATCC® CRL-1596™) B lymphocyte, Burkitt's lymphoma
- Daudi (ATCC® CCL-213™) B lymphoblast, Burkitt's lymphoma Antibodies for Part I:
- CD20 Monoclonal Antibody (2H7), Biotin, eBioscience™, 100 μg (Thermo Fisher, Waltham, MA USA, Catalog #13-0209-82)
- CD38 Monoclonal Antibody (HIT2), Biotin, eBioscience™, 100 μg (Thermo Fisher, Waltham, MA USA, Catalog #13-0389-82)
- Mouse IgG2b kappa Isotype Control (eBMG2b), Biotin, eBioscience™, 500 μg (Thermo Fisher, Waltham, MA USA, Catalog #13-4732-85)
- Mouse IgG1 kappa Isotype Control (P3.6.2.8.1), Biotin, eBioscience, 500 μg (Thermo Fisher, Waltham, MA USA, Catalog #13-4714-85)
- Fluorescein (FITC)-conjugated IgG Fraction Monoclonal Mouse Anti-Biotin, 500 μg (Jackson ImmunoResearch Laboratories, Inc., West Grove, PA, USA, Catalog #200-092-211)

Antibodies for Part II:
- CD20 Monoclonal Antibody (2H7), Biotin, eBioscience™, 100 μg (Thermo Fisher, Waltham, MA USA, Catalog #13-0209-82)
- CD38 Monoclonal Antibody (HIT2), Biotin, eBioscience™, 100 μg (Thermo Fisher, Waltham, MA USA, Catalog #13-0389-82)
- CD3 Monoclonal Antibody (OKT3), Biotin, eBioscience™, 100 μg (Thermo Fisher, Waltham, MA USA, Catalog #13-0037-82)
- CD4 Monoclonal Antibody (RPA-T4), Biotin, eBioscience™, 100 μg (Thermo Fisher, Waltham, MA USA, Catalog #13-0049-82)
- CD8 Monoclonal Antibody (MEM-31), Biotin, 100 μg (Thermo Fisher, Waltham, MA USA, Catalog #MA1-19484)
- NeutrAvidin Protein, 10 mg (Thermo Fisher, Waltham, MA USA, Catalog #31000)
- Proleukin 18 MIU (Human IL-2): Powder for solution for injection or infusion Flow Cytometry Antibodies of Part I:

Anti-human CD3 PE (Biogems, Westlake Village, CA USA, Cat #05131-60-100)

Anti-human CD8a PerCP-Cyanine5.5 (Biogems, Westlake Village, CA USA, Cat #10121-70-100)

Anti-human CD4 APC (Biogems, Westlake Village, CA USA, Cat #06111-80-100)

Anti-human CD20 FITC (Invitrogen, Carlsbad, CA, United States, Cat #MA1-19613)

Anti-human CD38 FITC (Invitrogen, Carlsbad, CA, United States, Cat #MA1-12112)

Viobility 405/452 (Miltenyi Biotech, Bergisch Gladbach, Germany, Cat #130-109-816)

Cell Culture Materials

RPMI-1640 medium (Biological Industries, Beit-HaEmak, Israel, Catalogue #01-100-1A)

Fetal Bovine Serum (FBS, Biological Industries, Beit-HaEmak, Israel, Catalogue #04-007-1A)

Penicillin-Streptomycin solution (Biological Industries, Beit-HaEmak, Israel, Catalogue #03-031-1B).

Phosphate—Buffered Saline (PBS, Biological Industries, Beit-HaEmak, Israel, Catalogue #02-023-1A)

β-mercaptoethanol (Sigma Aldrich, Rehovot, Israel, Catalogue #M6250).

Trypan Blue (Sigma Aldrich, Rehovot, Israel, Catalogue #T8154).

Binding Test:

Cells were maintained according to Pharmaseed's SOPs 400, 401, 402 and 403, and manufacturer's instructions. On the day of cell staining with the antibodies, each cell line was counted and seeded at $1\times10^6$ cells/well in a 96 U shape plate. The plate was centrifuged (1500 rpm, 5 minutes, 4° C.) and the cells were resuspended with FACS buffer/Isotype control/Antibody. The cells were then incubated on ice for 30 minutes. The plates were centrifuged (1500 rpm, 5 minutes, 4° C.), medium was discarded, and the cells were resuspended with secondary antibody at 100 μL/well. The cells were incubated on ice for 30 minutes. Then, the plates were centrifuged (1500 rpm, 5 minutes, 4° C.), medium was discarded, and the cells were resuspended with 200 μL flow cytometry buffer and CD20 and CD38 expression was analyzed by FACS. One Multiple Myeloma and one Lymphoma/Leukemia cell line with the highest expression of CD38 and CD20, respectively, was chosen for PART II.

Part II— Efficacy Study

PBMCs Isolation and Preparation for Killing:

Human venous blood (10-15 mL) was collected to heparinized vials and mixed well by gently inverting the tube several times.

The blood was diluted ×2 with PBS.

Histopaque was added to a 50 mL centrifuge tube in half of the final blood:PBS volume.

The blood was gently layered on the top of Histopaque using a 1 mL auto pipette. The layering was done very slowly that blood and Histopaque stayed as two different layers.

The tubes were centrifuged (without any delay) at 400×g for 30 min in +20° C. in a swing-out bucket without break.

The whitish buffy coat (PBMCs) formed in the interphase between Histopaque and medium was aspirated without any delay.

The cells were washed (centrifuged in 800× g for 10 min in +20° C.) twice with 10 mL of PBS.

PBMCs were incubated at $2\times10^6$ cells/mL with Recombinant human IL-2 (6,000 IU/ml) for 6 days in PBMCs killer medium.

Assay Set Up (Day of End of Incubation Period of PBMCs with IL-2):

MM (RPMI2886) and Lymphoma/Leukemia (Ramos) cell lines were maintained according to Pharmaseed's SOPs 400, 401, 402 and 403, and manufacturer's instructions.

The cells were collected, washed in PBS, counted and adjusted to $0.2\times10^6$ cells/mL in PBS, each.

The cells were added to wells at 100 μL (20,000 cells/well)

Plates were centrifuged, PBS was discarded and 50 μL Ab/Ab-avidin was added.

The plates were incubated on ice for 1 h.

PBMCs were centrifuged (1,200 rpm, 15 minutes), medium was removed, and the cells were washed once again with PBS.

PBMCs were resuspended in 1 ml PBMCs culture medium and counted with trypan blue.

PBMCs were adjusted to $0.4\times10^6$ cells/mL, $2\times10^6$ cells/mL, and $8\times10^6$ cells/mL, and added at 50 μL, yielding 20,000 PBMCs/well, 100,000 PBMCs/well and 400,000 PBMCs/well, respectively.

The plated were incubated in 37° C. 5% $CO_2$ for 24 h.

Cell Counting and Flow Cytometry Analysis

At the end of incubation period, cells were counted with Trypan blue (one well/replicate).

Multiple Myeloma plates were stained with CD38, CD3, CD4, CD8 Abs, and viability dye.

Lymphoma plates were stained with CD20, CD3, CD4, CD8 Abs, and viability dye.

Samples were analyzed by FACS.

Formulation of the Test Items and Vehicle

Cell Lines Culture Medium:

RPMI-1640 medium supplemented with 10% FBS, and 1% Penicillin-Streptomycin solution.

Flow Cytometry Buffer:

PBS supplemented with 2% FBS.

PBMCs Culture Medium:

RPMI-1640 medium supplemented with 10% FBS, 0.05 μM β-mercaptoethanol, and 1% Penicillin-Streptomycin solution.

PBMCs Killer Medium:

RPMI-1640 medium supplemented with 10% autologous heat inactivated serum, 0.05 μM β-mercaptoethanol, and 1% Penicillin-Streptomycin solution.

Antibodies' Working Concentrations for Part I (in Flow Cytometry Buffer):

CD38 Monoclonal Antibody (0.5 μg/test/100 μL)

Mouse IgG1 kappa Isotype Control (0.25 μg/test/100 μL)

CD20 Monoclonal Antibody (0.25 μg/test/100 μL)

Mouse IgG2b kappa Isotype Control (0.125 μg/test/100 μL)

FITC—Mouse Anti-Biotin (1 μL/test/100 μL

Antibodies' Working Concentrations for Part II (in Flow Cytometry Buffer):

Anti-human CD3 PE (5 μl/test/100 μL)

Anti-human CD8a PerCP-Cyanine5.5 (5 μl/test/100 μL)

Anti-human CD4 APC (5 μl/test/100 μL)

Anti-human CD20 FITC (5 μl/test/100 μL)

Anti-human CD38 FITC (5 μl/test/100 μL)

Viobility™ 405/452 (1 μl/test/100 μL)

NeutrAvidin Protein:

NeutrAvidin Protein was reconstituted with 1 ml ultrapure water+9 ml PBS. The specific activity for biotin binding was approximately 14 μg/mg of protein.

Mm Ab Complex:

2.8 μg CD38 Ab (5.6 μl)+2.8 μg CD3 Ab (5.6 μl)+2.8 μg CD4 Ab (5.6 μl)+2.8 μg CD8 Ab (2.8 μl) in 800 μl PBS.

MM Avidin-Ab Complex:

5.25 μg CD38 Ab (10.5 μl)+5.25 μg CD3 Ab (10.5 μl)+5.25 μg CD4 Ab (10.5 μl)+5.25 μg CD8 Ab (5.25 μl) in 1500 μl PBS.

Lymphoma/Leukemia Ab Complex:

2.8 μg CD20 Ab (5.6 μl)+2.8 μg CD3 Ab (5.6 μl)+2.8 μg CD4 Ab (5.6 μl)+2.8 μg CD8 Ab (2.8 μl) in 800 μl PBS.

Lymphoma/Leukemia Avidin-Ab Complex:

5.25 μg CD20 Ab (10.5 μl)+5.25 μg CD3 Ab (10.5 μl)+5.25 μg CD4 Ab (10.5 μl)+5.25 μg CD8 Ab (5.25 μl) in 1500 μl PBS.

Results

Part I: Binding Test

As seen in Table 1, among all three Lymphoma cell lines, Ramos exhibited the highest CD20 expression (and also CD38 expression). Among all three Multiple myeloma cell lines, RPMI8226 exhibited the highest CD38 expression. These cell lines were chosen for part II.

Figure 5A:
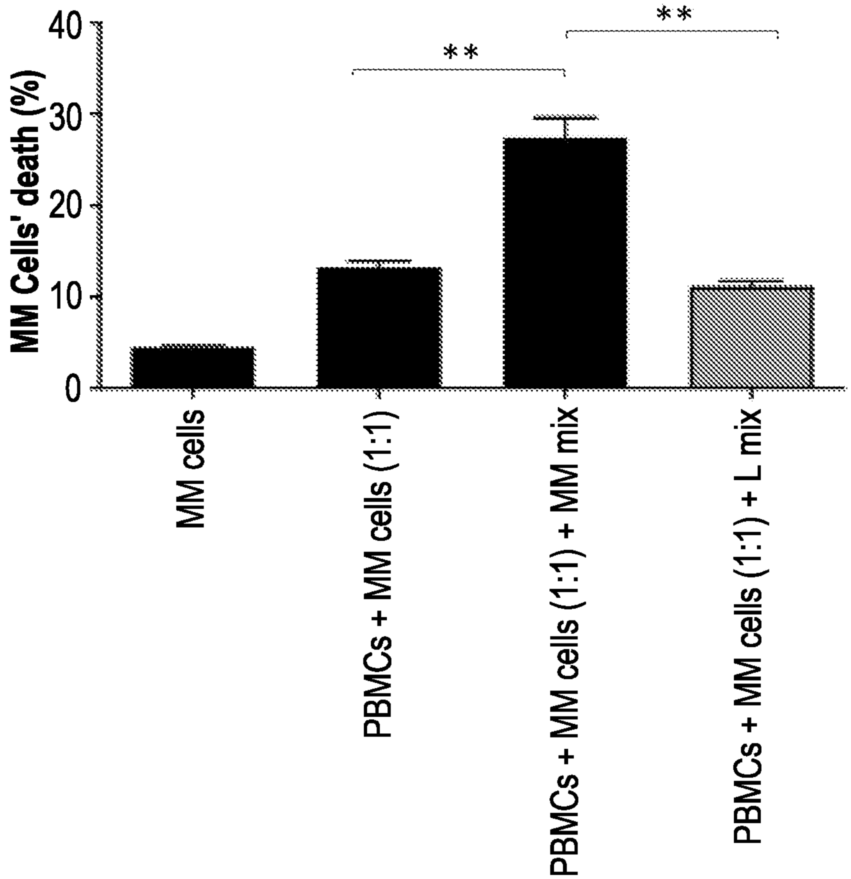
FIGS. 5A-5B. Cytotoxicity of IMAC against multiple myeloma cells after incubation for 24 hours.

As can be seen in FIG. 5A, cytotoxicity against multiple myeloma by IMAC was statistically significantly more effective as compared with the same monoclonal antibodies mixture not connected to avidin. The efficacy of IMAC containing anti-CD38 antibodies is striking considering the fact that even the lowest target:effector cell ratio of 1:1 showed impressive cytotoxicity against multiple myeloma cells. Since multiple myeloma also expressed CD20, some cytotoxicity against multiple myeloma cells were also observed with antibody mixture containing anti-CD20, but statistically inferior to antibody mixture containing anti-CD38 antibodies.

Figure 5B:
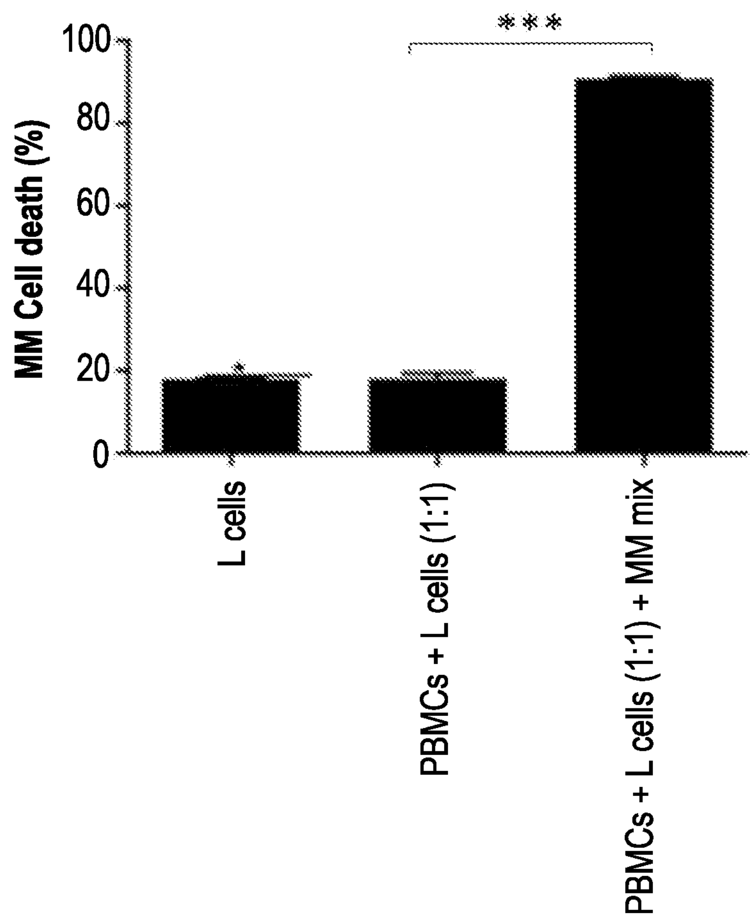

As can be seen in FIG. 5B, cytotoxicity against Ramos lymphoma by IMAC was statistically significantly more effective as compared with identical monoclonal antibodies mixture not connected to avidin. The cytotoxic efficacy of IMAC containing anti-CD38 antibodies is striking considering the fact that even the lowest effector:target cell ratio of 1:1 showed impressive cytotoxicity.

TABLE 1

Part I flow cytometry analysis*

| Cell type | Cell line | NS | CD20 | CD20 iso | CD38 | CD38 iso | CD20 expression | CD38 expression |
|---|---|---|---|---|---|---|---|---|
| Lymphoma | Daudi | 86 | 15148 | 621 | 32623 | 10183 | 24.4 | 3.2 |
| | Raji | 96 | 8391 | 201 | 26559 | 237 | 41.7 | 112.1 |
| | Ramos | 72 | 12163 | 147 | 26233 | 188 | 82.7 | 139.5 |
| Multiple | RPM18226 | 142 | 379 | 232 | 13008 | 254 | 1.6 | 51.2 |
| Myeloma | U2661B | 101 | 180 | 174 | 6691 | 199 | 1.0 | 33.6 |
| | MM1R | 111 | 198 | 174 | 3807 | 186 | 1.1 | 20.5 |

*CD20 MFI/CD20 isotype MFI = CD20 expression, CD38 MFI/CD38 isotype MFI = CD38 expression.

Part II: Efficacy Study

As seen in FIGS. 5A-5B, when comparing to untreated MM cells:

- Addition of both complexes of Avidin+MM or Lymphoma Abs increased cell death by ~1-2%.
- Addition of PBMCs 1:1 increased cell death by ~9%.
- Addition of PBMCs 1:1+Avidin+L Ab increased cell death only by ~6%.
- Addition of PBMCs 1:1+Avidin+MM Ab increased cell death by ~23% (significant increase compared to two previous treatments).

As seen in FIG. 5B, when comparing to untreated Lymphoma cells:

- Addition of avidin+MM Ab complex severely increased cell death (almost 100% dead cells).
- Addition of avidin+L Ab complex did not affect cells' viability.
- Addition of PBMCs 1:1 did not affect cells' viability.
- Addition of PBMCs 1:1+Avidin+L Ab did not affect cells' viability.
- Addition of PBMCs 1:1+Avidin+MM Ab severely increased cell death (almost 100% dead cells), similarly to control (complex only, without PBMCs).

Summary and Conclusions

As shown in FIGS. 5A and 5B, multiple myeloma (RPMI8226) and lymphoma (Ramos) cells lines with highest CD38 and CD20 expression, respectively, were incubated for 24 hours with various combinations of biotinylated anti-CD38 and anti-CD20 antibodies alone or biotinylated antibodies complexed with avidin and IL-2 activated lymphocytes in order to determine the efficacy of cytotoxicity against multiple myeloma cells and Ramos lymphoma cell lines, respectively.

Example 4: Confirming Superior Anti-Cancer Cytotoxicity of Mismatched Activated Killer Cells Targeted by IMAC Complexed with Biotinylated Anti-CD3 & Anti-CD20 Monoclonal Antibodies to Avidin Against Daudi & Ramos Lymphoma Cells Even at Very Low Effector:Target Cells Ratio The objective of this study was to evaluate the efficacy of avidin-based IMAC targeting against different types of lymphoma cell lines expressing CD20.

Test System

Cell Lines

Two human malignant lymphoma cell lines, obtained from American Type Culture Collection (ATCC), Manassas, VA, USA:

Ramos (RA 1) (ATCC® CRL-1596™) B lymphocyte, Burkitt's lymphoma (American)

Daudi (ATCC® CCL-213™) B lymphoblast, Burkitt's lymphoma

Antibodies and Proteins for Binding Assay

CD20 Monoclonal Antibody (2H7), Biotin, eBioscience™, 100 μg (Thermo Fisher,

Waltham, MA USA, Catalog #13-0209-82) CD3 Monoclonal Antibody (OKT3), Biotin, eBioscience™, 100 μg (Thermo Fisher, Waltham, MA USA, Catalog #13-0037-82) CD4 Monoclonal Antibody (RPA-T4), Biotin, eBioscience™, 100 μg (Thermo Fisher, Waltham, MA USA, Catalog #13-0049-82) CD8 Monoclonal Antibody (MEM-31), Biotin, 100 μg (Thermo Fisher, Waltham, MA USA, Catalog #MA1-19484)

NeutrAvidin Protein, 10 mg (Thermo Fisher, Waltham, MA USA, Catalog #31000)

Proleukin 18 MIU (Human IL-2): Powder for solution for injection or infusion

Flow Cytometry Reagents:

Anti-human CD3 PE (Biogems, Westlake Village, CA USA, Cat #05131-60-100)

Anti-human CD56 Anti-Human CD56 (NCAM) (Biogems, Westlake Village, CA USA, Cat #08631-50-100)

Viobility 405/452 (Miltenyi Biotech, Bergisch Gladbach, Germany, Cat #130-109-816)

Vybrant™ DiD Cell-Labeling Solution (Thermo Fisher, Waltham, MA USA, Cat #V22887)

PFA 4% (for cell fixation after staining)

Cell Culture Material

RPMI-1640 medium (Biological Industries, Beit-HaEmak, Israel, Catalogue #01-100-1A)

Fetal Bovine Serum (FBS, Biological Industries, Beit-HaEmak, Israel, Catalogue #04-027-1A)

BIOTARGET™ serum free-medium (Biological Industries, Beit-HaEmak, Israel, Catalogue #05-080-1A)

L-Glutamine (Biological Industries, Beit-HaEmak, Israel, Catalogue #03-020-1B)

Penicillin-Streptomycin solution (Biological Industries, Beit-HaEmak, Israel, Catalogue #03-031-1B).

Phosphate—Buffered Saline (PBS, Biological Industries, Beit-HaEmak, Israel, Catalogue #02-023-1A)

β-mercaptoethanol (Sigma Aldrich, Rehovot, Israel, Catalogue #M6250).

Trypan Blue (Sigma Aldrich, Rehovot, Israel, Catalogue #T8154).

Experimental Design

PBMC Isolation and Preparation of Killer Cells

Human Venous blood (10-15 mL) from a healthy donor were collected to heparinized vials and mixed well by gently inverting the tube several times.

The blood was diluted ×2 with PBS.

Histopaque was added to a 50 mL centrifuge tube into half of the final blood:PBS volume.

The blood was gently layered on the top of Histopaque using a 1 mL auto pipette. The layering was done very slowly that blood and Histopaque stayed as two different layers.

The tubes were centrifuged (without any delay) at 400×g for 30 min at +20° C. in a swing-out bucket without break.

The whitish buffy coat (PBMCs) formed in the interphase between Histopaque and medium was aspirated without any delay.

The cells were washed (centrifuged in 800×g for 10 min at +20° C.) twice with 10 mL of PBS.

PBMCs were incubated at a concentration of $2\times10^6$ cells/mL with Recombinant human IL-2 (6,000 μl/ml) for six days.

Target Cells Labeling (One Day Prior to End of Incubation Period of PBMCs with IL-2):

Each target cell line was suspended at a density of 106/mL in serum-free RPMI-1640 medium.

Cell-labeling solution was added to the cells (5 μL per mL of cell suspension). Cells were mixed well, and incubated for 20 minutes at 37° C.

The labeled cells were centrifuged at 1500 rpm for 5 minutes, at room temperature.

The supernatant was removed, and the cells were gently resuspended in warm culture medium. This procedure was then repeated two more times.

Assay Set Up (Day of End of Incubation Period of PBMCs with IL-2):

Lymphoma/Leukemia cell lines were maintained according to Pharmaseed's SOPs No. 400, 401, 402 and 403, and manufacturer's instructions.

The cells were collected, washed in PBS, counted and adjusted to a concentration of $0.2\times10^6$ cells/mL in PBS, each.

The cells were added to wells at 100 μL (20,000 cells/well).

Plates were centrifuged, PBS was discarded and 50 μL Ab/Ab-avidin was added to wells.

The plates were incubated on ice for 1 h.

Plates were centrifuged, Ab/Ab-avidin was discarded and PBMCs or medium only were added.

PBMCs were centrifuged (1,200 rpm, 15 minutes, at RT), medium was removed, and the cells were washed once again with PBS.

PBMCs were resuspended in 1 mL PBMCs culture medium and counted with trypan blue.

PBMCs were adjusted to $10\times10^5$ cells/mL, $2\times10^5$ cells/mL, and $1\times10^5$ cells/mL, and added at 100 μL to indicated wells according to scheme in Table 1, yielding 100,000 PBMCs/well, 20,000 PBMCs/well and 10,000 PBMCs/well, respectively.

The plates were incubated in 37° C. 5% $CO_2$ for 2 h and 24 h (two plates for each time point).

Flow Cytometry Analysis

At the end of each incubation period, the plates were centrifuged, washed with PBS, and stained with CD3, CD56, and viability dye.

Each plate was fixated with PFA 4% and stored at 4° C. until FACS analysis (up to two days later).

Samples were analyzed by FACS for target cell viability at each treatment.

Formulations:

Cell lines culture medium: RPMI-1640 medium supplemented with 10% FBS, and 1% Penicillin-Streptomycin solution.

Flow cytometry buffer: PBS supplemented with 2% FBS.

Antibodies' working concentrations (in flow cytometry buffer):

Anti-human CD56 FITC (5 μL/test/100

Anti-human CD3 PE (5 μL/test/100

Viobility™ 405/452 (1 μL/test/100

PBMCs culture medium for killer cell formation: RPMI-1640 medium supplemented with 10% autologous serum (heat inactivated), 0.05 μM β-mercaptoethanol, and 1% Penicillin-Streptomycin solution.

PBMCs culture medium for incubation with Target cells: Serum free medium supplemented with, 0.05 μM β-mercaptoethanol, and 1% Penicillin-Streptomycin solution.

NeutrAvidin Protein: NeutrAvidin Protein was reconstituted with 1 mL ultrapure water+9 mL PBS. The specific activity for biotin binding is approximately 14 μg/mg of protein.

CD20+CD3+CD4+CD8 complex (40 samples): 7.7 μg CD20 Ab+7.7 μg CD3 Ab+7.7 μg CD4 Ab+7.7 μg CD8 Ab in 2.2 mL PBS.

CD20+CD3+CD4+CD8+Avidin complex (40 samples): 7.7 μg CD20 Ab+7.7 μg CD3 Ab+7.7 μg CD4 Ab+7.7 μg CD8 Ab in 2.2 mL suspended NeutrAvidin.

CD20+CD3 complex (40 samples): 15.4 μg CD20 Ab+15.4 μg CD3 Ab in 2.2 mL PBS.

CD20+CD3+Avidin complex (40 samples): 15.4 μg CD20 Ab+15.4 μg CD3 Ab in 2.2 mL suspended NeutrAvidin.

CD20 complex (40 samples): 30.8 μg CD20 Ab in 2.2 mL PBS.

CD20+Avidin complex (40 samples): 30.8 μg CD20 Ab in 2.2 mL suspended NeutrAvidin.

Avidin complex (40 samples): 2.2 mL suspended NeutrAvidin.

Results

The results of the experiments are shown in FIGS. 6-13. The cytotoxic efficacy of biotinylated antibodies against CD20 and T cells (equal mixture of anti-CD3, anti-CD4 & anti-CD8) attached to IL-2 activated lymphocytes containing T cells and NK cells complexed with avidin or reacting alone against CD20 positive lymphoma cells was determined at two incubation time points (2 and 24 hours) at very low effector:target cells ratio of 0.5:1, 1:1 and 5:1.

Figure 6:
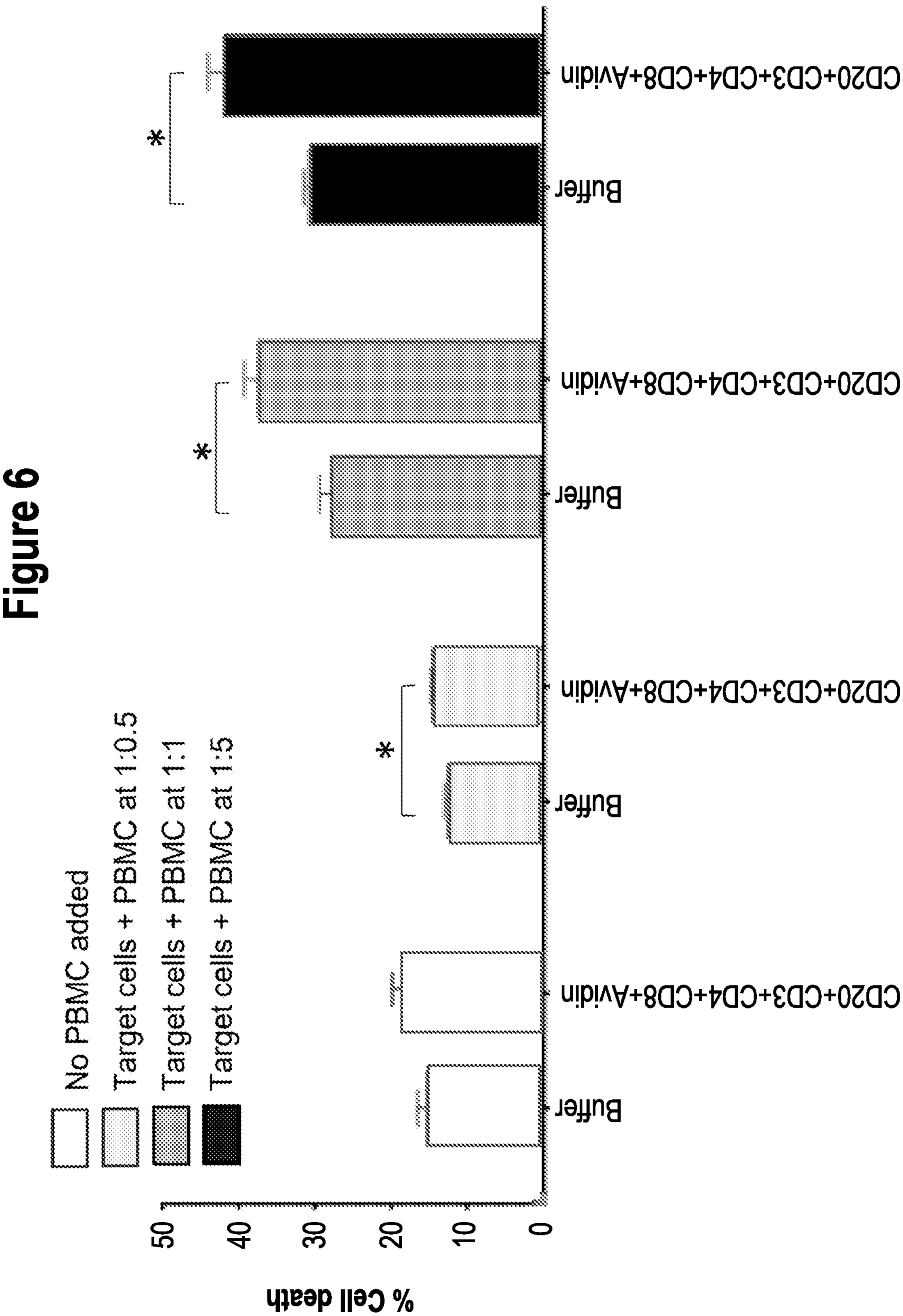
FIG. 6. Cytotoxicity of IMAC against Daudi lymphoma cells after incubation for 2 hours. Cytotoxicity of lymphoma (Daudi) cells after incubation for 2 hours with IL-2 activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells. Results represent means±SEM of wells in each group (*$p<0.05$ according to t-Test).

FIG. 6 shows gross cytotoxicity of Daudi cells after incubation for 2 hours with IL-2-activated lymphocytes targeted with biotinylated monoclonal antibodies against CD20 and T cells acting alone, or as IMAC complexed with avidin. Results represent means±SEM of wells in each group (*p<0.05 according to t-Test).

Figure 7:
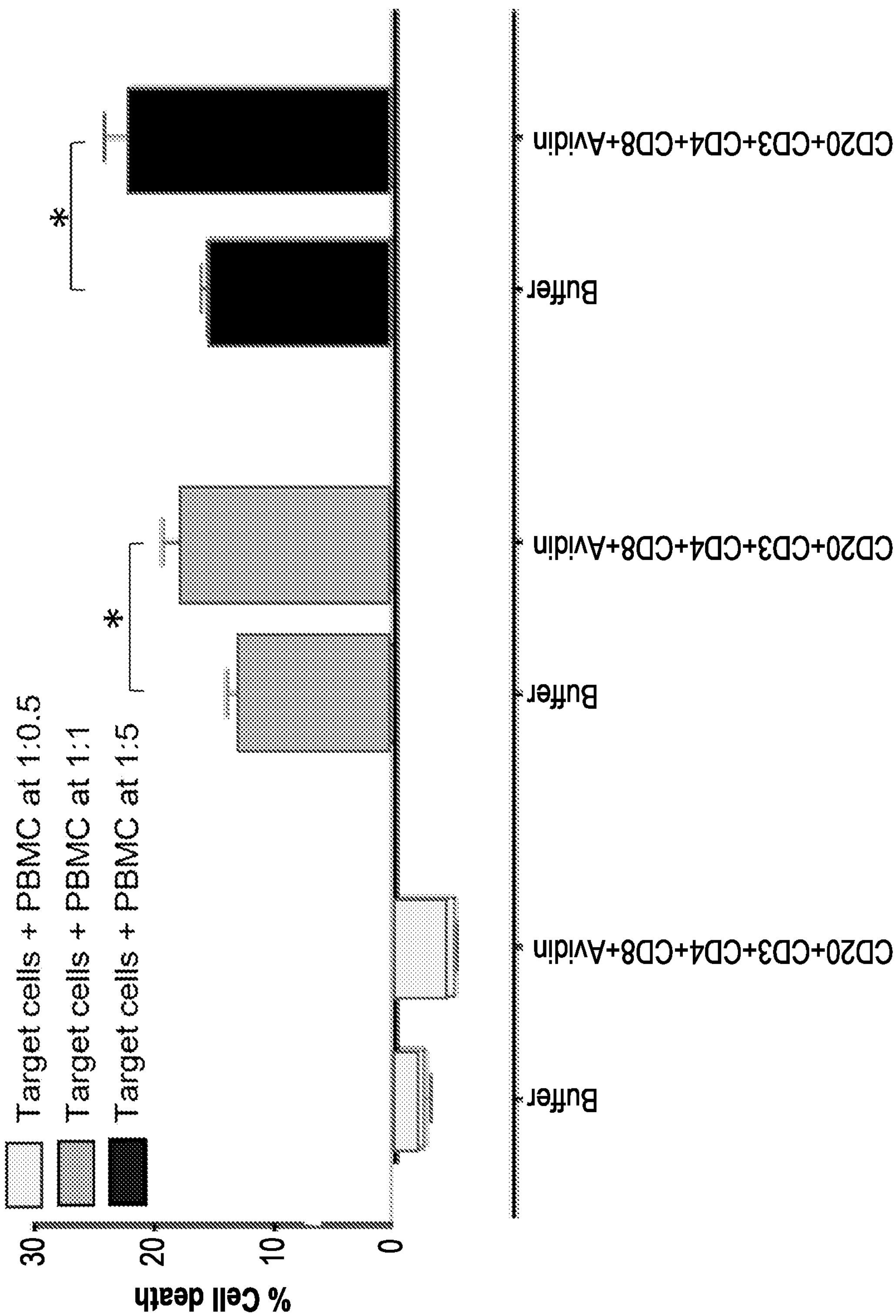
FIG. 7. Cytotoxicity of IMAC against Daudi lymphoma cells after incubation for 2 hours (−background cytotoxicity). Cytotoxicity of lymphoma (Daudi) cells after incubation for 2 hours with IL-2 activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells minus background cytotoxicity. Results represent means±SEM of wells in each group (*$p<0.05$ according to t-Test).

FIG. 7 shows net cytotoxicity of Daudi cells after incubation for 2 hours with IL-2-activated lymphocytes targeted with biotinylated monoclonal antibodies against CD20 and T cells acting alone, or as IMAC complexed with avidin. Results represent means±SEM of wells in each group (*p<0.05 according to t-Test).

Figure 8:
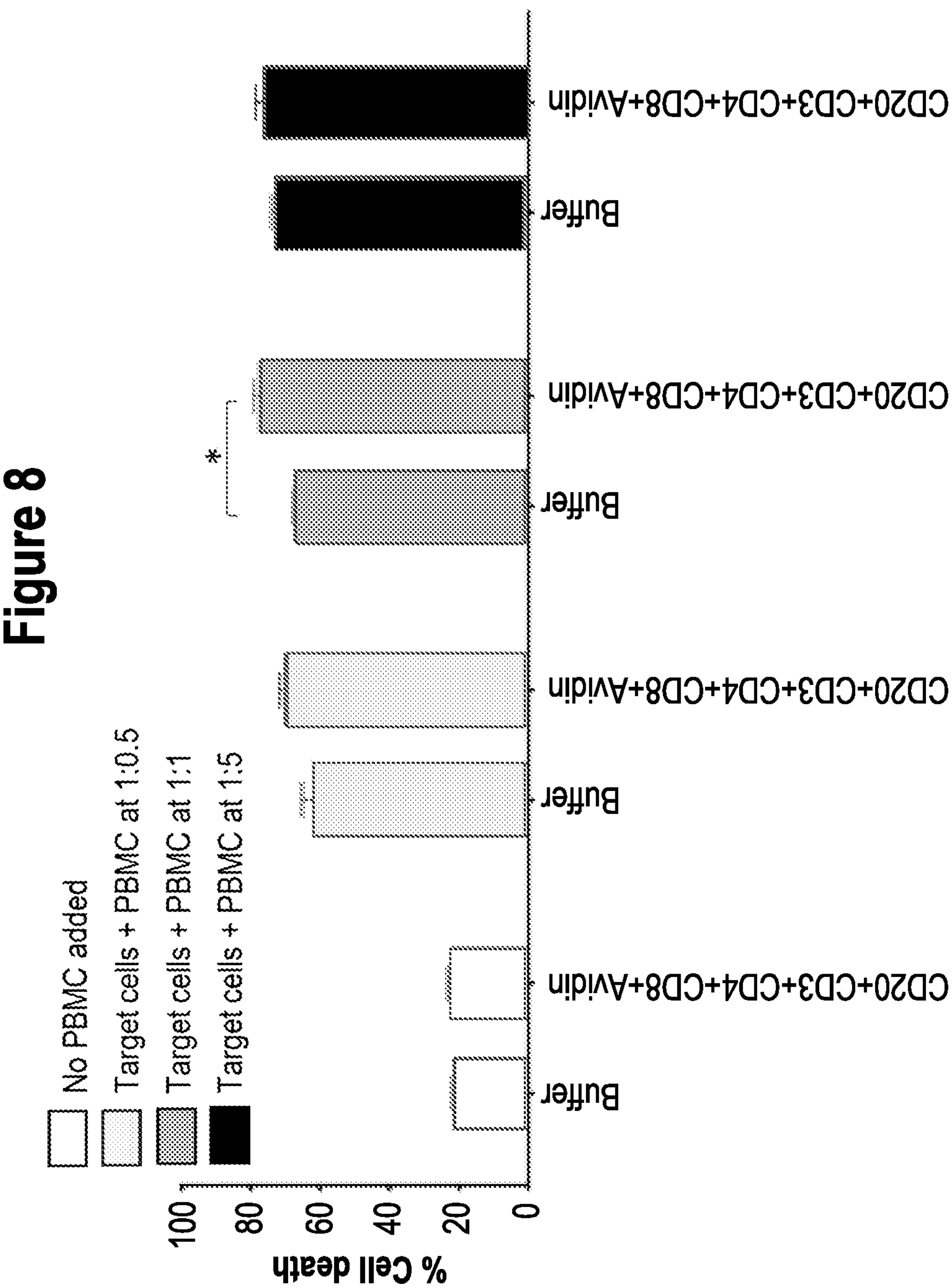
FIG. 8. Cytotoxicity of MAC against Daudi lymphoma cells after incubation for 24 hours. Cytotoxicity of lymphoma (Daudi) cells after incubation for 24 hours with IL-2-activated peripheral blood mononuclear cells, containing activated NK & T cells alone, or following targeting activated lymphocytes with biotinylated monoclonal antibodies against CD20, CD3, CD4 and CD8 complexed to avidin at an effector:target ratios of 0.5:1; 1:1 or 5:1 against CD20+ lymphoma cells. Results represent means±SEM of wells in each group (*$p<0.05$ according to t-Test).

FIG. 8 shows gross cytotoxicity of Daudi cells after incubation for 24 hours with IL-2-activated lymphocytes targeted with biotinylated monoclonal antibodies against CD20 and T cells acting alone, or as IMAC complexed with avidin. Results represent means±SEM of wells in each group (*p<0.05 according to t-Test).

Figure 9:
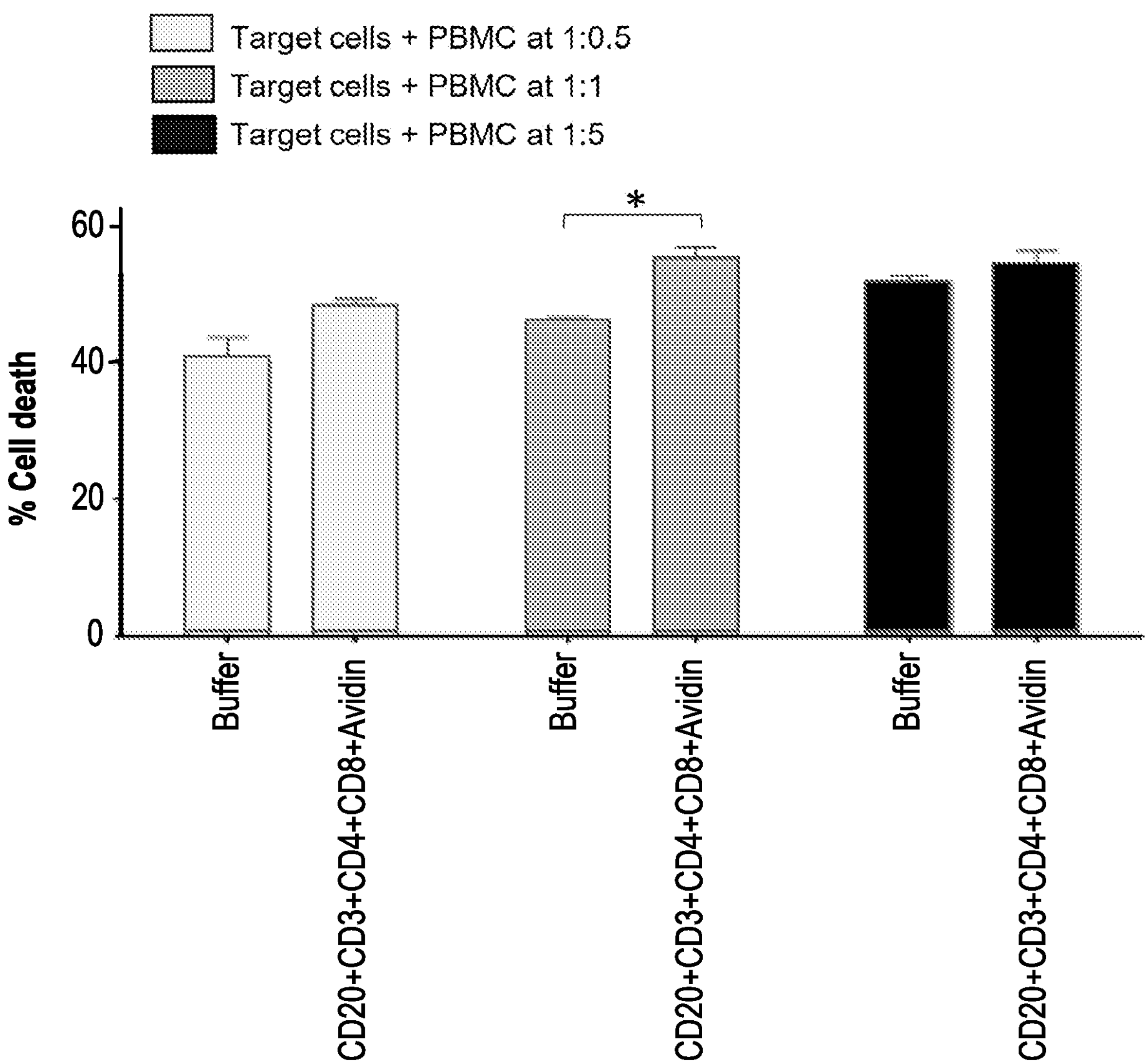
FIG. 9. Cytotoxicity of IMAC against Daudi lymphoma cells after incubation for 24 hours (−background cytotoxicity). Cytotoxicity of lymphoma (Daudi) cells after incubation for 24 hours with IL-2-activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells minus background cytotoxicity. Results represent means±SEM of wells in each group (*$p<0.05$ according to t-Test).

FIG. 9 shows net cytotoxicity of Daudi cells after incubation for 24 hours with IL activated lymphocytes targeted with biotinylated monoclonal antibodies against CD20 and T cells acting alone, or as IMAC complexed with avidin. Results represent means±SEM of wells in each group (*p<0.05 according to t-Test).

Figure 10:
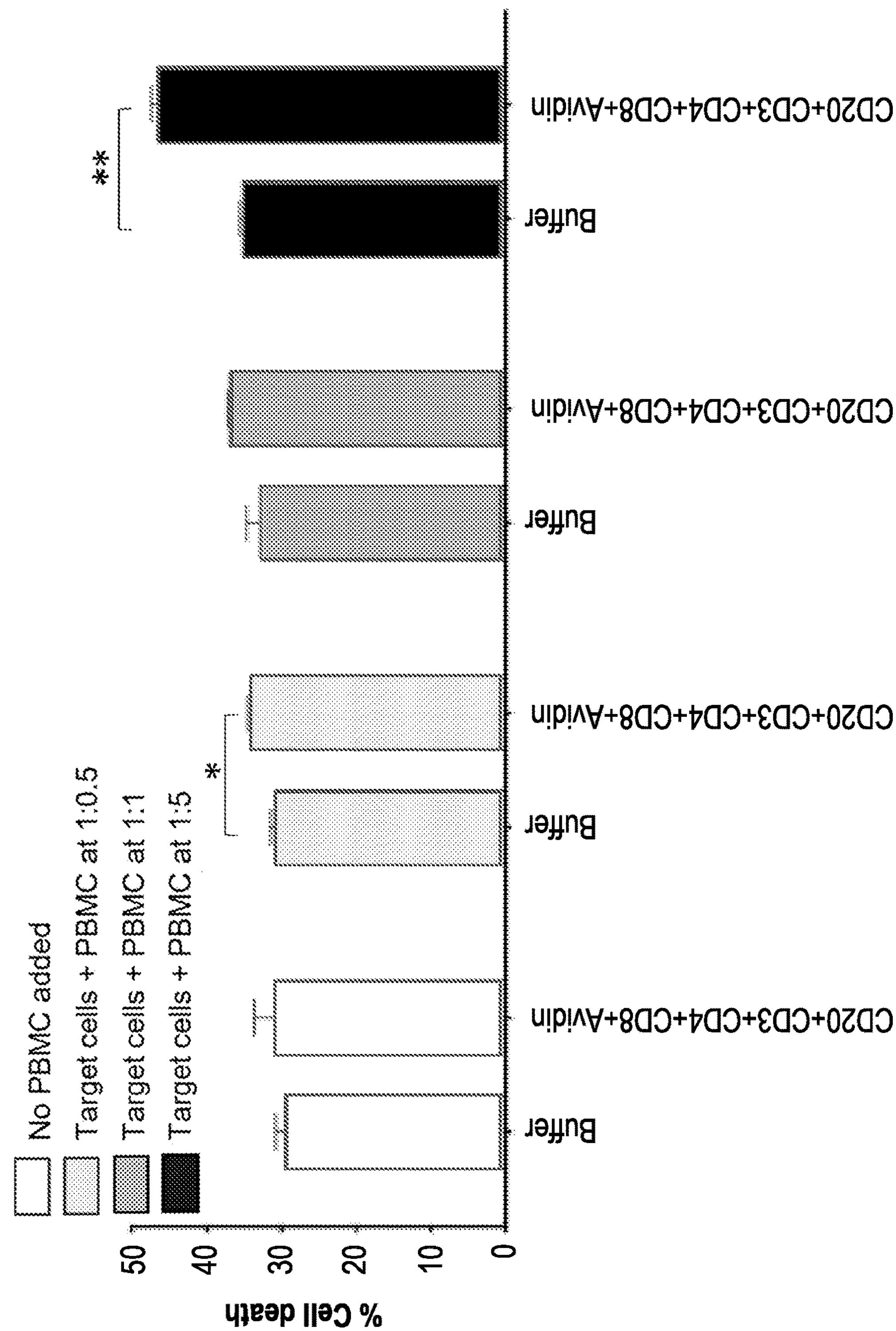
FIG. 10. Cytotoxicity of IMAC against Ramos lymphoma cells after incubation for 2 hours. Cytotoxicity of lymphoma (Ramos) cells after incubation for 2 hours with IL-2-activated peripheral blood Mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells. Results represent means±SEM of wells in each group (*$p<0.05$; **$p<0.01$ according to t-Test).

FIG. 10 shows gross cytotoxicity of Ramos cells after incubation for 2 hours with IL activated lymphocytes targeted with biotinylated monoclonal antibodies against CD20 and T cells acting alone, or as IMAC complexed with avidin. Results represent means±SEM of wells in each group (*p<0.05; **p<0.01 according to t-Test).

Figure 11:
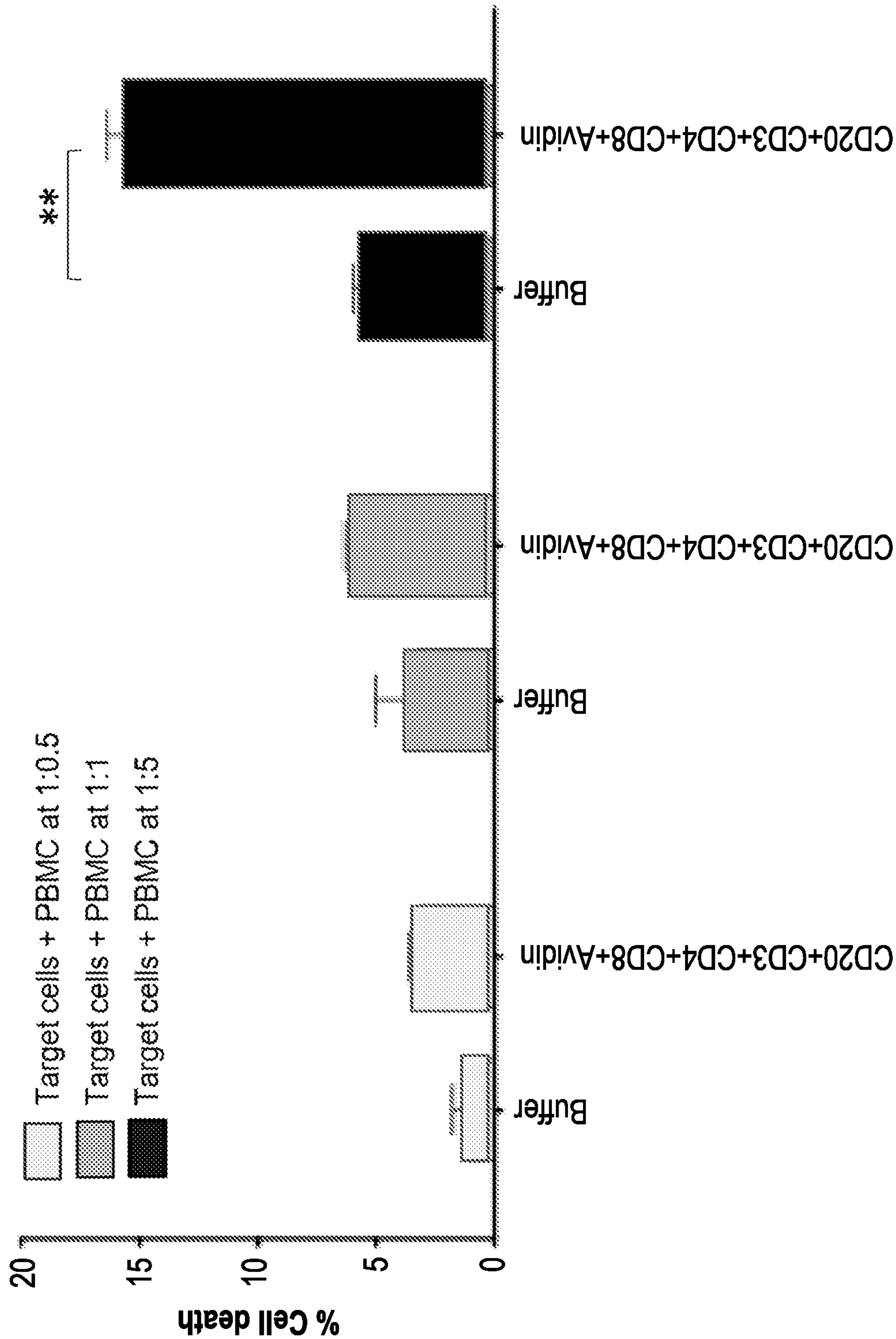
FIG. 11. Cytotoxicity of IMAC against Ramos lymphoma cells after incubation for 2 hours (−background cytotoxicity). Cytotoxicity of lymphoma (Ramos) cells after incubation for 24 hours with IL-2-activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells minus background cytotoxicity. Results represent means±SEM of wells in each group (**$p<0.01$ according to t-Test).

FIG. 11 shows net cytotoxicity of Ramos cells after incubation for 2 hours with IL-2-activated lymphocytes targeted with biotinylated monoclonal antibodies against CD20 and T cells acting alone, or as IMAC complexed with avidin. Results represent means±SEM of wells in each group (*p<0.05; **p<0.01 according to t-Test).

Figure 12:
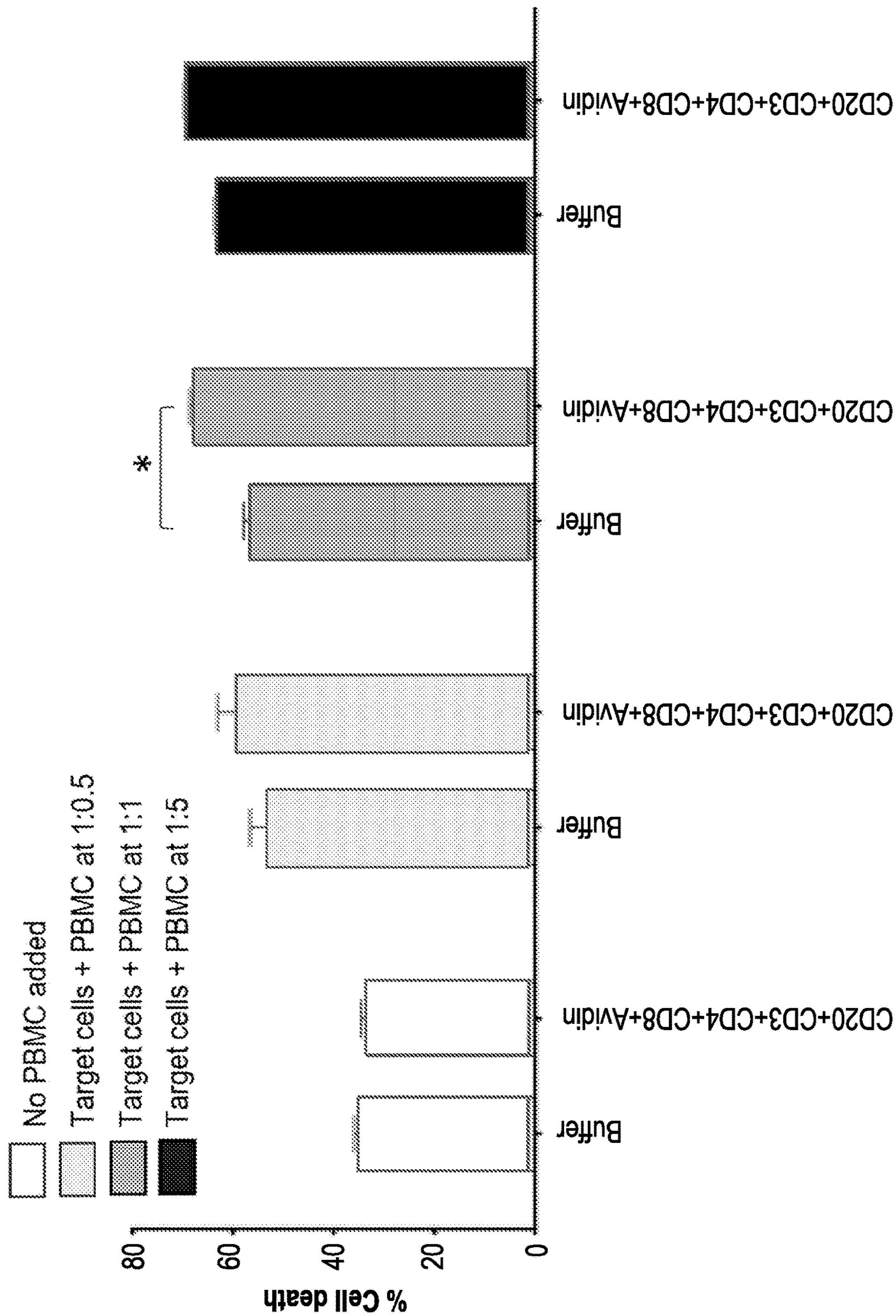
FIG. 12. Cytotoxicity of IMAC against Ramos lymphoma cells after incubation for 24 hours. Cytotoxicity of lymphoma (Ramos) cells after incubation for 24 hours with IL-2-activated peripheral blood Mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against CD20+ lymphoma cells. Results represent means±SEM of wells in each group (*$p<0.05$ according to t-Test).

FIG. 12 shows gross cytotoxicity of Ramos cells after incubation for 24 hours with IL-2-activated lymphocytes targeted with biotinylated monoclonal antibodies against CD20 and T cells acting alone, or as IMAC complexed with avidin. Results represent means±SEM of wells in each group (*p<0.05 according to t-Test).

Figure 13:
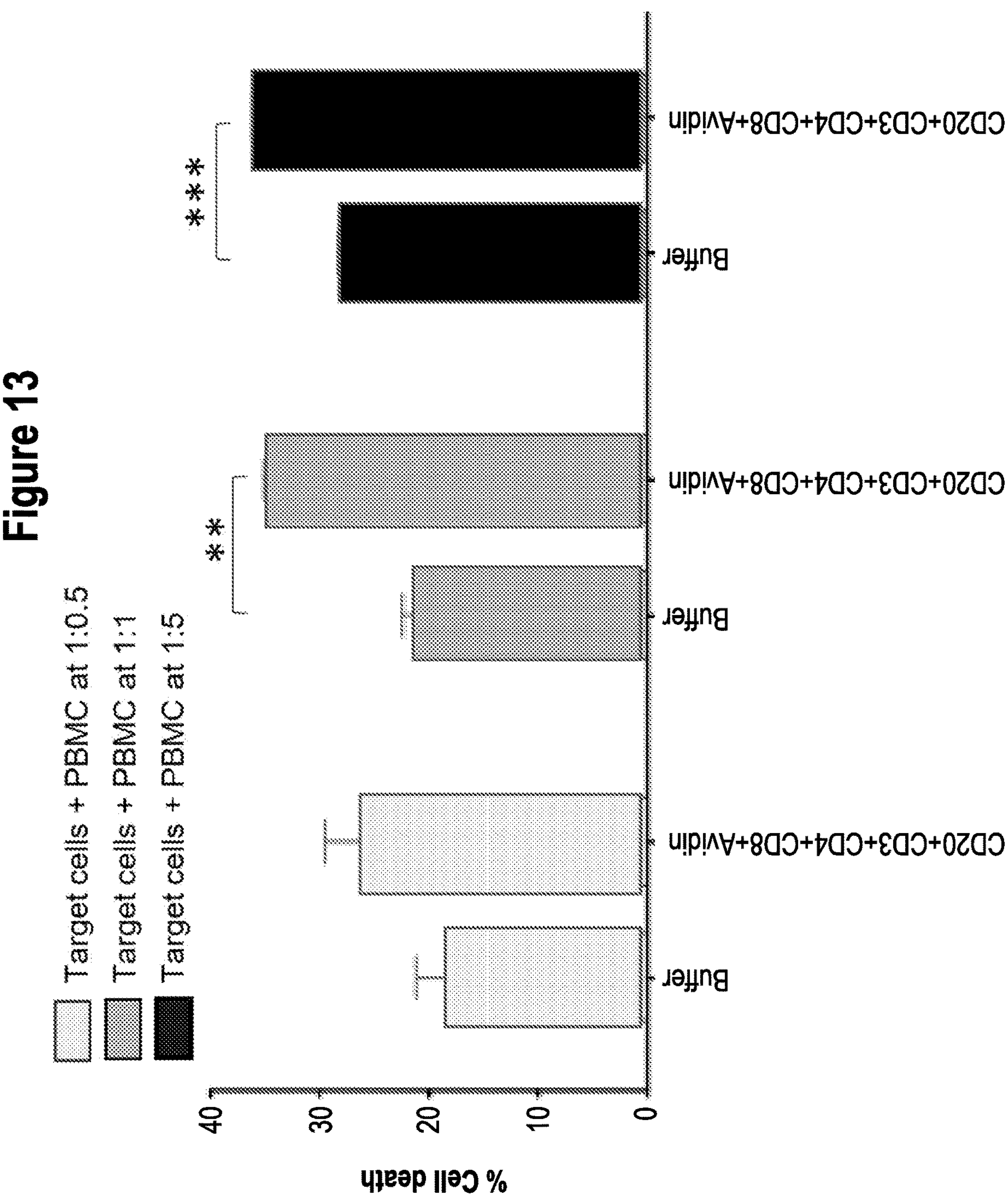
FIG. 13. Cytotoxicity of IMAC against Ramos lymphoma cells after incubation for 24 hours (−background cytotoxicity). Cytotoxicity of lymphoma (Ramos) cells after incubation for 24 hours with IL-2-activated peripheral blood mononuclear cells, containing activated NK & T cells alone, or following targeting activated lymphocytes with biotinylated monoclonal antibodies against CD20, CD3, CD4 and CD8 complexed to avidin at an effector:target cell ratios of 0.5:1; 1:1 or 5:1 against $CD20^+$ lymphoma cells minus background cytotoxicity. Results represent means±SEM of wells in each group ($p<0.01$; *$p<0.001$ according to t-Test).

FIG. 13 shows net cytotoxicity of Ramos cells after incubation for 24 hours with IL-2-activated lymphocytes targeted with biotinylated monoclonal antibodies against CD20 and T cells acting alone, or as IMAC complexed with avidin. Results represent means±SEM of wells in each group (p<0.01; *p<0.001 according to t-Test).

Summary and Conclusions

As can be seen in FIGS. 6-13, cytotoxicity against both Daudi and Ramos lymphoma cell lines by IMAC, when biotinylated monoclonal antibodies against CD20 and panel of T cells (CD3, CD4 & CD8) linked to IL-2 activated killer cells were complexed to avidin, cytotoxicity was statistically significantly more effective as compared with cytotoxicity induced by identical monoclonal antibodies mixtures linked to killer cells not connected to avidin. The superior cytotoxic efficacy of anti-CD20 guided IMAC as compared with the same components non-complexed to avidin is striking considering the fact that even at the lowest effector:target cell ratio of 0.5:1, and certainly at effector:target cell ratios of 1:1 and 5:1 cytotoxicity induced by IMAC at all combinations, both after 2 and 24 hours were statistically significant.

Example 5: Investigating the Use of IMAC Against Daudi Cells Targeting IL-2 Activated Lymphocytes with Monoclonal Antibody Against CD28

The objective of this study was twofold: [1] investigate the efficacy of anti-cancer cytotoxicity when IL-2 activated killer cells are guided by agonistic monoclonal anti-CD28 antibody instead of a mixture of classical anti-T cells antibodies (including CD3, CD4 & CD8); [2] compare the efficacy of 1-step anti-cancer cytotoxicity against Daudi cells by IMAC consisting of avidin linked to killer cells by biotinylated monoclonal antibodies against CD20 and CD28, compared with a 2-step procedure incubating anti-CD20 with Daudi cells first, followed by adding IL-2 activated lymphocytes linked to biotinylated anti-CD28 monoclonal antibody attached to avidin.

Test System

Cell Line

Daudi (ATCC® CCL-213™) B lymphoblast, Burkitt's lymphoma

Antibodies and Proteins for Binding Assay

CD28 Biotinylated (supplied by Sponsor)

Human CD20 (Rituximab) Biotinylated MAb (R&D, FAB9575B-100)

NeutrAvidin Protein, 10 mg (Thermo Fisher, Waltham, MA USA, Catalog #31000)

Proleukin 18 MIU (Human IL-2): Powder for solution for injection or infusion.

Flow Cytometry Reagents:

Viobility 405/452 (Miltenyi Biotech, Bergisch Gladbach, Germany, Cat #130-109-816)

Vybrant™ DiD Cell-Labeling Solution (Thermo Fisher, Waltham, MA USA, Cat #V22887)

PFA 4%

Cell-Culture Materials

RPMI-1640 medium (Biological Industries, Beit-HaEmek, Israel, Catalogue #01-100-1A).

Fetal Bovine Serum (FBS, Biological Industries, Beit-HaEmek, Israel, Catalogue #04-01A).

BIOTARGET™ serum free-medium (Biological Industries, Beit-HaEmek, Israel, Catalogue #05-080-1A).

L-Glutamine (Biological Industries, Beit-HaEmek, Israel, Catalogue #03-020-1B).

Penicillin-Streptomycin solution (Biological Industries, Beit-HaEmek, Israel, Catalogue #03-031-1B).

Phosphate—Buffered Saline (PBS, Biological Industries, Beit-HaEmek, Israel, Catalogue #02-023-1A).

β-mercaptoethanol (Sigma Aldrich, Rehovot, Israel, Catalogue #M6250).

Trypan Blue (Sigma Aldrich, Rehovot, Israel, Catalogue #T8154).

Experimental Design

PBMCs Isolation and Preparation of Killer Cells

Human venous blood (10-15 mL) from a healthy donor was collected to heparinized vials and mixed well by gently inverting the tube several times.

The blood was diluted ×2 with PBS.

Histopaque was added to a 50 mL centrifuge tube into half of the final blood:PBS volume.

The blood was gently layered on the top of Histopaque using a 1 mL auto pipette. The layering will be done very slowly in order that blood and Histopaque will stay as two different layers.

The tubes were centrifuged (without any delay) at 400×g for 30 min at +20° C. in a swing-out bucket without break.

The whitish buffy coat (PBMCs) formed in the interphase between Histopaque and medium were aspirated without any delay.

The cells were washed (centrifuged in 800×g for 10 min at +20° C.) twice with 10 mL of PBS.

PBMCs were reconstituted in serum free media and counted.

The cells were incubated at a concentration of $2\times10^6$ cells/mL with recombinant human IL-2 (6,000 IU/ml) for six days.

Target Cells Labeling (One Day Prior to End of Incubation Period of PBMCs with IL-2)

Daudi cells were suspended at a density of $10^6$/mL in serum-free RPMI-1640 medium.

Cell-labeling solution was added to the cells (5 μL per mL of cell suspension). The cells mixed well, and incubated for 20 minutes at 37° C.

The labeled cells were centrifuged at 1500 rpm for 5 minutes, at room temperature.

The supernatant was removed, and the cells were gently resuspended in warm culture medium. This procedure was then repeated two more times.

Assay Set Up (Day of End of Incubation Period of PBMCs with IL-2):

PBMCs were centrifuged (1200 rpm, 15 minutes, at RT), medium was removed, and the cells were washed once again with PBS.

PBMCs were resuspended in 1 mL PBS and counted with trypan blue.

PBMCs were adjusted to $4\times10^5$ cells/mL, $20\times10^5$ cells/mL, $40\times10^5$ cells/mL, and $80\times10^5$ cells/mL, and added at 50 μL to the wells, yielding 20,000 PBMCs/well, 100,000 PBMCs/well, 200,000 PBMCs/well, and 400,000 PBMCs/well respectively.

Plate was centrifuged; PBS was discarded and 50 μL PBS/Ab/Ab-avidin/avidin was added to indicated wells.

The plate was incubated on ice for 1 h.

Plate was centrifuged, PBS/Ab/Ab-avidin/avidin was discarded and Daudi cells (target cells) or medium only was added to the wells.

The cells were collected, washed in PBS, counted, and adjusted to a concentration of $2\times10^5$ cells/mL in PBS, each.

The cells were added to wells at 100 μL (20,000 cells/well).

The plate was then incubated in 37° C. 5% $CO_2$ for 6 h.

Flow Cytometry Analysis

At the end of incubation period, the plate was centrifuged (1500 rpm, 5 minutes, 4° C.), washed with PBS, and stained with viability dye.

The plate was fixated with Transcription Factor Fix/Perm reagent (Transcription Factor Fix/Perm Concentrate diluted ×4 in Transcription Factor Fix/Perm Diluent) and stored at 4° C. until FACS analysis (up to two days later).

Samples were analyzed by FACS for target cell viability.

Formulations

Cell lines culture medium: RPMI-1640 medium supplemented with 10% FBS, and 1% Penicillin-Streptomycin solution.

Flow cytometry buffer: PBS supplemented with 2% FBS.

Antibodies' working concentrations (in flow cytometry buffer):

Viobility™ 405/452 (1 μl/test/100 μL)

PBMCs culture medium for killer cell formation: RPMI-1640 medium supplemented with 10% autologous serum (heat inactivated), 0.05 μM β-mercaptoethanol, and 1% Penicillin-Streptomycin solution.

PBMCs culture medium for incubation with Target cells: Serum free medium supplemented with: 0.05 μM β-mercaptoethanol and 1% Penicillin-Streptomycin solution.

NeutrAvidin Protein: NeutrAvidin Protein is reconstituted with 1 ml ultrapure water+9 mL PBS. The specific activity for biotin binding is approximately 14 μg/mg of protein.

CD20+CD28 complex (12 samples): 5.25 μg CD20 Ab+5.25 μg CD28 Ab in 0.75 mL PBS.

CD20+CD28+Avidin complex (12 samples): 5.25 μg CD20 Ab+5.25 μg CD28 Ab in 0.75 mL suspended NeutrAvidin.

Avidin complex (12 samples): 0.75 mL suspended NeutrAvidin.

Results and Conclusions

Figure 14:
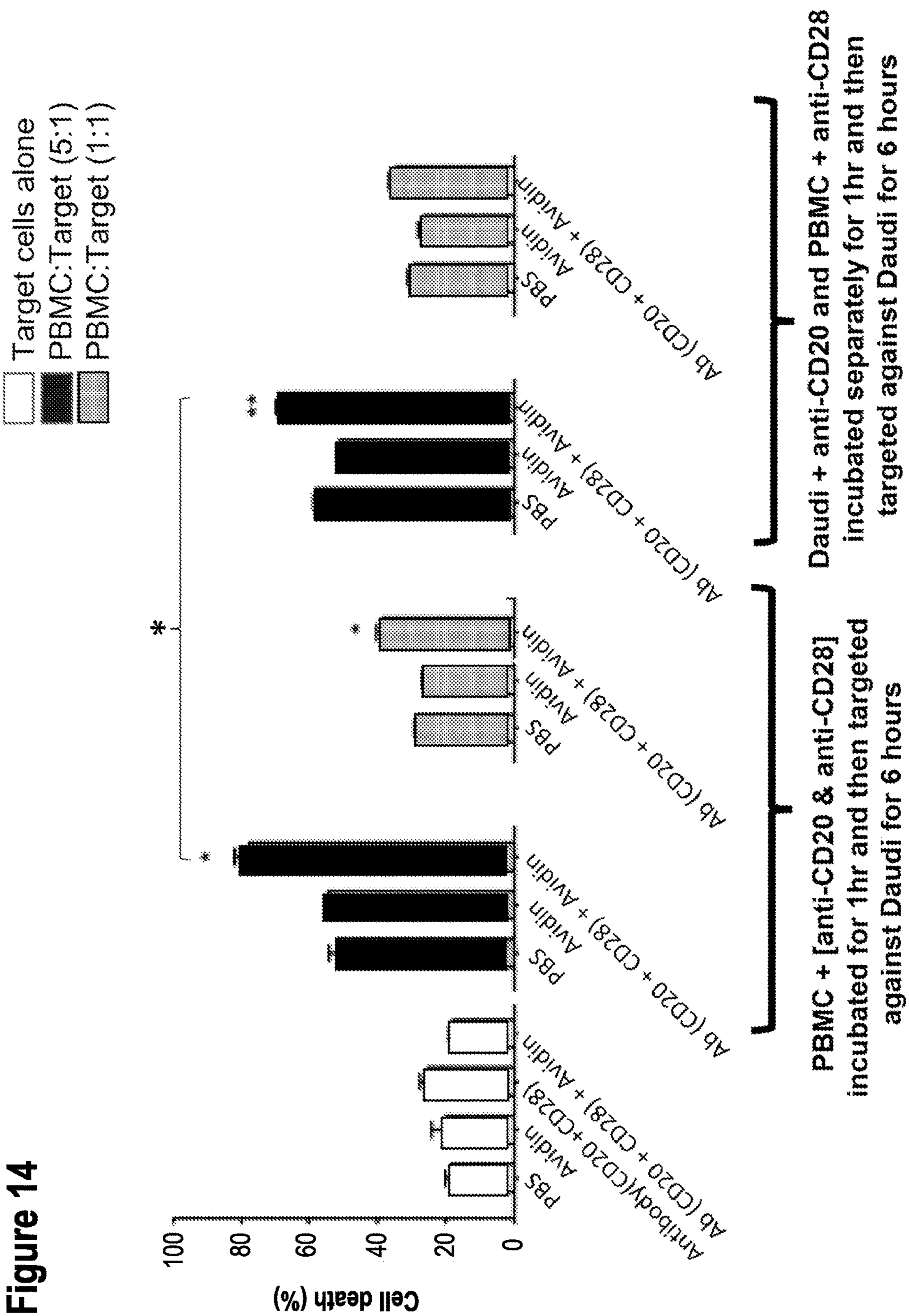
FIG. 14. Comparing uncorrected 1-step cytotoxicity against Daudi lymphoma cells by IMAC (avidin complexed with biotinylated antibodies against CD20 & anti-CD28 attached to IL-2 activated lymphocytes) as compared with 2-step cytotoxicity: first incubating biotinylated antibodies against CD20 with Daudi cells in parallel with separate incubation of IL-2 activated lymphocytes with biotinylated antibodies against CD28 attached to avidin and only then adding killer lymphocytes against Daudi cells.
Figure 15:
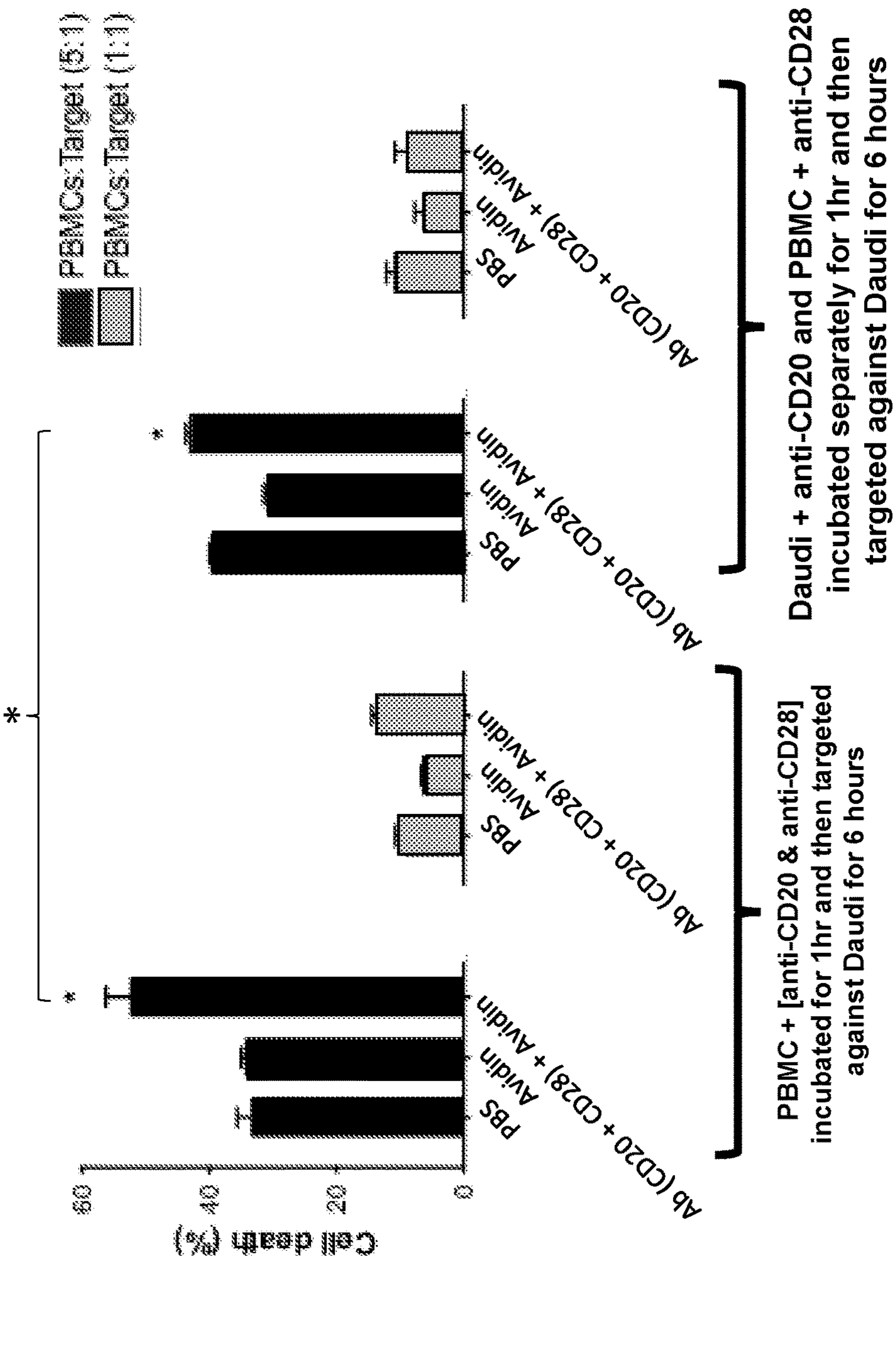
FIG. 15. Comparing net cytotoxicity of 2-step procedure against Daudi lymphoma cells by IMAC (avidin complexed with biotinylated antibodies against CD20 & anti-CD28 attached to IL-2 activated lymphocytes) as compared with 2-step net cytotoxicity: first incubating biotinylated antibodies against CD20 with Daudi cells in parallel with separate incubation of IL-2 activated lymphocytes with biotinylated antibodies against CD28 attached to avidin and only then adding killer lymphocytes against Daudi cells.

As can be seen in FIG. 14, featuring gross, and FIG. 15 featuring net cytotoxicity, induced by IMAC, guiding IL-2 activated lymphocytes with monoclonal antibody against CD28 against Daudi cells confirm remarkable anti-Daudi cells cytotoxicity at effector:target cell ratio of 5:1.

Comparing the efficacy of cytotoxicity induced by 1-step and 2-step IMAC indicated that both 1-step and 2-step anti-Daudi cytotoxicity were effective, yet 1-step cytotoxicity with IMAC attacking Daudi cells with both anti-CD20 and anti-CD28 complexed with avidin was statistically significantly better that 2-step approach. These results indicate the importance of avidin as an anchor for antibody complex formation favoring dual simultaneous attack of cancer cells by monoclonal antibodies linked to avidin.

Furthermore, the results of the experiments summarized in FIGS. 14 and 15 indicate that it may be possible to use IMAC complexes with different T cells targeting antibodies, including antibodies that could both target and activate effector T cells and NK cells.

Example 6: Optimizing the Anti-Cancer Effects of Mismatched Donor Lymphocytes by Maximal Pre-Treatment Activation of Donor Lymphocytes The purpose of the following experiments was to find out the most effective approach for stimulation of all effector cells that can participate in elimination of cancer cells. Human peripheral blood mononuclear cells (PBMC) were isolated as previously described and activated with interleukin 2 (IL-2) alone, phytohemagglutinin (PHA) alone, +α-GalactosylCeramide (KRN7000) alone, KRN7000+PHA, IL-2+KRN7000, and IL-2+KRN7000+PHA in comparison with untreated cells.

Experimental Design

PBMCs Isolation

Human Venous blood (~20-30 mL) from a healthy donor was collected to heparinized vials and mixed well by gently inverting the tube several times.

In addition, approximately 10 mL blood was collected into serum collection tubes.

The blood was diluted ×2 with PBS.

Ficoll-Paque was added at 15 mL max into a 50 mL centrifuge tube (1 tube per 8 mL blood collected was required).

The blood:PBS was gently layered on the top of Ficoll-Paque using a 1 mL auto pipette at 1:1 ratio with the Ficoll-Paque. The layering was done very slowly so that blood and Ficoll-Paque will stay as two different layers.

The tubes were centrifuged (without any delay) at 400 g for 30 min at +20° C. in a swing-out bucket without break.

First, the upper plasma layer was collected and dispensed.

Then, the whitish buffy coat (PBMCs) formed in the interphase between Ficoll-Paque and plasma was aspirated (and divided between several 50 mL tubes-per each 10 mL blood collected, use 1 tube).

The cells were washed (centrifuged in 400 g for 10 min at +20° C.) twice with 10 mL of PBS+2% FBS.

Finally, the cells were resuspended with 10 mL PBS+2% FBS and counted using trypan blue.

The PBMCs were centrifuged and adjusted to $1\times10^7$ cells/mL in ice cold freezing medium and placed in a cooled Mr. Frosty container (filled with isopropanol).

The container was placed in −80° C. for 24 hours and then the cells were moved to a liquid nitrogen container.

Heat Inactivated Serum Preparation:

The serum vials were placed in RT for at least 30 minutes.

Next, they were centrifuged at 4100 rpm, for 10 minutes, at 4° C.

The serum was then collected into a 15 mL tube and placed in 57° C. bath for 15 minutes.

After heat inactivation, it was aliquoted into 1 mL aliquots, and frozen at −80° C.

Main Assay Procedure:

PBMCs were thawed for 1 minutes in 37° C. bath and transferred immediately into 50 mL tube filled with PBS.

The tube was centrifuged at 300 g, 5 minutes, and the cells were resuspended with 1 mL activation medium and counted (diluted 1:10 and 1:2 with TB).

The cells were adjusted to $2\times10^6$ cells/mL with activation medium and placed in 24-well plate at 0.5 mL/well.

The cells were then activated.

Flow Cytometry Analysis:

At the end of incubation, PBMCs from each well were collected into Eppendorf tube, centrifuged at 300×g for 5 min in 4° C., washed once with 1 mL PBS, resuspended in 0.1 mL PBS and placed in a well of V shape 96 well plate.

The plate was centrifuged, and the cells were resuspended with 100 μL diluted viability dye.

The plate was incubated 30 min in RT (in dark).

The plate was centrifuged at 300×g for 5 min in 4° C., and cells were resuspended with 100 μL surface markers cocktail.

The plate was incubated 30 min on ice (in dark).

The plate was centrifuged at 300×g for 5 min in 4° C. and resuspended in 0.1 ml of the Transcription Factor Fixation/Permeabilization working solution and mixed thoroughly.

The plate was incubated 30 min on ice (in dark).

The plate was centrifuged, and Fixation Buffer was discarded.

The plate was washed twice with 0.1 mL 1× Permeabilization working solution (centrifuged at 300×g for 5 min in RT).

The plate was resuspended in 50 μL of 1× Permeabilization working solution +FoxP3 antibody.

The plate was incubated for 30 minutes at RT (in dark).

The plate was centrifuged (300 g, 5 minutes, 4° C.) and washed twice with 0.1 mL 1× Permeabilization working solution.

Finally, cells were resuspended in 150 μL FACS buffer for flow cytometric analysis.

Material and Formulations:

Flow cytometry buffer: PBS (Biological Industries, Cat #01-023-1A) supplemented with 2% FBS (Biological Industries, Cat #04-127-1A).

Activation medium: RPMI-1640 medium (Biological Industries, Cat #01-100-1A) supplemented with 10% autologous serum (heat inactivated), 0.05 mM β-mercaptoethanol (Sigma, Cat #M6250) and 1% Penicillin-Streptomycin solution (Biological Industries, Cat #03-031-1B).

PBMCs freezing medium: 90% FBS (Biological Industries, Cat #04-127-1A) and 10% DMSO (Sigma, Catalogue #D4540).

Ficoll-Paque™ PREMIUM (GH Healthcare, Catalogue #17-5442-02).

PHA (Sigma, Cat #L1668) was supplied at a stock concentration of 5 mg/mL. It was first diluted in activation medium 1:10 yielding 500 μg/mL. Thereafter 50 from 500 μg/mL stock was added to the cells and diluted 1:100 yielding final concentration of 5 μg/mL.

Proleukin 18 MIU (Human IL-2) is stored at a stock of $18\times10^6$ units/mL. First it was diluted 1:30 in activation medium yielding $0.6\times10^6$ units/mL. Thereafter 5 μl from $0.6\times10^6$ units/mL stock was added to cell and diluted 1:100 yielding final concentration of 6000 units/mL.

KRN7000 (0.2 mg/mL) dissolved in DMSO at 1 mg/mL (200 μL DMSO was added to 0.2 mg powder). First it was diluted 1:10 and 1:100 in activation medium yielding 100 and 10 μg/mL. Thereafter 5 μL from these two stocks was added to cells and diluted 1:100 yielding final concentrations of 1000 and 100 ng/mL.

Flow Cytometry Antibodies

Viability dye: LIVE/DEAD Fixable Aqua Dead Cell Stain Kit (Invitrogen, Cat #L34966) Dilute in PBS 1:1000.

Anti-Human CD3-BV421 (BD Bioscience, Cat #563798). 5 μL/100 μL FACS buffer (1:20).

Anti-Human CD4-PerCP-Cyanine5.5 (Biogems, Catalogue #06121-70). 5 μL/100 μL FACS buffer (1:20).

Anti-Human CD45-PE (Biogems, Catalogue #07151-60). 5 μL/100 μL FACS buffer (1:20).

Anti-Human FOXP3-Alexa Fluor 647 (Biogems, Catalogue #07151-60). 5 μL/100 μL FACS buffer (1:20).

Anti-Human CD56-FITC (Biogems, Catalogue #08631-50). 5 μL/100 μL FACS buffer (1:20).

Permeabilization Buffer Xl: Permeabilization Buffer X10 (Peprotech, cat #92110-00-150) will be diluted with distilled water to 1× prior to use.

Transcription Factor Fixation/Permeabilization working solution: will be prepare by mixing one part of the concentrate solution (cat #92550-00) with 3 parts of the diluent (cat #92160-00).

Results and Conclusions

Results of different methods for proliferation of CD45 positive mononuclear blood lymphocytes, CD3+ cells including CD3+CD56− T cells & CD3+CD56+ NKT cells, CD56+ NK cells, FOXP3+ regulatory T cells and consequently CD3+CD56+ NKT cells are shown in FIG. 16.

The highest number of effector cells can be obtained by culturing IL-2 activated PBMC at 6,000 IU/ml in combination with 100 ng/ml KRN7000 and 5 μg/ml PHA. Under the culture conditions combining IL-2, KRN7000 and PHA the number of activated T cells was the highest observed. In addition, the number of regulatory T cells was doubled as compared with lymphocytes cultured with IL-2 alone, so regulatory T cells could potentially better control any possible untoward cytokine reaction. The highest number of NK cells was also obtained by culturing PBMC with IL-2, 100-1,000 ng/ml KRN7000 and PHA. Mismatched NK cells exert fast and most effective cytotoxicity against MHC mismatched target cells.

Interestingly, adding KRN7000 to lymphocytes activated with IL-2 with or without PHA increased the number of NKT cells by 30% as compared with cells treated with IL-2 alone. Accordingly, NKT cells could also amplify the anticipated anti-cancer effects induced by donor lymphocytes activated by IL-2.

Example 7: Phase 1 Clinical Trial Using IMAC Alone Based on an Attempt to Activate Spontaneously Patient's Own Immune System In Vivo Against B Cell Malignant Diseases (CLL, ALL or NHL) and/or Multiple Myeloma IMAC comprising equal amounts of biotinylated anti-CD20 and anti-CD3 monoclonal antibodies connected through NeutrAvidin, or StreptAvidin is tested in 3 cohorts of patients with intractable B cell malignancies (CLL, ALL or NHL) for each dose of IMAC. Treatment with IMAC comprises graded increments of IMAC administered intravenously, starting with 1 μg and doubling the dose pending no restrictive CRS, allowing for no more than grade II toxicity in 2 of 3 patients. The maximally tolerated dose (MTD) is defined according to methods known in the art (for example references 22, 23) and Common Terminology Criteria for Adverse Events (CTCAE).

Similarly, a study is accomplished using IMAC composed of anti-CD38 and anti-CD3 (or any other monoclonal anti-T cell antibodies).

Initially an intra-patient IMAC dose finding will be carried out to check if any risk may be involved by injection of IMAC and for finding the maximal tolerated dose (MTD) of IMAC that will used in subsequent studies. Dose escalation will be carried out as follows:

- The first 3 patients will be treated with 1 μg IMAC administered intravenously.
- Pending lack of CRS in all 3 patients, IMAC dose will be escalated to 2 μg.
- Pending lack of CRS in all 3 patients, IMAC dose will be escalated to 4 μg.
- Pending lack of CRS in all 3 patients, IMAC dose will be escalated to 8 μg.
- Pending lack of CRS in all 3 patients, IMAC dose will be escalated to 16 μg.
- Pending lack of CRS in all 3 patients, IMAC dose will be escalated to 32 μg.
- Pending lack of CRS in all 3 patients, IMAC dose will be escalated to 64 μg.
- Pending lack of CRS in all 3 patients, IMAC dose will be escalated to 128 μg, etc.
- Escalation will be discontinued in any cohort if MTD will be reached in 2 of 3 patients.

Example 8: Phase 1 Clinical Trial in Patients with B Cell Malignant Diseases (CLL, ALL or NHL) and/or Multiple Myeloma Based on the Use of IMAC Followed by In Vivo Activation of Patient's Lymphocytes with Low-Dose IL-2

The same procedures are done as described in Example 7, using the safe IMAC MTD as discovered in Example 7, followed by in vivo activation of patient's immune system with low dose IL-2 ($10^6$ IU/day) administered subcutaneously for 5 days to investigate if IL-2 activation in vivo in the presence of an optimal safe dose of IMAC induces any serious side effects or CRS due to activating patient's own T cells (in case of any signs of CRS, the dose of IMAC will be reduced to a safer level).

Example 9: Phase 1 Clinical Trial in Patients with B Cell Malignant Diseases (CLL, ALL or NHL) and/or Multiple Myeloma Based on the Use of IMAC Followed by In Vivo Infusion of Haploidentical or Unrelated Donor Lymphocytes The same procedures are done as described in Example 7, using the safe IMAC MTD as discovered in Example 8. In case of any serious side effects or CRS due to activating donor's own T cells, the dose of IMAC or the number of donor lymphocytes will be reduced to a safer level or alternatively subsequent treatment will be based on the use intentionally mismatched donor's NK cells, Donor NK cells can be obtained by deletion of CD3-positive T cells or much simpler by exposure of donor's cells to ionizing radiation (600 cGy) that eliminates proliferation of T cells but retains non-replicating NK function (21, 32). The starting number of donor lymphocytes will consist of $5\times10^7$ cells/kg. In case of CRS, the next patient will be treated with a lower dose of donor lymphocytes of $5\times10^6$ cells/kg Example 10: Phase 1 Clinical Trial in Patients with B Cell Malignant Diseases (CLL, ALL or NHL) and/or Multiple Myeloma Based on the Use of IMAC Followed by In Vivo Infusion of Haploidentical or Unrelated Donor Lymphocytes Activated In Vivo with Low-Dose IL-2

The same procedures will be done as described in Example 9, using the safe doses of IMAC and IL-2 as will be discovered in Example 9. The treatment will consist of safer doses of donor lymphocytes and IL-2 as will be defined in Example 9. Assuming that the starting number of donor lymphocytes will consist of $5\times10^7$ cells/kg. In case of CRS discovered in Example 7, the next patient will be treated with a lower dose of donor lymphocytes of $5\times10^6$ treated in vivo with IL-2 ($1\times10^6$ IU/day, unless the dose of IL-2 will be reduced in Example 7 to $0.5\times10^6$IU/day). If CRS will develop in the $1^{st}$ patient, the $2^{nd}$ patient will be treated with a full dose of donor cells, $5\times10^7$/kg and full dose of IL-2 ($1\times10^6$IU/day) using donor's NK cells. Donor NK cells can be obtained by deletion of CD3-positive T cells or much simpler by exposure of donor's cells to ionizing radiation (600 cGy) that eliminates proliferation of T cells but retains non-replicating NK function. The assumption is that 70-80% of donor lymphocytes are CD3-positive.

Example 11: Phase 1 Clinical Trial in Patients with B Cell Malignant Diseases (CLL, ALL or NHL) and/or Multiple Myeloma Based on the Use of IMAC Followed by Infusion of Haploidentical or Unrelated Donor Lymphocytes T & NK Cells Activated Ex Vivo with IL-2 Prior to Cell Infusion and In Vivo Following Cell Infusion with Low-Dose IL-2

The safe protocol defined in Example 10 will serve as the basis for an identical protocol based on infusion of ex vivo activated donor lymphocytes for 5 days. The safe number of donor lymphocytes containing both T and NK cells or using T cell depleted NK cells will be used and activated in vivo with low dose IL-2 ($1\times10^6$ IU/day if well tolerated or reduced dose of $0.5\times10^6$ IU/day if associated with toxicity or CRS).

Example 12: Phase 1 Clinical Trial in Patients with High-Risk Metastatic Solid Tumors Based on the Use of IMAC Followed by Infusion of Haploidentical or Unrelated Donor Lymphocytes Activated Ex Vivo and/or In Vivo with IL-2

Pending successful results of phase 1 studies as shown in Examples #7-10, several future studies will be designed for treatment of patients with otherwise incurable metastatic solid tumors. Successful Phase 2 and phase 3 will consist of the basis for using the IMAC technology for patients with high-risk cancer at the stage of minimal residual disease, aiming for cure.

The details of the design of any future clinical trial depend on information obtained from the pilot clinical trials described in examples 7-11 and considering potential efficacy that may be suggested even in the course of a phase I clinical trial in view of the exquisite anti-cancer efficacy anticipated. In any event, the goal is to focus on IMAC procedures, both for eradication of cancer and for induction of anti-cancer immunity, that could be applied on a much larger scale, provided that the IMAC treatment will be well tolerated, with no more than transient grade II toxicity.

Example 13: Additional Studies to Improve the Anticipated Therapeutic Effects of IMAC Following determining safe and optimal IMAC concentrations used for in vivo activation of patient's own immune system, donor's immune system and readily available killer cells of activated intentionally mismatched donor lymphocytes, additional procedures will be considered in order to improve the anticipated anti-cancer effects of IMAC, as follows:

1. Start IMAC therapy as early as possible at the stage visible or measurable minimal residual disease that can be accomplished in most patients with cancer, hematological malignancies and solid tumors, following conventional first line treatment since this may represent the best window of opportunity to accomplish cure, when patient's general condition and immune system are still well preserved. Existence of visible or measurable disease by PET/CT imaging, or comparing circulating tumor cells (CTC) or circulating tumor DNA (ctDNA) before and after IMAC treatment will be essential in order to prove clinical efficacy before considering large-scale prospective randomized clinical studies in hematopoietic malignancies and high-risk solid tumors.
2. Her2/neu positive metastatic breast cancer, for example, targeting killer cells with anti-Her2/neu monoclonal antibodies (Herceptin) is an example of a disease category suitable for a pilot clinical trial for investigation of the role of IMAC as a model of metastatic solid tumors.

REFERENCES

1. Slavin S, Or R, Kapelushnik Y, Drakos P, Ackerstein A, Vourka-Karussis U, Weiss L, Nagler A: Immunotherapy of minimal residual disease in conjunction with autologous and allogeneic bone marrow transplantation (BMT). Leukemia 6: 164-166, 1992.
2. Slavin S, Naparstek E, Nagler A, Ackerstein A, Samuel S, Kapelushnik J, Brautbar C, Or R. Allogeneic cell therapy with donor peripheral blood cells and recombinant human interleukin-2 to treat leukemia relapse post allogeneic bone marrow transplantation. Blood 1996; 87:2195-2204.
3. Slavin S, Naparstek E, Nagler A, Ackerstein A, Kapelushnik Y, Or R: Allogeneic cell therapy for relapsed leukemia following bone marrow transplantation with donor peripheral blood lymphocytes. Exp Hematol. 1995; 23:1553-1562.
4. Slavin S, Nagler A, Naparstek E, Kapelushnik Y, Aker M, Cividalli G, Varadi G, Kirschbaum M, Ackerstein A, Samuel S, Ben-Tal O, Eldor A, Or R. Nonmyeloablative stem cell transplantation and cell therapy as an alternative to conventional bone marrow transplantation with lethal cytoreduction for the treatment of malignant and nonmalignant hematologic diseases. Blood 1998; 91(3): 756-763.
5. Or R, Ackerstein A, Nagler A, Amar A, Naparstek E, Varadi G, Kapelushnik J, Samuel S, Pugatsch T, Brautbar C, Slavin S. Allogeneic cell-mediated and cytokine-activated immunotherapy for malignant lymphoma at the stage of minimal residual disease after autologous stem cell transplantation. J. Immunother 1998; 21(6):447-53.
6. Slavin S. Cancer immunotherapy with alloreactive lymphocytes. N. Engl. J. Med. 2000 (Sep. 14); 343:802-803.
7. Nagler A, Ackerstein A, Or R, Naparstek E, Slavin S. Adoptive immunotherapy with haploidentical allogeneic peripheral blood lymphocytes (PBL) following autologous bone marrow transplantation (ABMT). Exp Hematol 2000:28 (11); 1225-1231.
8. Slavin S. Immunotherapy of Cancer with Alloreactive Lymphocytes (Review). Lancet Oncol 2001; 2: 491-98.
9. Nicola Daniele, Maria Cristina Scerpa, Maurizio Caniglia, Chiara Ciammetti, Cecilia Rossi, Maria Ester Bernardo, Franco Locatelli, Giancarlo Isacchi, and Francesco Zinno. Overview of T-cell depletion in haploidentical stem cell transplantation. Blood Transfus. 2012 July; 10(3): 264-272.
10. Luznik L, O'Donnell P V, Symons H J, Chen A R, Leffell M S, Zahurak M et al. HLA-haploidentical bone marrow transplantation for hematologic malignancies using nonmyeloablative conditioning and high-dose, posttransplantation cyclophosphamide. Biol Blood Marrow Transplant 2008; 14: 641-650.
11. Ströhlein M A, Siegel R, Jäger M, Lindhofer H, Jauch K W, Heiss M M. Induction of antitumor immunity by trifunctional antibodies in patients with peritoneal carcinomatosis. J Exp Clin Cancer Res. 2009 Feb. 14; 28:18.

12. Eissler N, Ruf P, Mysliwietz J, Lindhofer H, Mocikat R. Trifunctional bispecific antibodies induce tumor-specific T cells and elicit a vaccination effect. Cancer Res. 2012 Aug. 15; 72(16):3958-66.
13. Morecki S, Lindhofer H, Yacovlev E, Gelfand Y, Slavin S. Use of trifunctional bispecific antibodies to prevent graft versus host disease induced by allogeneic lymphocytes. Blood. 2006; 107:1564-1569.
14. Morecki S, Lindhofer H, Yacovlev E, Gelfand Y, Ruf P, Slavin S. Induction of long-lasting antitumor immunity by concomitant cell therapy with allogeneic lymphocytes and trifunctional bispecific antibody. Exp Hematol. 2008 August; 36(8):997-1003.
15. U.S. Pat. No. 8,066,989
16. U.S. Pat. No. 6,551,592
17. Cohen P, Vourka-Karussis U, Weiss L, Slavin S. Spontaneous and IL-2 induced anti-leukemic and anti-host effects against tumor- and host-specific alloantigens. J Immunol 1993; 151:4803-4810.
18. Slavin S, Shapira M Y, Morecki S, Samuel S, Ackerstein A, Gelfand Y, Resnick I, Bitan M, Or R. Immunotherapy for resistant hematologic malignancies using matched or mismatched rIL-2 activated donor lymphocytes positively selected for CD56+ after allogeneic stem cell transplantation for allogeneic cell therapy without GVHD. 45th ASH Annual Meeting. San Diego, California, USA. Dec. 6-9, 2003. Blood 2003; 102 (11):Abs #5329 p. 400b.
19. Slavin S. Allogeneic cell-mediated immunotherapy at the stage of minimal residual disease following high-dose chemotherapy supported by autologous stem cell transplantation. Acta Haematologica. 2005; 114:214-220.
20. Slavin S, Ackerstein A, Or R, Shapira M Y, Gesundheit B, Askenasy N, Morecki S. Immunotherapy in high-risk chemotherapy-resistant patients with metastatic solid tumors and hematological malignancies using intentionally mismatched donor lymphocytes activated with rIL-2: a phase I study. Cancer Immunol Immunother. 2010 October; 59(10):1511-9.
21. Tsirigotis P, Resnick I B, Kapsimalli V, Dray L, Psarra E, Samuel S, Spyridonidis A, Konsta E, Vikentiou M, Or R, Slavin S, Shapira M Y. Irradiated mononuclear cells express significant in vitro cytotoxic activity: promise for in vivo clinical efficacy of irradiated mismatched donor lymphocytes infusion. Immunotherapy. 2014 April; 6(4): 409-17.
22. Morecki S, Lindhofer H, Yacovlev E, Gelfand Y, Slavin S. Use of trifunctional bispecific antibodies to prevent graft versus host disease induced by allogeneic lymphocytes. Blood. 2006; 107:1564-1569.
23. Morecki S, Lindhofer H, Yacovlev E, Gelfand Y, Ruf P, Slavin S. Induction of long-lasting antitumor immunity by concomitant cell therapy with allogeneic lymphocytes and trifunctional bispecific antibody. Exp Hematol. 2008 August; 36(8):997-1003.
24. Goldenberg D M, Cancer Therapy with Radiolabeled Antibodies. CRC Press, 1995.
25. Petronzelli F, Pelliccia A, Anastasi A M, Lindstedt R, Manganello S, Ferrari L E, Albertoni C, Leoni B, Rosi A, D'Alessio V, Deiana K, Paganelli G, De Santis R. Therapeutic use of avidin is not hampered by antiavidin antibodies in humans. Cancer Biother Radiopharm. 2010 October; 25(5):563-70.
26. Muros M A, Varsaysky M, Iglesias Rozas P, Valdivia J, Delgado J R, Forrer F, Bodei L, Paganelli G. Outcome of treating advanced neuroendocrine tumours with radiolabelled somatostatin analogues. Clin Transl Oncol. 2009 January; 11(1):48-53.
27. Paganelli G, De Cicco C, Ferrari M E, Carbone G, Pagani G, Leonardi M C, Cremonesi M, Ferrari A, Pacifici M, Di Dia A, De Santis R, Galimberti V, Luini A, Orecchia R, Zurrida S, Veronesi U. Intraoperative avidination for radionuclide treatment as a radiotherapy boost in breast cancer: results of a phase II study with (90)Y-labeled biotin. Eur J Nucl Med Mol Imaging. 2010 February; 37(2):203-11.
28. Park J H, Rivière I, Gonen M, Wang X, Sénéchal B, Curran K J, Sauter C, Wang Y, Santomasso B, Mead E, Roshal M, Maslak P, Davila M, Brentjens R J, Sadelain M. Long-Term Follow-up of CD19 CAR Therapy in Acute Lymphoblastic Leukemia. N Engl J Med. 2018 Feb. 1; 378(5):449-459.
29. Panigrahi S, Yacovlev E, Gelfand Y, Schuger L, Slavin S, Morecki S. Intraportal and systemic allogeneic cell therapy in a murine model of hepatic metastatic breast cancer. Cytokines, Cellular & Molecular Therapy. 2002; 7(3):99-106.
30. Morecki S, Yacovlev E, Gelfand Y, Vilensky A, Slavin S. Allogeneic vs syngeneic killer splenocytes as effector cells for induction of graft vs tumor effect. Biology of Blood & Marrow Transplantation. 2004; 10(1):40-48.
31. Ackerstein, a, Morecki S, Gelfand Y, Samuel S, Or R, Slavin S. Outpatient non-myeloablative cell-mediated immunotherapy with intentionally mismatched allogeneic lymphocytes with rIL-2 for patients with metastatic solid tumors. 45th ASH Annual Meeting. San Diego, California, USA. Dec. 6-9, 2003. Blood 2003; 102 (11):Abs #5366 p. 409b.
32. Zarcone D, Tilden A B, Lane V G, Grossi C E. Radiation sensitivity of rating and activated nonspecific cytotoxic cells of T lineage and NK lineage. Blood, 73: 1615-1621, 1989.

The invention claimed is:

1. A method for treating a subject having cancer, the method comprising administering to the subject:

a) one or more Immunotherapeutic Monoclonal Antibody Complexes or Conjugates (IMAC) comprising at least two different monoclonal antibodies, wherein each antibody comprises two hypervariable regions (F(ab')2 domains) and a constant region (Fc domain), and wherein the at least two different antibodies are linked through an Avidin-Biotin connection between biotin moieties covalently coupled to the antibodies and an avidin moiety, wherein the IMAC comprises a first antibody capable of binding to a lymphocyte; and a second antibody capable of binding to at least one antigen on a tumor cell or tumor-specific blood vessel, and b) one or more preactivated mismatched allogeneic lymphocytes.

2. The method of claim 1 wherein the IMAC comprises an antibody capable of binding to a T cell, an NK cell or an NKT cell.

3. The method of claim 1, wherein the method further comprises administering a moiety capable of activating the immune system or an anti-cancer moiety.

4. The method of claim 1, wherein the IMAC comprises antibody binding regions to at least 2 different cell-surface antigens.

5. The method of claim 4, wherein the IMAC comprises a combination of antibodies to two cell-surface antigens of malignant cells selected from the group consisting of: CD19 and CD20; Her2/neu and EGFR; Her2/neu and GD2; Her2/neu and MUC-1; CD38 and CD138; and CD34 and CD133.

6. The method of claim 1, wherein the IMAC comprises at least one monoclonal antibody specific for regulatory T cells or for a cell that can suppress induction of anti-cancer immunity.

7. The method of claim 1, wherein the IMAC comprises at least one antibody is specific to a checkpoint inhibitor.

8. The method of claim 1, wherein the IMAC comprises at least one antibody capable of binding to T cells, NK cells, dendritic cells or macrophages through a domain selected from an F(ab')2 (hypervariable region) domain and an Fc domain (constant region).

9. The method of claim 1, wherein the IMAC comprises at least one antibody capable of binding through its F(ab')2 or Fc domain, to an Fc receptor on activated immune cells selected from the group consisting of NK cells, T cells, NKT cells and macrophages.

10. The method of claim 1, wherein the IMAC comprises: (1) at least one antibody specific to T cells or NK cells selected from the group consisting of: anti-CD2, anti-CD3, anti-CD4, anti-CD8, anti-CD28, anti-CD25, anti-CD80, anti-CD86, anti-CD45RA, anti-CD45RO, anti-CD 134, anti-CD196, anti-CD197, anti-CD62L, anti-CD69, anti-CTLA-4, anti-PD-1 and anti-PD-L1; or (2)

at least one antibody specific to dendritic cells or macrophages, wherein said antibody is selected from the group consisting of: anti-HLA-DR, anti-CD16, anti-CD56, anti-NKG2D, anti-NKG2A, anti-CD94, anti-CD11b, anti-CD14, and anti-CD136; and/or (3) at least one antibody specific to mesenchymal stromal cell markers (MSCs) selected from the group consisting of: anti-CD73, anti-CD105, anti-CD90 and anti-CD200.

11. The method of claim 1, wherein the IMAC comprises an antibody selected from the group consisting of: anti-CD19, anti-CD20, anti-EGFR, anti-HER2, anti-GD2, anti-CD30, anti-CD37, anti-CD38 and anti-CD138.

12. The method of claim 1, wherein the IMAC comprise 3 or 4 antibodies.

13. The method of claim 1, wherein the method comprises selecting a combination of at least two different antibodies suitable for treatment of the subject, creating an IMAC by connecting the at least two antibodies, and administering to the subject a pharmaceutical composition comprising the IMAC.

14. The method of claim 1, wherein the cancer is hematologic malignancy.

15. The method of claim 1, further comprising administering a lymphocyte activating agent.

16. The method of claim 1, wherein the preactivated mismatched allogeneic lymphocytes were pre-activated by cytokines.

17. The method of claim 1, wherein the preactivated mismatched allogeneic lymphocytes were pre-activated by IL-2.

18. A pharmaceutical composition comprising a) at least one Immunotherapeutic Monoclonal Antibody Complexes or Conjugates (IMAC) comprising at least two different monoclonal antibodies, wherein each antibody comprises two hypervariable regions (F(ab')2 domains) and a constant region (Fc domain), and wherein the at least two different antibodies are linked through an Avidin-Biotin connection between biotin moieties covalently coupled to the antibodies and an avidin moiety, wherein the IMAC comprises a first antibody capable of binding to a lymphocyte; and a second antibody capable of binding to at least one antigen on a tumor cell or tumor-specific blood vessel, b) preactivated mismatched allogeneic lymphocytes; and c) a pharmaceutically acceptable carrier, diluent or excipient.

* * * * *